US011484543B2

(12) United States Patent
Lifton et al.

(10) Patent No.: US 11,484,543 B2
(45) Date of Patent: Nov. 1, 2022

(54) COMPOSITIONS AND METHODS FOR DIAGNOSING AND TREATING DISEASES AND DISORDERS ASSOCIATED WITH MUTANT KCNJ5

(71) Applicant: The Rockefeller University, New York, NY (US)

(72) Inventors: Richard Lifton, New York, NY (US); Ute Scholl, Dusseldorf (DE)

(73) Assignee: The Rockefeller University, New York, NY (US)

( * ) Notice: Subject to any disclaimer, the term of this patent is extended or adjusted under 35 U.S.C. 154(b) by 272 days.

(21) Appl. No.: 16/614,401

(22) PCT Filed: May 18, 2018

(86) PCT No.: PCT/US2018/033362
§ 371 (c)(1),
(2) Date: Nov. 18, 2019

(87) PCT Pub. No.: WO2018/213690
PCT Pub. Date: Nov. 22, 2018

(65) Prior Publication Data
US 2020/0147113 A1   May 14, 2020

Related U.S. Application Data

(60) Provisional application No. 62/507,884, filed on May 18, 2017.

(51) Int. Cl.
*A61K 31/7048* (2006.01)
*G01N 33/74* (2006.01)

(52) U.S. Cl.
CPC ....... *A61K 31/7048* (2013.01); *G01N 33/743* (2013.01)

(58) Field of Classification Search
None
See application file for complete search history.

(56) References Cited

U.S. PATENT DOCUMENTS

| 2013/0195871 A1* | 8/2013 | Ghayur | A61P 15/00 424/136.1 |
| 2014/0127126 A1* | 5/2014 | Lifton | C12Q 1/6883 424/1.11 |
| 2017/0128479 A1 | 5/2017 | Kim | |

OTHER PUBLICATIONS

Tauber, P., Penton, D., Stindl, J., Humberg, E., Tegtmeier, I., Sterner, C., . . . Warth, R. (2014). Pharmacology and pathophysiology of mutated KCNJ5 found in adrenal aldosterone-producing adenomas. Endocrinology, 155(4), 1353-1362. (Year: 2014).*
Oki, K., Plonczynski, M. W., Luis Lam, M., Gomez-Sanchez, E. P., & Gomez-Sanchez, C. E. (2012). Potassium channel mutant KCNJ5 T158A expression in HAC-15 cells increases aldosterone synthesis. Endocrinology, 153(4), 1774-1782. (Year: 2012).*
Akerstrom et al., "Comprehensive Re-Sequencing of Adrenal Aldosterone Producing Lesions Reveal Three Somatic Mutations near the KCNJ5 Potassium Channel Selectivity Filter", PLoS One, 2012, 7:e41926.
Boulkroun et al., "Prevalence, Clinical, and Molecular Correlates of KCNJ5 Mutations in Primary Aldosteronism", Hyptertension, 2012, 59:592-598.
Calvo-Romero et al., "Recurrence of adrenal aldosterone-producing adenoma", Postgrad. Med. J., 2000, 76:160-161.
Caroccia et al. "Macrolides Blunt Aldosterone Biosynthesis. A Proof-of-Concept Study in KCNJ5 Mutated Adenoma Cells Ex Vivo", Hypertension, 2017, 70:1238-1242.
Choi et al., "Genetic diagnosis by whole exome capture and massively parallel DNA sequencing", Proc. Natl. Acad. Sci. U.S.A., 2009, 106:19096-19101.
Choi et al., "K+ Channel Mutations in Adrenal Aldosterone-Producing Adenomas and Hereditary Hypertension", Science, 2011, 331:768-772.
Colao et al., "Medical treatment of prolactinomas", Nat. Rev. Endocrinol., 2011, 7:267-278.
Fernandes-Rosa et al., "Genetic Spectrum and Clinical Correlates of Somatic Mutations in Aldosterone-Producing Adenoma", Hypertension, 2014, 64:354-361.
Flynn et al., "Erythromycin. II. Des-N-methylerythromycin and N-Methyl-C14-erythromycin" J. Am. Chem. Soc. 1955, 77:3104-3106.
Funder et al., "Endocrine Society. Case detection, diagnosis, and treatment of patients with primary aldosteronism : an endocrine society clinical practice guideline", J. Clin. Endocrinol. Metab., 2008, 93:3266-3281.
Ghose et al., "Medical Management of Aldosterone-Producing Adenomas", Ann. Intern. Med., 1999, 131:105-108.
Gordon et al., "Primary aldosteronism: hypertension with a genetic basis", Lancet, 1992, 340:159-161.
Hong et al., "Genetics of Aldosterone-Producing Adenoma in Korean Patients", PLoS One, 2016, 11:e0147590.
Kitamoto et al., "Comparison of cardiovascular complications in patients with and without KCNJ5 gene mutations harboring aldosterone-producing adenomas", J. Atheroscler. Thromb., 2015, 22:191-200.
Lenzini et al., "A Meta-Analysis of Somatic KCNJ5 K+ Channel Mutations in 1636 Patients With an Aldosterone-Producing Adenoma", J. Clin. Endocrinol. Metab, 2015, 100:E1089-E1095.
Litton et al., "Achimaeric IIβ-hydroxylase/aldosterone synthase gene causes glucocorticoid-remediable aldosteronism and human hypertension", Nature , 1992, 355:262-265.
Lim et al., "A comparative risk assessment of burden of disease and injury attributable to 67 risk factors and risk factor clusters in 21 regions, 1990-2010: a systematic analysis for the Global Burden of Disease Study 2010", Lancet, 2012, 380:2224-2260.

(Continued)

*Primary Examiner* — Dale R Miller
(74) *Attorney, Agent, or Firm* — Riverside Law LLP

(57) ABSTRACT

The present invention relates to the discovery that mutant KCNJ5 is associated with adrenal diseases and disorders. The invention includes compositions and methods for the diagnosis and treatment of adrenal diseases and disorders, based upon the presence or absence of a KCNJ5 mutation that is associated with an adrenal disease or disorder.

16 Claims, 18 Drawing Sheets

Specification includes a Sequence Listing.

(56) References Cited

OTHER PUBLICATIONS

Litchfield et al., "Evaluation of the Dexamethasone Suppression Test for the Diagnosis of Glucocorticoid-Remediable Aldosteronism", J. Clin. Endocrinol. Metab., 1997, 82:3570-3573.

Mathur et al., "Consequences of Adrenal Venous Sampling in Primary Hyperaldosteronism and Predictors of Unilateral Adrenal Disease", J. Am. Coll. Surg., 2010, 211:384-390.

Mcewan et al., "Control of cell proliferation in the rat adrenal gland in vivo by the renin-angiotensin system", Am. J. Physiol., 1996, 271:E192-E198.

Parnham, "Immunomodulatory effects of antimicrobials in the therapy of respiratory tract infections", Curr. Opin. Infect. Dis., 2005, 18:125-131.

Pawlikowski et al., "Angiotensins II and IV Stimulate the Rat Adrenocortical Cell Proli. Eration Acting Via DI . . . Erent Receptors", Endocr. Regul., 2001, 35:139-142.

Puri et al., "Roxithromycin: a pharmacokinetic review of a macrolide", J. Antimicrob. Chemother., 1987, 20 Suppl. B:89-100.

Rossi et al., "A Prospective Study of the Prevalence of Primary Aldosteronism in 1,125 Hypertensive Patients", J. Am. Coll. Cardiol., 2006, 48:2293-2300.

Rossi et al., "Primary aldosteronism: an update on screening, diagnosis and treatment", J. Hypertens., 2008, 26:613-621.

Rossi, "Diagnosis and treatment of primary aldosteronism", Endocrinol. Metab. Clin. North Am., 2011, 40:313-332.

Scholl et al. "Macrolides selectively inhibit mutant KCNJ5 potassium channels that cause aldosterone producing adenoma" J Clin Invest., 2017,127:2739-2750.

Scholl et al., "Hypertension with or without adrenal hyperplasia due to different inherited mutations in the potassium channel KCNJ5", Proc. Natl. Acad. Sci. U.S.A., 2012, 109:2533-2538.

Scholl et al., "Novel Somatic Mutations in Primary Hyperaldosteronism are related to the Clinical, Radiological and Pathological Phenotype" Clin. Endocrinol. 2015, 83:779-789.

Schulte et al., "Pharmacokinetics of Aldosterone in Patients With Addison's Disease: Effect of Rifampicin Treatment on Glucocorticoid and Mineralocorticoid Metabolism", Clin. Endocrinol., 1987, 27:655-662.

Shaw et al., "Structure-Activity Relationships of 9-Substituted-9-Dihydroerythromycin-Based Motilin Agonists: Optimizing for Potency and Safety" J. Med. Chem. 2009, 52:6851-6859.

Spät et al., "Control of Aldosterone Secretion: A Model for Convergence in Cellular Signaling Pathways", Physiol. Rev., 2004, 84:489-539.

Stowasser et al., "Primary aldosteronism", Best Pract. Res. Clin. Endocrinol. Metab., 2003, 17:591-605.

Sunazuka et al., "Motilides, Macrolides with Gastrointestinal Motor Stimulating Activity: II. Quaternary N-Substituted Derivatives of 8, 9-Anhydroerythromycin A 6, 9-Hemiacetal and 9, 9-Dihydroerythromycin A 6, 9-Epoxide", Chem. Pharm. Bull., 1989, 37:2701-2709.

Tanabe et al., "Angiotensin II stimulates both aldosterone secretion and DNA synthesis via type 1 but not type 2 receptors in bovine adrenocortical cells", J. Endocrinol. Invest., 1998 21:668-672.

Tsuzuki et al., "Motilides, Macrolides with Gastrointestinal Motor Stimulating Activity: I. O-Substituted and Tertiary N-Substituted Derivatives of 8, 9-Anhydroerythromycin A 6, 9-Hemiacetal", Chem. Pharm Bull., 1989, 37:2687-2700.

Wang et al., "Comparison of Aldosterone Production among Human Adrenocortical Cell Lines", Horm. Metab. Res., 2012, 44:245-250.

Westerdahl et al., "Re☐ evaluation of the fludrocortisone test: duration, NaCl supplementation and cut☐ off limits for aldosterone", Scand. J. Clin. Lab. Invest., 2009, 69:234-241.

Williams, Tracy, A et al. "KCNJ5 Mutations ar ehte Most Frequent Genetic Alternation in Primary Aldosteronism." Hypertension. vol. 65, No. 3, Mar. 1, 2015, pp. 507-509.

Young, "Primary aldosteronism: renaissance of a syndrome", Clin. Endocrinol., 2007, 66:607-618.

Zheng et al., "Clinical Characteristics of Somatic Mutations in Chinese Patients With Aldosterone-producing Adenoma", Hypertension, 2015, 65:622-628.

\* cited by examiner

Highly active compounds
($KCNJ5^{G387R}$ $IC_{50}$ < 1 µM)

Roxithromycin, $IC_{50}$ = 0.23 µM

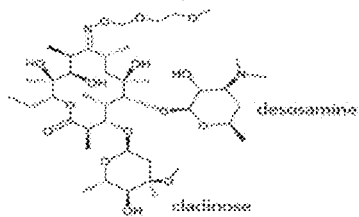

Roxithromycin D7, $IC_{50}$ = 0.58 µM

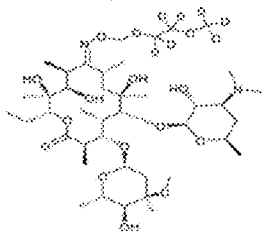

Idremcinal, $IC_{50}$ = 0.60 µM

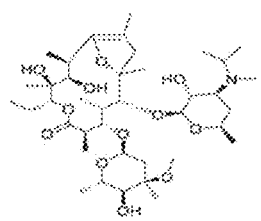

Pseudo Erythromycin A Enol Ether, $IC_{50}$ = 0.65 µM

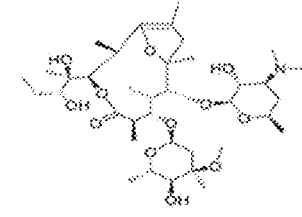

Clarithromycin, $IC_{50}$ = 0.71 µM

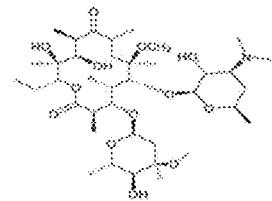

N-demethyl Roxithromycin, $IC_{50}$ = 0.82 µM

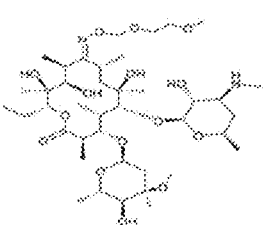

Moderately active compounds
(1 µM < $KCNJ5^{G387R}$ $IC_{50}$ < 15 µM)

Erythromycin B, $IC_{50}$ = 1.23 µM

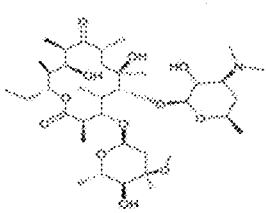

Erythromycin A Oxime, $IC_{50}$ = 2.88 µM

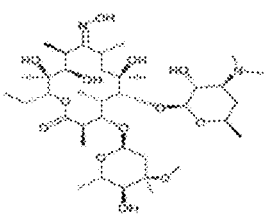

Azithromycin, $IC_{50}$ = 5.69 µM

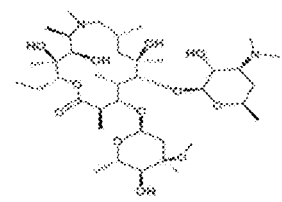

Anhydroerythromycin A, $IC_{50}$ = 8.60 µM

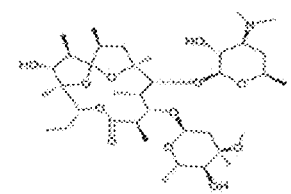

Erythromycin C, $IC_{50}$ = 9.19 µM

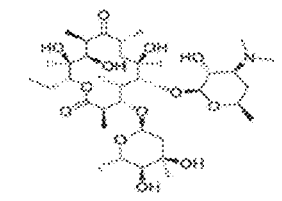

Erythromycin (main component Erythromycin A, also contains variable amounts of Erythromycin B, C and D), $IC_{50}$ = 10.53 µM

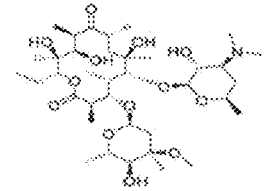

Inactive compounds (selection; $KCNJ5^{G387R}$ $IC_{50}$ > 15 µM or inactive in primary screen)

Dirithromycin, $IC_{50}$ = 15.8 µM

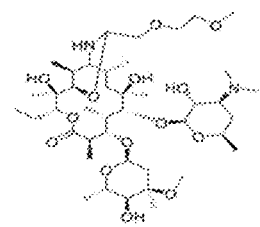

Flurithromycin, inactive

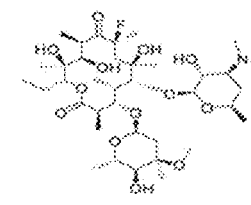

Decladinose Roxithromycin, inactive

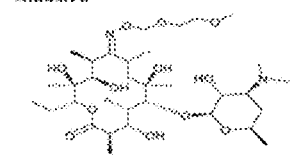

Telithromycin, inactive

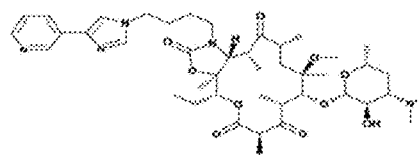

Troleandomycin, inactive

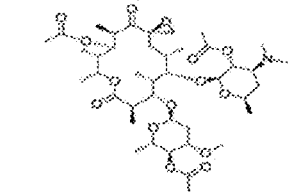

Josamycin, inactive

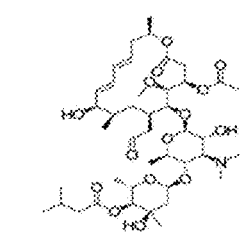

Figure 5

| Compound ID | Supplier | Supplier ID | Name | G151R IC₉₀ | Hill | Minimum inhibition (%) | R² | Maximum inhibition (%) | L168R IC₅₀ | Hill | Minimum inhibition (%) | R² | Maximum inhibition (%) | WT IC₅₀ | Hill | Minimum inhibition (%) | R² | Maximum inhibition (%) | mean IC50 / G151R L168R |
|---|---|---|---|---|---|---|---|---|---|---|---|---|---|---|---|---|---|---|---|
| YU0238064 | Toronto Research | R700852 | Roxithromycin-D7 | 0.58 | 1.26 | 3.67 | 0.9 | 96.22 | 0.68 | 4.37 | 3.95 | 0.96 | 76.07 | No Fit | N/A | N/A | N/A | N/A | 1.26 |
| YU0223163 | NCI | NSC18883 | | 0.44 | 12.87 | 5.54 | 0.98 | 69.05 | 1.06 | -9.84 | 10.55 | 0.71 | 1.09 | No Fit | N/A | N/A | N/A | N/A | 1.5 |
| YU0228063 | Toronto Research | D251265 | N-demethyl Roxithromycin | 0.82 | 1.84 | 4.5 | 0.95 | 96.2 | 1.18 | 2.68 | 1.12 | 0.99 | 76.95 | No Fit | N/A | N/A | N/A | N/A | 2 |
| YU0164430 | ChemDiv | D089-0731 | | 1.13 | 37.2 | 3.4 | 0.84 | 53.42 | 2.73 | 3.29 | -1.11 | 0.95 | 49.45 | 5.1 | 1.74 | -4.67 | 0.82 | 80 | 3.86 |
| YU0224116 | Enzo | KC-159 | U-37883A hydrochloride | 1.07 | 7.58 | 12.84 | 0.92 | 60.42 | 3.28 | 3.86 | 0.14 | 0.97 | 6.81 | N/A | N/A | N/A | N/A | N/A | 4.36 |
| YU0164429 | ChemDiv | D089-0725 | | 0.51 | 5.25 | 9.58 | 0.92 | 64.38 | 4.76 | 1.54 | 0.39 | 0.99 | 59.85 | 4.09 | 1.52 | 12.04 | 0.87 | 75 | 5.27 |
| YU0158463 | ChemDiv | 5137-3628 | | 0.68 | 1.98 | 9.85 | 1 | 68.87 | 5.04 | 2.84 | 0.83 | 0.96 | 12 | N/A | N/A | N/A | N/A | N/A | 5.72 |
| YU0158681 | ChemDiv | 5320-4034 | | 2.05 | 2.33 | 11.42 | 0.99 | 73.8 | 3.85 | 3.92 | -0.16 | 0.96 | 14.06 | N/A | N/A | N/A | N/A | N/A | 5.91 |
| YU0228018 | Toronto Research | E650010 | Erythromycin A Oxime (Roxithromycin Impurity C) | 1.45 | 1.05 | -3.29 | 0.97 | 110.11 | 4.59 | 2.35 | 1.01 | 0.97 | 47 | No Fit | N/A | N/A | N/A | N/A | 6.04 |
| YU0164352 | ChemDiv | D089-0316 | | 4.05 | 1.88 | 2.68 | 0.95 | 58.32 | 2.31 | 1.26 | 0.06 | 0.93 | 3.6 | 4.9 | 1.74 | 16.74 | 0.72 | 50 | 6.36 |
| YU0440261 | Enzo | DL-566 | Nelfinavir mesylate | 5.72 | 4.11 | 3.67 | 0.98 | 70 | 1.77 | 1.06 | -0.35 | 0.86 | 10 | N/A | N/A | N/A | N/A | N/A | 7.49 |
| YU0170857 | ChemDiv | 3572-5949 | | 3.24 | 1.97 | 3.79 | 0.99 | 97.9 | 4.25 | 8.14 | 1.61 | 0.99 | 21.04 | 3.84 | 1.83 | 10.69 | 0.95 | 65 | 7.49 |
| YU0164426 | ChemDiv | D089-4562 | | 2.08 | 1.23 | 1.27 | 0.92 | 59.28 | 5.5 | 1.24 | 0.1 | 0.74 | 8.88 | 0.92 | 1.6 | 13.89 | 0.91 | 39.54 | 7.58 |
| YU0439827 | Microsource | 2300165 | Aristolochic hydrochloride | 4.31 | 2.37 | 12.29 | 0.97 | 80 | 3.35 | 3.08 | 1 | 0.92 | 5.49 | N/A | N/A | N/A | N/A | N/A | 7.66 |
| YU0223483 | NCI | NSC341196 | | 2.06 | 3.6 | 2.12 | 0.98 | 71.07 | 5.61 | 3.23 | 2.85 | 0.9 | 32 | No Fit | N/A | N/A | N/A | N/A | 7.67 |
| YU0164347 | ChemDiv | D089-0297 | | 3.98 | 1.45 | 2.77 | 0.99 | 75.58 | 3.87 | 8.97 | 0.37 | 0.77 | 4.26 | 4.59 | 5.49 | 8.8 | 0.88 | 59.58 | 7.85 |
| YU0226705 | Microsource | 1502084 | Proadifen hydrochloride | 4.87 | 3.33 | 9.56 | 0.97 | 60 | 3.94 | 8.36 | 0.85 | 0.85 | 5.6 | N/A | N/A | N/A | N/A | N/A | 8.81 |

Figure 7A

| Compound ID | Supplier | Supplier ID | Name | G151R IC50 | G151R HB | G151R Minimum inhibition (%) | G151R R² | G151R Maximum inhibition (%) | L168R IC50 | L168R HB | L168R Minimum inhibition (%) | L168R R² | L168R Maximum inhibition (%) | WT IC50 | WT HB | WT Minimum inhibition (%) | WT R² | WT Maximum inhibition (%) | mean IC50 G151R L168R |
|---|---|---|---|---|---|---|---|---|---|---|---|---|---|---|---|---|---|---|---|
| YU164423 | ChemDiv | D0889-0559 | | 5 | 1.47 | 1.57 | 0.93 | 73.86 | 5.88 | 2.9 | 0.26 | 0.91 | 10 | 4.15 | 1.13 | 18.43 | 0.71 | 100 | 8.88 |
| YU156203 | ChemDiv | 3132-1074 | | 5.28 | 1.45 | 9.73 | 0.99 | 100 | 3.74 | 3.11 | 0.17 | 0.91 | 7.57 | N/A | N/A | N/A | N/A | N/A | 9.02 |
| YU161687 | ChemDiv | 8017-3019 | | 5.14 | 3.68 | 7.74 | 0.97 | 60 | 3.9 | 7.88 | 0.85 | 0.88 | 6.41 | N/A | N/A | N/A | N/A | N/A | 9.04 |
| YU164420 | ChemDiv | D0889-0547 | | 4.24 | 1.46 | 0.2 | 0.92 | 84.54 | 4.95 | 3.66 | -2.23 | 0.84 | 5.35 | No Fit | N/A | N/A | N/A | N/A | 9.19 |
| YU164427 | ChemDiv | D0889-0563 | | 4.31 | 2.28 | 6.73 | 0.98 | 70 | 4.97 | 3.01 | 0.94 | 0.84 | 8 | 4.95 | 1.38 | 11.99 | 0.85 | 80 | 9.28 |
| YU156202 | ChemDiv | 3132-1071 | | 4.4 | 1.43 | 9.01 | 0.95 | 88.62 | 5.58 | 4.08 | 0.5 | 0.86 | 9 | N/A | N/A | N/A | N/A | N/A | 9.97 |
| YU200116 | ChemDiv | G281-2440 | | 5.3 | 4.05 | 4.54 | 0.99 | 80 | 5.06 | 6.58 | 0.84 | 0.92 | 20.2 | No Fit | N/A | N/A | N/A | N/A | 10.36 |
| YU207147 | ChemDiv | G856-6079 | | 3.62 | 2.72 | 2.76 | 0.9 | 59.26 | 7.41 | 6.31 | 0.81 | 0.93 | 8.45 | No Fit | N/A | N/A | N/A | N/A | 11.03 |
| YU040325 | Enzo | DI-357 | Clarithromycin | 8.38 | 1.55 | 4.77 | 0.99 | 100 | 2.98 | 1.8 | 0.27 | 0.94 | 10 | N/A | N/A | N/A | N/A | N/A | 11.36 |
| YU171244 | ChemDiv | 5340-0013 | | 5.79 | 3.93 | 6.15 | 0.99 | 70 | 6.22 | 20.13 | 1.52 | 0.76 | 5.26 | No Fit | N/A | N/A | N/A | N/A | 12.01 |
| YU164410 | ChemDiv | D0889-0525 | | 5.52 | 4.96 | 1.23 | 0.93 | 60.3 | 6.5 | 9.82 | 0.2 | 1 | 41.02 | No Fit | N/A | N/A | N/A | N/A | 12.02 |
| YU155936 | ChemDiv | 2434-0330 | | 7.48 | 2.11 | 8.92 | 1 | 100 | 5.24 | 3.9 | 0.76 | 0.98 | 18 | No Fit | N/A | N/A | N/A | N/A | 12.71 |
| YU034553 | Microsource | 1501176 | Erythromycin estolate | 7.85 | 1.52 | 8.8 | 0.98 | 75.76 | 6.64 | 1.84 | 2.28 | 0.9 | 8 | N/A | N/A | N/A | N/A | N/A | 14.49 |
| YU194117 | ChemDiv | P471-0014 | | 6.44 | 3.92 | 2.41 | 0.96 | 100 | 9.08 | 77.1 | -4.03 | 0.92 | 12.53 | 6.69 | 3.4 | 4.06 | 0.69 | 30.41 | 15.52 |
| YU164416 | ChemDiv | D0889-0533 | | 6.87 | 3.76 | 0.49 | 0.97 | 91.29 | 9.61 | 6.67 | -1.13 | 0.79 | 12.23 | No Fit | N/A | N/A | N/A | N/A | 15.88 |
| YU159856 | ChemDiv | 6456-0125 | | 8.37 | 1.5 | 7.88 | 0.99 | 100 | 9.06 | 19 | 0.22 | 0.88 | 14 | N/A | N/A | N/A | N/A | N/A | 17.43 |
| YU155502 | Microsource | 1500280 | Erythromycin | 10.53 | 1.4 | 3.55 | 0.87 | 90 | 11.76 | 1.31 | 0.71 | 0.94 | 25 | No Fit | N/A | N/A | N/A | N/A | 22.29 |
| YU221968 | NCI | NSC645033 | Pyrimidine | 3.42 | 2.71 | 5.43 | 0.98 | 64.56 | No Fit | N/A | N/A | N/A | N/A | No Fit | N/A | N/A | N/A | N/A | N/A |
| YU164338 | ChemDiv | D0889-0264 | | 1.72 | 1.42 | 5.91 | 0.84 | 17.84 | No Fit | N/A | N/A | N/A | N/A | No Fit | N/A | N/A | N/A | N/A | N/A |
| YU221408 | NCI | NSC719276 | Fulvestrant | 1.93 | 1.15 | -1.21 | 0.9 | 40.71 | No Fit | N/A | N/A | N/A | N/A | No Fit | N/A | N/A | N/A | N/A | N/A |
| YU176099 | ChemDiv | C700-2077 | | 2.92 | 1.57 | 4.14 | 0.95 | 59.77 | No Fit | N/A | N/A | N/A | N/A | No Fit | N/A | N/A | N/A | N/A | N/A |
| YU187648 | ChemDiv | E762-2304 | | 3.66 | 4.41 | 3.35 | 0.98 | 33.46 | No Fit | N/A | N/A | N/A | N/A | No Fit | N/A | N/A | N/A | N/A | N/A |
| YU161684 | ChemDiv | 8017-2854 | | 3.75 | 1.91 | 10.14 | 0.96 | 60 | No Fit | N/A | N/A | N/A | N/A | N/A | N/A | N/A | N/A | N/A | N/A |
| YU164421 | ChemDiv | D0889-0254 | | 3.94 | 1.47 | 2.29 | 0.97 | 64.01 | No Fit | N/A | N/A | N/A | N/A | 1.12 | 16.58 | 17.97 | 0.93 | 35.28 | N/A |

| Compound ID | Supplier | Supplier ID | Name | G151R IC₅₀ | G151R Hill | G151R Minimum inhibition (%) | G151R R² | G151R Maximum inhibition (%) | L168R IC₅₀ | L168R Hill | L168R Minimum inhibition (%) | L168R R² | L168R Maximum inhibition (%) | WT IC₅₀ | WT Hill | WT Minimum inhibition (%) | WT R² | WT Maximum inhibition (%) | mean IC50 G151R / L168R |
|---|---|---|---|---|---|---|---|---|---|---|---|---|---|---|---|---|---|---|---|
| YU195258 | ChemDiv | F560-0413 | | 4.05 | 11.03 | 3.39 | 1 | 65 | No Fit | N/A | N/A | N/A | N/A | No Fit | N/A | N/A | N/A | N/A | N/A |
| YU212319 | ChemDiv | L150-0457 | | 4.05 | 15.94 | 1.6 | 0.98 | 35.53 | No Fit | N/A | N/A | N/A | N/A | No Fit | N/A | N/A | N/A | N/A | N/A |
| YU179100 | ChemDiv | D089-0253 | | 4.1 | 4.46 | 3.25 | 0.92 | 24.95 | No Fit | N/A | N/A | N/A | N/A | No Fit | N/A | N/A | N/A | N/A | N/A |
| YU164362 | ChemDiv | D089-0344 | | 4.13 | 4.35 | 3.37 | 0.96 | 31.22 | No Fit | N/A | N/A | N/A | N/A | No Fit | N/A | N/A | N/A | N/A | N/A |
| YU164351 | ChemDiv | D089-0311 | | 4.15 | 3.31 | 3.75 | 0.98 | 71.94 | No Fit | N/A | N/A | N/A | N/A | No Fit | N/A | N/A | N/A | N/A | N/A |
| YU156667 | ChemDiv | J534-0434 | | 4.19 | 1.34 | 2.76 | 0.86 | 57.23 | No Fit | N/A | N/A | N/A | N/A | N/A | N/A | N/A | N/A | N/A | N/A |
| YU200692 | ChemDiv | G281-1685 | | 4.34 | 5.25 | 3.41 | 0.88 | 23.31 | No Fit | N/A | N/A | N/A | N/A | No Fit | N/A | N/A | N/A | N/A | N/A |
| YU173899 | ChemDiv | C200-9149 | | 4.48 | 2.07 | 6.28 | 0.97 | 80 | No Fit | N/A | N/A | N/A | N/A | No Fit | N/A | N/A | N/A | N/A | N/A |
| YU224969 | Microsource | 1503106 | Bepridil hydrochloride | 4.56 | 7.01 | 5.2 | 0.99 | 64.13 | No Fit | N/A | N/A | N/A | N/A | N/A | N/A | N/A | N/A | N/A | N/A |
| YU155939 | ChemDiv | 2434-0139 | | 4.59 | 5.97 | 0.64 | 0.97 | 47.39 | No Fit | N/A | N/A | N/A | N/A | N/A | N/A | N/A | N/A | N/A | N/A |
| YU034516 | Enzo | AC-124 | Propafenone | 4.71 | 5.3 | 1.92 | 0.97 | 50 | No Fit | N/A | N/A | N/A | N/A | No Fit | N/A | N/A | N/A | N/A | N/A |
| YU200104 | ChemDiv | G281-1947 | | 4.88 | 6.01 | 4.69 | 0.76 | 57.8 | No Fit | N/A | N/A | N/A | N/A | No Fit | N/A | N/A | N/A | N/A | N/A |
| YU199271 | ChemDiv | G318-0224 | | 4.89 | 4.99 | 2.71 | 0.99 | 95 | No Fit | N/A | N/A | N/A | N/A | N/A | N/A | N/A | N/A | N/A | N/A |
| YU163288 | ChemDiv | C620-0363 | | 4.9 | 2.94 | 9.78 | 0.97 | 50 | No Fit | N/A | N/A | N/A | N/A | N/A | N/A | N/A | N/A | N/A | N/A |
| YU225091 | Microsource | 1500591 | Trifluoperazine hydrochloride | 4.97 | 2.42 | 5.78 | 0.96 | 40 | No Fit | N/A | N/A | N/A | N/A | N/A | N/A | N/A | N/A | N/A | N/A |
| YU205248 | ChemDiv | G764-0071 | | 5.03 | 2.37 | 2.03 | 0.86 | 58.52 | No Fit | N/A | N/A | N/A | N/A | No Fit | N/A | N/A | N/A | N/A | N/A |
| YU164343 | ChemDiv | D089-0287 | | 5.05 | 2.4 | 5.78 | 0.94 | 65 | No Fit | N/A | N/A | N/A | N/A | 5.16 | 2.41 | 11.67 | 0.84 | 120 | N/A |
| YU164400 | ChemDiv | D089-0499 | | 5.09 | 2.05 | 2.87 | 0.9 | 26.98 | No Fit | N/A | N/A | N/A | N/A | No Fit | N/A | N/A | N/A | N/A | N/A |
| YU161686 | ChemDiv | 8017-3017 | | 5.14 | 2.23 | 3.27 | 0.9 | 30 | No Fit | N/A | N/A | N/A | N/A | N/A | N/A | N/A | N/A | N/A | N/A |
| YU188170 | ChemDiv | E864-1074 | | 5.14 | 6.8 | 1.3 | 0.99 | 25.45 | No Fit | N/A | N/A | N/A | N/A | No Fit | N/A | N/A | N/A | N/A | N/A |
| YU171246 | ChemDiv | 5340-1529 | | 5.29 | 5.14 | 3.04 | 0.71 | 38.01 | No Fit | N/A | N/A | N/A | N/A | 3.61 | 3.66 | 1.27 | 0.89 | 29.78 | N/A |
| YU194148 | ChemDiv | F471-0857 | | 5.3 | 2.91 | 3.15 | 0.98 | 82.52 | No Fit | N/A | N/A | N/A | N/A | No Fit | N/A | N/A | N/A | N/A | N/A |
| YU176768 | ChemDiv | 3141-0464 | | 5.37 | 5.69 | 3.75 | 0.99 | 60 | No Fit | N/A | N/A | N/A | N/A | No Fit | N/A | N/A | N/A | N/A | N/A |

| Compound ID | Supplier | Supplier ID | Name | G151R IC$_{50}$ | Hill | Minimum inhibition (%) | R² | Maximum inhibition (%) | L168R IC$_{50}$ | Hill | Minimum inhibition (%) | R² | Maximum inhibition (%) | WT IC$_{50}$ | Hill | Minimum inhibition (%) | R² | Maximum inhibition (%) | mean IC50 G151R L168R |
|---|---|---|---|---|---|---|---|---|---|---|---|---|---|---|---|---|---|---|---|
| YL039449 | NCC | SAM#0124 6981 | Indatraline | 5.37 | 1.7 | 9.85 | 0.99 | 100 | No Fit | N/A | N/A | N/A | N/A | N/A | N/A | N/A | N/A | N/A | N/A |
| YU175883 | ChemDiv | C530-0280 | | 5.44 | 6.28 | 2.07 | 0.98 | 36 | No Fit | N/A | N/A | N/A | N/A | No Fit | N/A | N/A | N/A | N/A | N/A |
| YU208326 | ChemDiv | J066-1570 | | 5.47 | 1.96 | 2.24 | 0.91 | 42 | No Fit | N/A | N/A | N/A | N/A | No Fit | N/A | N/A | N/A | N/A | N/A |
| YU195274 | ChemDiv | F586-1522 | | 5.55 | 3.52 | 4.46 | 0.97 | 30 | No Fit | N/A | N/A | N/A | N/A | No Fit | N/A | N/A | N/A | N/A | N/A |
| YU156201 | ChemDiv | 3132-1065 | | 5.56 | 1.67 | 7.49 | 0.99 | 100 | No Fit | N/A | N/A | N/A | N/A | N/A | N/A | N/A | N/A | N/A | N/A |
| YU207124 | ChemDiv | G856-5896 | | 5.62 | 3.19 | 3.56 | 0.97 | 72 | No Fit | N/A | N/A | N/A | N/A | 0.17 | -0.79 | -16.77 | 0.76 | 1.2 | N/A |
| YU192559 | ChemDiv | E351-0044 | | 5.64 | 5.27 | 0.99 | 1 | 50 | No Fit | N/A | N/A | N/A | N/A | No Fit | N/A | N/A | N/A | N/A | N/A |
| YU197082 | ChemDiv | F788-0051 | | 5.82 | 1.94 | 4.93 | 0.92 | 60 | No Fit | N/A | N/A | N/A | N/A | No Fit | N/A | N/A | N/A | N/A | N/A |
| YU205819 | ChemDiv | G786-2333 | | 5.89 | 3.57 | -2.2 | 0.98 | 50 | No Fit | N/A | N/A | N/A | N/A | No Fit | N/A | N/A | N/A | N/A | N/A |
| YU206375 | ChemDiv | G809-0126 | | 6.16 | 3.05 | 3.12 | 0.98 | 52 | No Fit | N/A | N/A | N/A | N/A | No Fit | N/A | N/A | N/A | N/A | N/A |
| YU177904 | ChemDiv | C796-1275 | | 6.23 | 1.86 | 3.12 | 0.94 | 25 | No Fit | N/A | N/A | N/A | N/A | N/A | N/A | N/A | N/A | N/A | N/A |
| YU182169 | ChemDiv | D393-0253 | | 6.35 | 3.7 | 1.13 | 0.97 | 60 | No Fit | N/A | N/A | N/A | N/A | No Fit | N/A | N/A | N/A | N/A | N/A |
| YU226729 | Microsource | 1503118 | Triflupromazine hydrochloride | 6.42 | 1.64 | 5.54 | 0.91 | 50 | No Fit | N/A | N/A | N/A | N/A | N/A | N/A | N/A | N/A | N/A | N/A |
| YU225090 | Enzo | CA-305 | Phenoxybenzamine hydrochloride | 6.5 | 3.6 | 5.01 | 1 | 100 | No Fit | N/A | N/A | N/A | N/A | N/A | N/A | N/A | N/A | N/A | N/A |
| YU164350 | ChemDiv | D089-0310 | | 6.71 | 1.91 | 1.29 | 0.78 | 22 | No Fit | N/A | N/A | N/A | N/A | No Fit | N/A | N/A | N/A | N/A | N/A |
| YU103748 | Enzo | DL-247 | Clemastine | 6.82 | 1.91 | 7.65 | 0.99 | 86.42 | No Fit | N/A | N/A | N/A | N/A | N/A | N/A | N/A | N/A | N/A | N/A |
| YU177007 | ChemDiv | C700-2100 | | 7.19 | 1.98 | 3.89 | 0.77 | 42 | No Fit | N/A | N/A | N/A | N/A | No Fit | N/A | N/A | N/A | N/A | N/A |
| YU164355 | ChemDiv | D089-0323 | | 7.19 | 2.52 | 3.08 | 0.85 | 50 | No Fit | N/A | N/A | N/A | N/A | No Fit | N/A | N/A | N/A | N/A | N/A |
| YU164332 | ChemDiv | D089-0232 | | 7.43 | 1.31 | 2.25 | 0.96 | 43.1 | No Fit | N/A | N/A | N/A | N/A | 6.1 | 2.28 | 19.63 | 0.8 | 80 | N/A |
| YU187754 | ChemDiv | 5465-0013 | | 7.53 | 1.15 | 5.58 | 0.98 | 49.02 | No Fit | N/A | N/A | N/A | N/A | N/A | N/A | N/A | N/A | N/A | N/A |
| YU186983 | ChemDiv | E612-0759 | | 7.71 | 3.97 | 4.2 | 0.9 | 80 | No Fit | N/A | N/A | N/A | N/A | No Fit | N/A | N/A | N/A | N/A | N/A |
| YU214474 | ChemDiv | L437-0030 | | 8.04 | 2.72 | 0.98 | 0.71 | 31.17 | No Fit | N/A | N/A | N/A | N/A | No Fit | N/A | N/A | N/A | N/A | N/A |
| YU156312 | ChemDiv | 3232-1884 | | 9.02 | 8.17 | 8.04 | 0.83 | 38.16 | No Fit | N/A | N/A | N/A | N/A | N/A | N/A | N/A | N/A | N/A | N/A |

Figure 7D

| Compound ID | Supplier | Supplier ID | Name | G151R |||||  L168R ||||| WT ||||| mean IC50 G151R / L168R |
|---|---|---|---|---|---|---|---|---|---|---|---|---|---|---|---|---|---|---|---|
| | | | | IC$_{50}$ | Hill | Minimum inhibition (%) | R$^2$ | Maximum inhibition (%) | IC$_{50}$ | Hill | Minimum inhibition (%) | R$^2$ | Maximum inhibition (%) | IC$_{50}$ | Hill | Minimum inhibition (%) | R$^2$ | Maximum inhibition (%) | |
| YU208690 | ChemDiv | G345-0648 | | 9.38 | 9.03 | 2.71 | 0.67 | 30.59 | No Fit | N/A | N/A | N/A | N/A | No Fit | N/A | N/A | N/A | N/A | N/A |
| YU224113 | Enzo | ALX-550-253 | Loperamide hydrochloride | 9.51 | 2.99 | 6.37 | 0.94 | 99.75 | No Fit | N/A | N/A | N/A | N/A | N/A | N/A | N/A | N/A | N/A | N/A |
| YU155938 | ChemDiv | 2434-0134 | | No Fit | N/A | N/A | N/A | N/A | No Fit | N/A | N/A | N/A | N/A | N/A | N/A | N/A | N/A | N/A | N/A |
| YU228017 | Toronto Research | D226800 | Decladinose Roxithromycin (Roxithromycin Impurity B) | No Fit | N/A | N/A | N/A | N/A | No Fit | N/A | N/A | N/A | N/A | No Fit | N/A | N/A | N/A | N/A | N/A |
| YU165270 | ChemDiv | D359-0544 | | No Fit | N/A | N/A | N/A | N/A | No Fit | N/A | N/A | N/A | N/A | No Fit | N/A | N/A | N/A | N/A | N/A |
| YU186982 | ChemDiv | E612-0750 | | No Fit | N/A | N/A | N/A | N/A | No Fit | N/A | N/A | N/A | N/A | No Fit | N/A | N/A | N/A | N/A | N/A |
| YU199272 | ChemDiv | G318-0226 | | No Fit | N/A | N/A | N/A | N/A | No Fit | N/A | N/A | N/A | N/A | No Fit | N/A | N/A | N/A | N/A | N/A |
| YU199273 | ChemDiv | G318-0292 | | No Fit | N/A | N/A | N/A | N/A | No Fit | N/A | N/A | N/A | N/A | No Fit | N/A | N/A | N/A | N/A | N/A |
| YU214875 | ChemDiv | L491-0661 | | No Fit | N/A | N/A | N/A | N/A | No Fit | N/A | N/A | N/A | N/A | No Fit | N/A | N/A | N/A | N/A | N/A |

Figure 7E

PLUX38, IC$_{50}$ = 0.58 µM
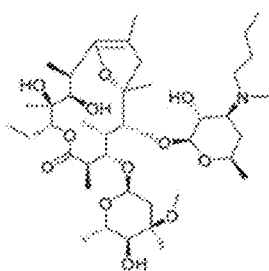
PLUX36, IC$_{50}$ = 1.03 µM
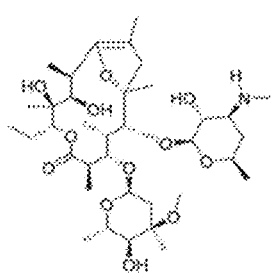
PLUX37, IC$_{50}$ = 1.11 µM
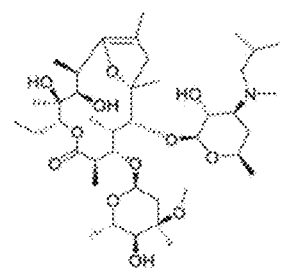
PLUX33, IC$_{50}$ = 1.83 µM
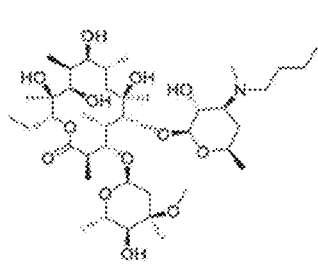
PLUX41, IC$_{50}$ = 2.07 µM
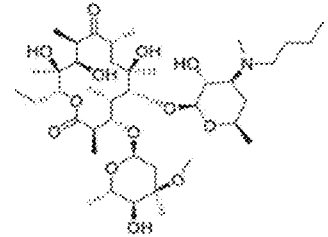
PLUX40, IC$_{50}$ = 3.18
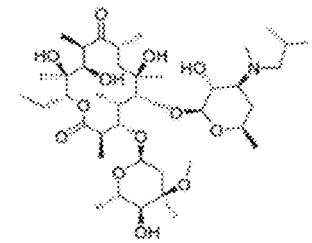
PLUX32, IC$_{50}$ = 3.62 µM
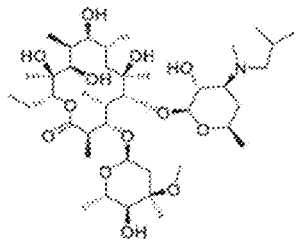
PLUX30B, IC$_{50}$ = 9.94 µM
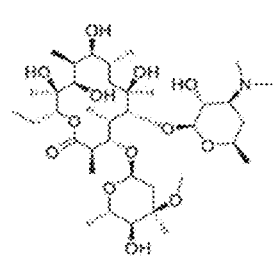
PLUX34, IC$_{50}$ = 10.24
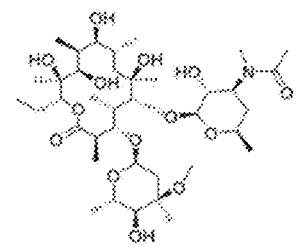
PLUX31A, IC$_{50}$ = 11.00 µM
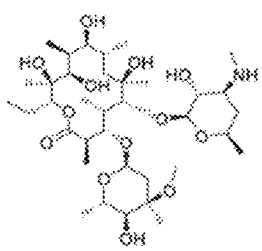
PLUX35A, IC$_{50}$ = 11.33 µM
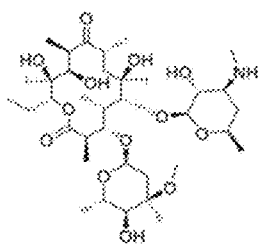
PLUX39, IC$_{50}$ = 16.84
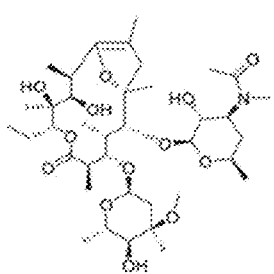
PLUX42, inactive
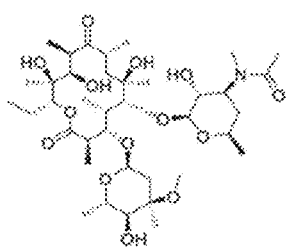
Figure 9

| Compound ID | Kirby Bauer zone diameter (mm) | G151R | | | | | L168R | | | | |
|---|---|---|---|---|---|---|---|---|---|---|---|
| | | IC50 | Hill | minimum inhibition (%) | R2 | maximum inhibition (%) | IC50 | Hill | minimum inhibition (%) | R2 | maximum inhibition (%) |
| Idremcinal (EM574) | N/A | 0.54 | 2.88 | 5.47 | 0.89 | 73.81 | 1.99 | 2.09 | -1.28 | 0.97 | 66.69 |
| PLUX38 | 0 | 0.6 | 2.4 | 6.4 | 0.9 | 89.2 | 1.2 | 1.8 | 4.4 | 0.9 | 59.0 |
| PLUX36 | 0 | 1.0 | 1.8 | 4.3 | 1.0 | 82.8 | 6.2 | 1.3 | 4.3 | 0.9 | 72.0 |
| PLUX37 | 0 | 1.1 | 2.6 | 0.9 | 0.9 | 72.2 | 3.7 | 1.9 | 2.9 | 0.9 | 85.0 |
| PLUX33 | 0 | 1.9 | 2.9 | 2.9 | 1.0 | 60.4 | 2.4 | 3.4 | 4.9 | 0.8 | 39.2 |
| PLUX41 | 15 | 2.1 | 1.9 | 3.1 | 0.9 | 75.3 | 4.7 | 1.9 | 3.7 | 0.7 | 34.5 |
| PLUX40 | 0 | 3.2 | 1.9 | 1.6 | 1.0 | 74.0 | 10.3 | 2.2 | 3.1 | 0.9 | 55.0 |
| PLUX32 | 0 | 3.62 | 1.39 | 3.63 | 0.98 | 91.44 | 5.70 | 1.82 | -0.35 | 0.99 | 67.94 |
| PLUX30B | 23 | 9.94 | 2.78 | 3.41 | 0.97 | 70.00 | 12.81 | 3.93 | -0.41 | 0.98 | 22.00 |
| PLUX34 | 0 | 10.24 | 2.19 | 1.33 | 0.76 | 12.93 | No Fit | 0.00 | 0.00 | 0.00 | 0.00 |
| PLUX31A | 13 | 11.00 | 3.00 | 3.48 | 0.93 | 30.00 | No Fit | 0.00 | 0.00 | 0.00 | 0.00 |
| PLUX35A | 18 | 11.3 | 1.5 | 0.6 | 0.9 | 38.0 | No Fit | 1.7 | 0.0 | 0.7 | 7.5 |
| PLUX39 | 0 | 16.8 | 4.0 | 2.7 | 0.7 | 60.0 | 12.9 | 5.1 | 2.4 | 0.9 | 34.0 |
| PLUX42 | 0 | No Fit | 1.1 | 0.6 | 0.5 | 25216.4 | No Fit | 1.3 | 0.2 | 0.5 | 5.2 |

Figure 10A

| Compound ID | Kirby Bauer zone diameter (mm) | G151R | | | | | L168R | | | | |
|---|---|---|---|---|---|---|---|---|---|---|---|
| | | IC$_{50}$ | Hill | minimum inhibition (%) | R2 | maximum inhibition (%) | IC$_{50}$ | Hill | minimum inhibition (%) | R2 | maximum inhibition (%) |
| Idremcinal (EM574) | N/A | 0.54 | 2.88 | 5.47 | 0.89 | 73.81 | 1.99 | 2.09 | -1.28 | 0.97 | 66.69 |
| PLUX38 | 0 | 0.58 | 2.42 | 6.36 | 0.92 | 89.18 | 1.15 | 1.83 | 4.40 | 0.91 | 58.96 |
| PLUX36 | 0 | 1.03 | 1.81 | 4.30 | 0.96 | 82.77 | 6.16 | 1.30 | 4.33 | 0.92 | 72.00 |
| PLUX37 | 0 | 1.11 | 2.60 | 0.90 | 0.94 | 72.22 | 3.72 | 1.95 | 2.90 | 0.94 | 85.03 |
| PLUX33 | 0 | 1.93 | 2.89 | 2.85 | 0.96 | 60.43 | 2.41 | 3.38 | 4.93 | 0.81 | 39.18 |
| PLUX41 | 15 | 2.07 | 1.86 | 3.07 | 0.93 | 75.31 | 4.70 | 1.89 | 3.67 | 0.74 | 34.50 |
| PLUX40 | 0 | 3.18 | 1.94 | 1.60 | 0.97 | 73.98 | 10.34 | 2.16 | 3.15 | 0.87 | 55.00 |
| PLUX32 | 0 | 3.62 | 1.39 | 3.63 | 0.98 | 91.44 | 5.70 | 1.82 | -0.35 | 0.99 | 67.94 |
| PLUX30B | 23 | 9.94 | 2.78 | 3.41 | 0.97 | 70.00 | 12.81 | 3.93 | -0.41 | 0.98 | 22.00 |
| PLUX34 | 0 | 10.24 | 2.19 | 1.33 | 0.76 | 12.93 | No Fit | 0.00 | 0.00 | 0.00 | 0.00 |
| PLUX31A | 13 | 11.00 | 3.00 | 3.48 | 0.93 | 30.00 | No Fit | 0.00 | 0.00 | 0.00 | 0.00 |
| PLUX35A | 18 | 11.33 | 1.52 | 0.56 | 0.86 | 38.00 | No Fit | 1.68 | 0.00 | 0.72 | 7.50 |
| PLUX39 | 0 | 16.84 | 3.96 | 2.72 | 0.75 | 60.00 | 12.91 | 5.14 | 2.42 | 0.91 | 34.00 |
| PLUX42 | 0 | No Fit | No Fit | No Fit | No Fit | No Fit | No Fit | No Fit | No Fit | No Fit | No Fit |

Figure 10B

SEQUENCE LISTING

<160> NUMBER OF SEQ ID NOS: 7

<210> SEQ ID NO 1
<211> LENGTH: 30
<212> TYPE: DNA
<213> ORGANISM: Artificial sequence
<220> FEATURE:
<223> OTHER INFORMATION: chemically synthesized

<400> SEQUENCE: 1
ccgaaacaac cattaggtat ggcttccgag                                              30

<210> SEQ ID NO 2
<211> LENGTH: 30
<212> TYPE: DNA
<213> ORGANISM: Artificial sequence
<220> FEATURE:
<223> OTHER INFORMATION: chemically synthesized

<400> SEQUENCE: 2
ctcggaagcc atacctaatg gttgtttcgg                                              30

<210> SEQ ID NO 3
<211> LENGTH: 27
<212> TYPE: DNA
<213> ORGANISM: Artificial sequence
<220> FEATURE:
<223> OTHER INFORMATION: chemically synthesized

<400> SEQUENCE: 3
cttccgagtc atcgcagaga agtgtcc                                                 27

<210> SEQ ID NO 4
<211> LENGTH: 27
<212> TYPE: DNA
<213> ORGANISM: Artificial sequence
<220> FEATURE:
<223> OTHER INFORMATION: chemically synthesized

<400> SEQUENCE: 4
ggacacttct ctgcgatgac tcggaag                                                 27

<210> SEQ ID NO 5
<211> LENGTH: 26
<212> TYPE: DNA
<213> ORGANISM: Artificial sequence
<220> FEATURE:
<223> OTHER INFORMATION: chemically synthesized

<400> SEQUENCE: 5
ggattatact ccgcttggtc caggcc                                                  26

<210> SEQ ID NO 6
<211> LENGTH: 26
<212> TYPE: DNA
<213> ORGANISM: Artificial sequence
<220> FEATURE:
<223> OTHER INFORMATION: chemically synthesized

<400> SEQUENCE: 6
ggcctggacc aagcggagta taatcc                                                  26

<210> SEQ ID NO 7
<211> LENGTH: 419
<212> TYPE: PRT
<213> ORGANISM: Homo sapiens

<400> SEQUENCE: 7

Met Ala Gly Asp Ser Arg Asn Ala Met Asn Gln Asp Met Glu Ile Gly
1               5                   10                  15

Val Thr Pro Trp Asp Pro Lys Lys Ile Pro Lys Gln Ala Arg Asp Tyr
            20                  25                  30

Val Pro Ile Ala Thr Asp Arg Thr Arg Leu Leu Ala Glu Gly Lys Lys
        35                  40                  45

-continued

```
Pro Arg Gln Arg Tyr Met Glu Lys Ser Gly Lys Cys Asn Val His His
    50                  55                  60
Gly Asn Val Gln Glu Thr Tyr Arg Tyr Leu Ser Asp Leu Phe Thr Thr
 65              70                  75                      80
Leu Val Asp Leu Lys Trp Arg Phe Asn Leu Leu Val Phe Thr Met Val
             85                  90                      95
Tyr Thr Val Thr Trp Leu Phe Phe Gly Phe Ile Trp Trp Leu Ile Ala
            100                 105                 110
Tyr Ile Arg Gly Asp Leu Asp His Val Gly Asp Gln Glu Trp Ile Pro
            115                 120                 125
Cys Val Glu Asn Leu Ser Gly Phe Val Ser Ala Phe Leu Phe Ser Ile
    130                 135                 140
Glu Thr Glu Thr Thr Ile Gly Tyr Gly Phe Arg Val Ile Thr Glu Lys
145                 150                 155                 160
Cys Pro Glu Gly Ile Ile Leu Leu Leu Val Gln Ala Ile Leu Gly Ser
                165                 170                 175
Ile Val Asn Ala Phe Met Val Gly Cys Met Phe Val Lys Ile Ser Gln
            180                 185                 190
Pro Lys Lys Arg Ala Glu Thr Leu Met Phe Ser Asn Asn Ala Val Ile
        195                 200                 205
Ser Met Arg Asp Glu Lys Leu Cys Leu Met Phe Arg Val Gly Asp Leu
210                 215                 220
Arg Asn Ser His Ile Val Glu Ala Ser Ile Arg Ala Lys Leu Ile Lys
225                 230                 235                 240
Ser Arg Gln Thr Lys Glu Gly Glu Phe Ile Pro Leu Asn Gln Thr Asp
                245                 250                 255
Ile Asn Val Gly Phe Asp Thr Gly Asp Asp Arg Leu Phe Leu Val Ser
                260                 265                 270
Pro Leu Ile Ile Ser His Glu Ile Asn Gln Lys Ser Pro Phe Trp Glu
        275                 280                 285
Met Ser Gln Ala Gln Leu His Gln Glu Glu Phe Glu Val Val Val Ile
290                 295                 300
Leu Glu Gly Met Val Glu Ala Thr Gly Met Thr Cys Gln Ala Arg Ser
305                 310                 315                 320
Ser Tyr Met Asp Thr Glu Val Leu Trp Gly His Arg Phe Thr Pro Val
                325                 330                 335
Leu Thr Leu Glu Lys Gly Phe Tyr Glu Val Asp Tyr Asn Thr Phe His
                340                 345                 350
Asp Thr Tyr Glu Thr Asn Thr Pro Ser Cys Cys Ala Lys Glu Leu Ala
            355                 360                 365
Glu Met Lys Arg Glu Gly Arg Leu Leu Gln Tyr Leu Pro Ser Pro Pro
370                 375                 380
Leu Leu Gly Gly Cys Ala Glu Ala Gly Leu Asp Ala Glu Ala Glu Gln
385                 390                 395                 400
Asn Glu Glu Asp Glu Pro Lys Gly Leu Gly Gly Ser Arg Glu Ala Arg
                405                 410                 415
Gly Ser Val
```

COMPOSITIONS AND METHODS FOR DIAGNOSING AND TREATING DISEASES AND DISORDERS ASSOCIATED WITH MUTANT KCNJ5

CROSS-REFERENCE TO RELATED APPLICATIONS

This application is a U.S. national phase application filed under 35 U.S.C. § 371 claiming priority to International Patent Application No. PCT/US18/33362, filed May 18, 2018, which is entitled to priority under 35 U.S.C. § 119(e) to U.S. Provisional Patent Application No. 62/507,884, filed May 18, 2017, the contents of each of which are incorporated by reference herein in their entireties.

BACKGROUND OF THE INVENTION

Aldosterone, a steroid hormone synthesized by the adrenal glomerulosa, is normally produced in two conditions: intravascular volume depletion and hyperkalemia (high plasma $K^+$ level) (Spät and Hunyady, 2004, Physiol. Rev. 84:489). Volume depletion activates the renin-angiotensin system, producing the hormone angiotensin II (AII), which signals via its G protein-coupled receptor (GPCR) in glomerulosa cells. The resting membrane potential is set by $K^+$ channel activity (Spät, 2004, Mol. Cell. Endocrinol. 217:23).

Both AII signaling and hyperkalemia cause membrane depolarization and activation of voltage-gated $Ca^{2+}$ channels. Increased intracellular $Ca^{2+}$ provides the normal signal for aldosterone production, and sustained increases lead to glomerulosa cell proliferation (Spät and Hunyady, 2004, Physiol. Rev. 84:489; McEwan et al., 1996, Am. J. Physiol. 271, E192; Pawlikowski et al., 2001, Endocr. Regul. 35:139; Tanabe et al., 1998, J. Endocrinol. Invest. 21:668). AII also causes increased inositol 1,4,5-trisphosphate (IP3) and transient $Ca^{2+}$ release from intracellular stores. Aldosterone signaling in the kidney increases electrogenic $Na^+$ reabsorption, defending intravascular volume, and also increases $K^+$ secretion.

In primary aldosteronism, the adrenal gland constitutively produces aldosterone in the absence of AII or hyperkalemia, resulting in hypertension and variable hypokalemia (low plasma $K^+$ level). Primary aldosteronism is found in approximately 10% of patients referred for evaluation of hypertension. A third or more of these have aldosterone-producing adenoma (APA, also known as Conn's syndrome) of the adrenal cortex (Rossi et al., 2006, J. Am. Coll. Cardiol. 48:2293). Of the remainder, a small fraction have mutations that cause constitutive expression of aldosterone synthase (Lifton et al., 1992, Nature 355:262), and the rest are classified as idiopathic.

Adrenal aldosterone-producing adenomas (APAs) are benign tumors of the adrenal gland that constitutively produce aldosterone and can cause severe hypertension. Either of two recurrent somatic mutations (G151R and L168R) in the adrenal potassium channel KCNJ5 ($KCNJ5^{MUT}$) cause ~63% and ~35% of APAs in people of Asian and European ancestry, respectively (Lenzini et al., 2015, J. Clin. Endocrinol. Metab.; Choi et al., 2011, Science 331:768-772). These mutations alter channel selectivity to allow $Na^+$ conductance. The resulting membrane depolarization causes calcium influx, aldosterone production and proliferation. Because APA diagnosis requires a technically difficult, invasive procedure, patients often remain undiagnosed and poorly treated.

APAs are typically solitary, well circumscribed, and diagnosed between ages 30 and 70 (V. Kumar. A. K. Abbas, N. Fausto, J. C. Aster, Eds., in Robbins and Cotran Pathologic Basis of Disease (Saunders, Philadelphia, ed. 8, 2009), chap. 24). They come to medical attention due to new or worsening hypertension, often with hypokalemia. Aldosterone is elevated while renin levels are suppressed (reflected in a high aldosterone:renin ratio), and a characteristic adrenal mass can be seen on computed tomography (CT). Adrenal vein sampling demonstrates predominant aldosterone secretion from the gland harboring the tumor. APAs virtually always remain benign, without local invasion or distant metastasis (Ghose et al., 1999, Ann. Intern. Med. 131:105). Surgical removal ameliorates or cures hypertension in the large majority of patients (Calvo-Romero and Ramos-Salado, 2000, Postgrad. Med. J. 76:160). The mechanisms responsible for neoplasia and cell-autonomous aldosterone production are unknown.

Hypertension affects more than one billion people and is a major risk factor for heart attack, stroke, and congestive heart failure, contributing to more than nine million deaths worldwide each year (Lim et al., 2012, Lancet 380:2224-2260). Among patients referred to hypertension clinics, adrenal gland tumors that constitutively secrete the steroid hormone aldosterone are found in about 5% (Rossi et al., 2006, J. Am. Coll. Cardiol. 48:2293-2300). These tumors are virtually always benign adenomas, and their surgical removal is commonly curative, motivating efforts to make a timely and accurate diagnosis. APA diagnosis is typically based upon the finding of hypertension, elevated plasma aldosterone level with suppressed plasma renin activity (indicating autonomous adrenal aldosterone production), evidence from imaging of an adrenal tumor, and invasive bilateral adrenal vein sampling (AVS) showing increased aldosterone levels in the adrenal vein ipsilateral to the tumor.

Unfortunately, AVS is an invasive and technically challenging procedure that is only available in a limited number of tertiary care centers. As a result, many patients are not diagnosed and do not receive optimal treatment. New pharmacologic strategies for the diagnosis and treatment of APAs are necessary.

By exome sequencing of APAs (Choi et al., 2009, Proc. Natl. Acad. Sci. U.S.A. 106:19096-19101) and matched normal tissue, it has been demonstrated that either of two somatic missense mutations in the potassium channel KCNJ5 commonly causes APAs (Choi et al., 2011, Science 331:768-772). Large multicenter studies have confirmed these findings and have shown that these mutations (G151R and L168R) account for about 35% of APAs in people of European ancestry (Lenzini et al., 2015, J. Clin. Endocrinol. Metab.; Akerstrom et al., 2012, PLoS ONE 7:e41926; Fernandes-Rosa et al., 2014, Hypertension 64:34-361), and about 63% of people of Asian ancestry (Lenzini et al., 2015, J. Clin. Endocrinol. Metab.; Zheng et al., 2015, Hypertension 65:622-628; Hong et al., 2016, PLoS ONE 11:e0147590; Kitamoto et al., 2015, J. Atheroscler. Thromb. 22:191-200). There is also a striking gender dimorphism in European cohorts and one Asian cohort, with 50-60% of women but only about 20% of men with APAs having KCNJ5 mutations (Akerstrom et al., 2012, PLoS ONE 7:e41926; Boulkroun et al., 2012, Hyptertension 59:592-598). A small number of additional KCNJ5 mutations are very rare causes of APAs (Akerstrom et al., 2012, PLoS ONE 7:e41926; Zheng et al., 2015, Hypertension 65:622-628; Boulkroun et al., 2012, Hyptertension 59:592-598). $KCNJ5^{G151R}$ and $KCNJ5^{L168R}$ both modify the channel's selectivity filter, which normally confers high selectivity of the channel for K+ conductance; the mutant channel loses selectivity and shows similar conduction of K+ and Na+2. This results in Na+ influx, leading to membrane depolarization, activation of voltage-gated $Ca^{2+}$ channels and $Ca^{2+}$ influx[2]. Increased intracellular $Ca^{2+}$ is the signal for both cellular proliferation and aldosterone production in adrenal glomerulosa cells (Spat and Hunyady, 2004, Physiol. Rev. 84:489-539), thereby accounting for the cardinal features of APAs. Evidence that these single mutations are sufficient for tumor formation comes from the finding of identical or related germline KCNJ5 mutations in a rare Mendelian form of early-onset and severe hypertension due to primary aldosteronism with massive adrenal hyperplasia (Choi et al., 2011, Science 331:768-772; Scholl et al., 2012, Proc. Natl. Acad. Sci. U.S.A. 109:2533-2538). Additionally, APAs harboring KCNJ5 mutations have very few additional protein-altering somatic mutations (only about three per tumor) that virtually never alter other genes involved in cell proliferation or aldosterone biosynthetic pathways.

Screening studies of hypertensive patient populations have revealed primary aldosteronism as the most common cause of secondary hypertension, and together with recognition of the association with severe cardiovascular complications, have produced a renewed focus on the syndrome of primary aldosteronism (Young, 2007, Clin. Endocrinol. (Oxf) 66:607-618; Gordon et al., 1992, Lancet 340:159-161; Rossi et al., 2006, J. Am. Coll. Cardiol. 48:2293-2300; Rossi et al., 2008, J. Hypertens. 26:613-621; Rossi, 2011, Endocrinol. Metab. Clin. North Am. 40:313-332; Stowasser and Gordon, 2003, Primary aldosteronism. Best Pract. Res. Clin. Endocrinol. Metab. 17:591-605). This has led to marked improvement in guidelines for case detection, diagnosis and treatment (Funder et al., 2008, J. Clin. Endocrinol. Metab. 93:3266-3281).

Case detection has been recommended in all patients with hypertension, and should be based on PAC/PRA (or PRC) ratio (with laboratory dependent cut-off values), and confirmation of the diagnosis by either of various suppression tests (oral sodium loading, saline infusion, captopril test, and fludrocortisone suppression tests) (Gordon et al., 1992, Lancet 340:159-161; Rossi, 2011, Endocrinol. Metab. Clin. North Am. 40:313-332; Funder et al., 2008, J. Clin. Endocrinol. Metab. 93:3266-3281; Westerdahl et al., 2009, Scand. J. Clin. Lab. Invest. 69:234-241). The combination of adrenal CT and adrenal vein sampling is recommended for identification of unilateral lesions, which are potentially curable by surgery, and for appropriate lateralization diagnosis prior to operation (Funder et al., 2008, J Clin Endocrinol Metab. 93:3266-3281). CT identification of a unilateral adrenal lesion in younger patients (<40 years) with primary aldosteronism may represent an appropriate indication for surgery, although demonstration of lateralization of aldosterone secretion is otherwise claimed to be essential to maximize benefits of surgical intervention (Young, 2007, Clin. Endocrinol. (Oxf) 66:607-618; Funder et al., 2008, J. Clin. Endocrinol. Metab. 93:3266-3281; Mathur et al., 2010, J. Am. Coll. Surg. 211:384-390). Using whole-exome sequencing, two somatic gain-of-function mutations in the potassium channel KCNJ5 were identified as the cause of ~40-50% of APAs (Choi et al., 2011, Science 331:768-772).

There is great need for a new non-invasive method of diagnosing APA. The diagnosis and surgical management of APA is currently confounded by the need for an invasive diagnostic procedure, i.e., adrenal venous sampling. In addition to being invasive, this procedure is not widely available, and the vast majority of patients do not get definitive treatment because of a lack of diagnosis. Thus, the availability of a compound acting as a specific inhibitor of aldosterone production and cellular proliferation would thus provide substantial diagnostic and therapeutic benefit. The present invention fulfills these needs.

SUMMARY OF THE INVENTION

The invention includes a method of treating a subject diagnosed with an adrenal disease or disorder associated with mutant KCNJ5. The method comprises measuring at least one sign or symptom of the adrenal disorder in the subject. The method further comprises administering a mutant KNCJ5 inhibitor compound to the subject. The method further comprises measuring the at least one sign or symptom of the adrenal disorder in the subject after administering a mutant KNCJ5 inhibitor compound to the subject. The method further comprises diagnosing the subject with an adrenal disease or disorder associated with mutant KCNJ5 based upon the detected sign or symptom, and administering a treatment to the subject to treat the adrenal disease or disorder associated with mutant KCNJ5. According to the method, when the at least one sign or symptom of the adrenal disorder is improved after administration of the mutant KNCJ5 inhibitor compound, the subject is diagnosed as having an adrenal disease or disorder associated with mutant KCNJ5.

In one embodiment, the mutant KCNJ5 has at least one mutation selected from the group consisting of: G151X, L168X, T158X and E145X. In another embodiment, the mutant KCNJ5 has at least one mutation selected from the group consisting of: G151R, L168R, T158A and E145Q. In yet another embodiment, the subject is human.

In one embodiment, the treatment regimen is selected from the group consisting of surgery, radiation, chemotherapy, administration of a drug, inhibitor, or medicine, or combinations thereof.

In one embodiment, the adrenal disease or disorder is at least one disease or disorder selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

In one embodiment, the mutant KCNJ5 inhibitor compound, or a salt or solvate thereof, is at least one compound selected from the group consisting of: erythromycin; erythromycin A oxime; pseudo erythromycin A enol ether; erythromycin B; erythromycin C; anhydroerythromycin A; mitemcinal; clarithromycin; roxithromycin; roxithromycin D7; dirithromycin; cethromycin; spiramycin; ansamycin; oleandomycin; carbomycin; tylosin; idremcinal; a compound selected from the group consisting of:

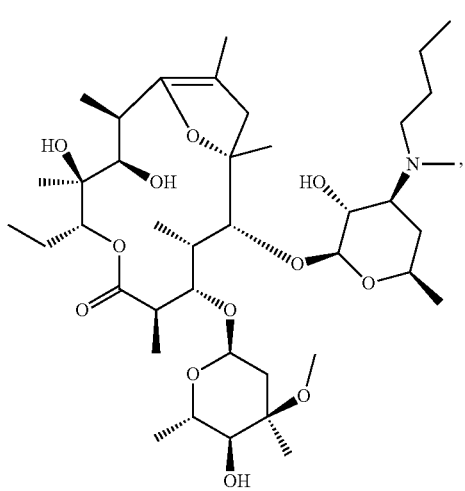
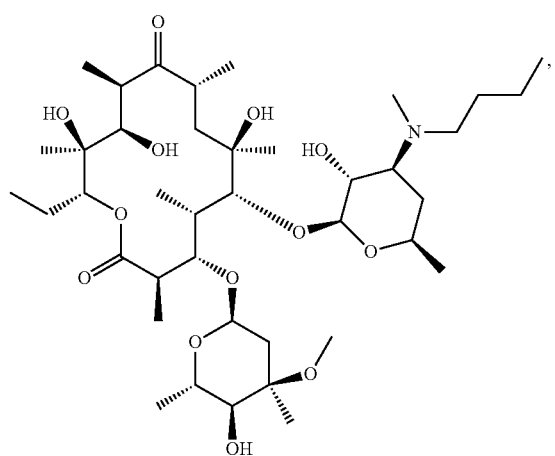
-continued
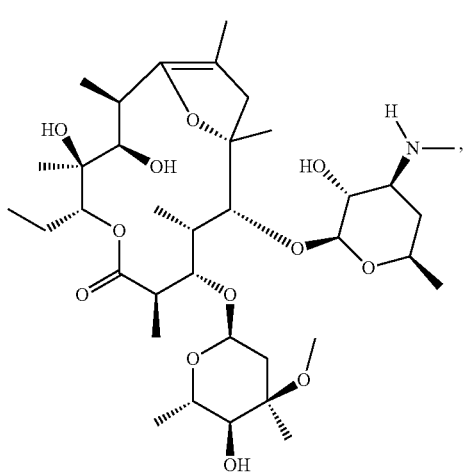
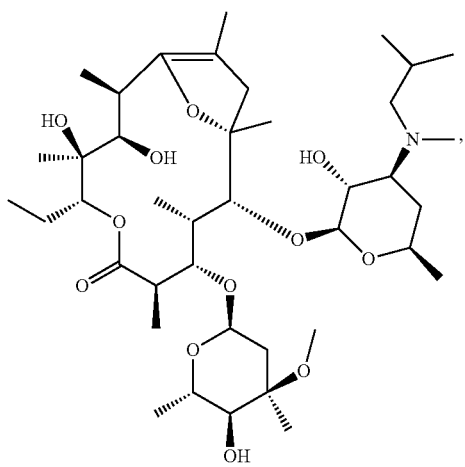
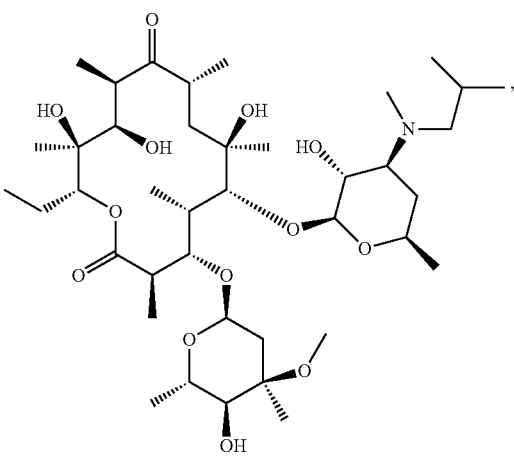

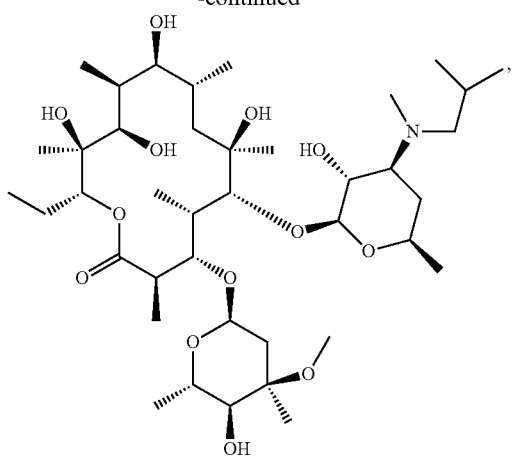
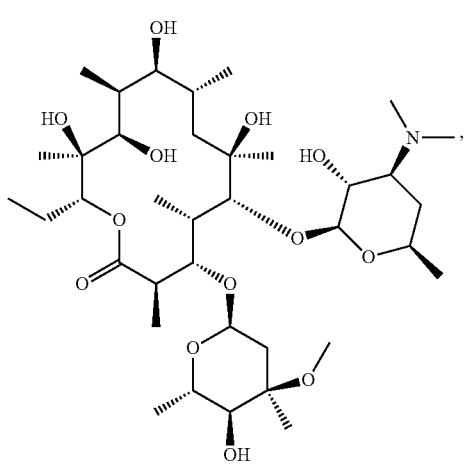
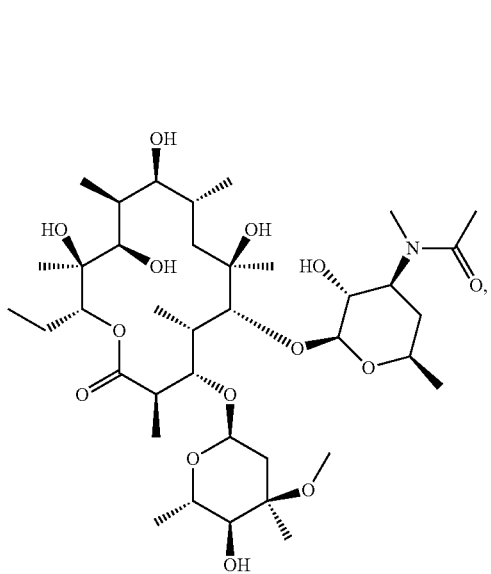
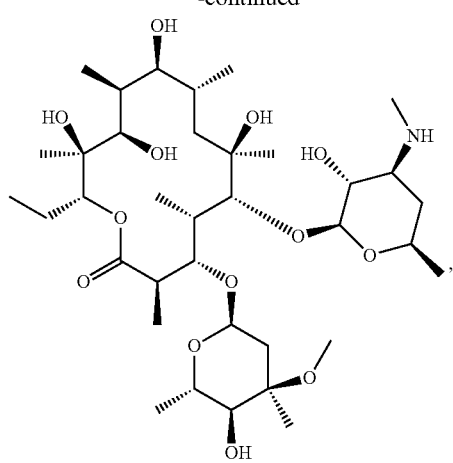
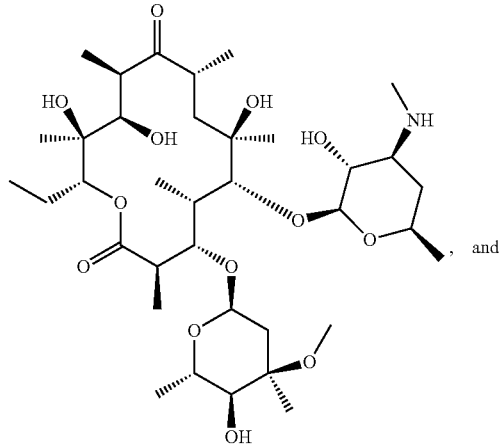
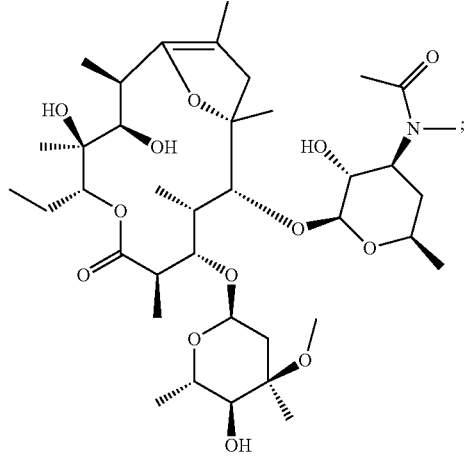
and a compound of formula (I):
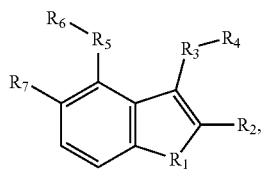

wherein:
R₁ is NH, N(C₁-C₆ alkyl), O or S;
R₂ is H or C₁-C₆ alkyl;
R₃ is C(O)NH or S(O)₂NH, wherein the N atom of R₃ is bound to R₄;
R₄ is aryl or heteroaryl;
R₅ is C(O) or CH₂;
R₆ is a N-linked heterocycle, and
R₇ is H, C₁-C₃ alkyl, OH, C₁-C₃ alkoxy, F, Cl, Br, I, CF₃, C₁-C₃ haloalkyl, NO₂, COOH and NH₂; wherein:
  the alkyl and N-linked heterocycle groups are independently and optionally substituted with 1-4 substituents selected from the group consisting of C₁-C₃ alkyl, OH, C₁-C₃ alkoxy, F, Cl, Br and I,
  the aryl and heteroaryl groups are independently and optionally substituted with 1-3 substituents selected from the group consisting of C₁-C₃ alkyl, OH, C₁-C₃ alkoxy, F, Cl, Br, I, CF₃, C₁-C₃ haloalkyl, NO₂, COOH and NH₂.

In one embodiment, the mutant KCNJ5 inhibitor compound, or a salt or solvate thereof, is at least one compound selected from the group consisting of: erythromycin; erythromycin A oxime; clarithromycin; roxithromycin; 5-hydroxy-N-(4-methoxyphenyl)-2-methyl-4-((1,3,3-trimethyl-6-azabicyclo[3.2.1]octan-6-yl)methyl)benzofuran-3-carboxamide; 5-hydroxy-2-methyl-N-phenyl-4-((1,3,3-trimethyl-6-azabicyclo[3.2.1]octan-6-yl)methyl)benzofuran-3-carboxamide; and 5-hydroxy-2-methyl-4-(piperidin-1-ylmethyl)-N-(3-(trifluoromethyl)phenyl)benzofuran-3-carboxamide.

The invention also includes a method of treating an adrenal disease or disorder in a subject in need thereof. The method comprises: administering to the subject a therapeutically effective amount of a mutant KCNJ5 inhibitor compound, wherein the subject has been diagnosed as having an adrenal disease or disorder, and wherein after the mutant KCNJ5 inhibitor compound is administered to the subject, the adrenal disease or disorder is treated.

In one embodiment, the mutant KCNJ5 inhibitor compound, is at least one compound selected from the group consisting of: erythromycin; erythromycin A oxime; pseudo erythromycin A enol ether; erythromycin B; erythromycin C; anhydroerythromycin A; mitemcinal; clarithromycin; roxithromycin; roxithromycin D7; dirithromycin; cethromycin; spiramycin; ansamycin; oleandomycin; carbomycin; tylosin; idremcinal; a compound selected from the group consisting of:

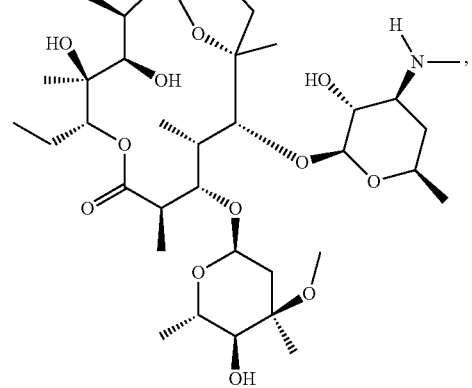

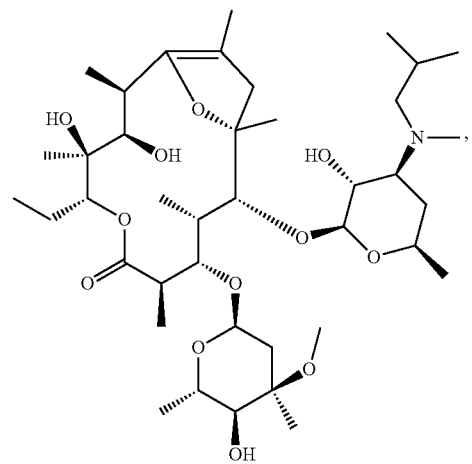

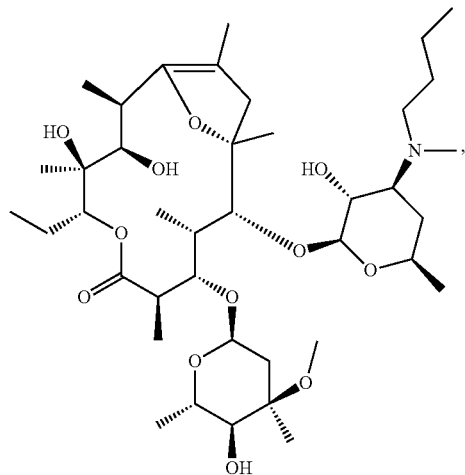

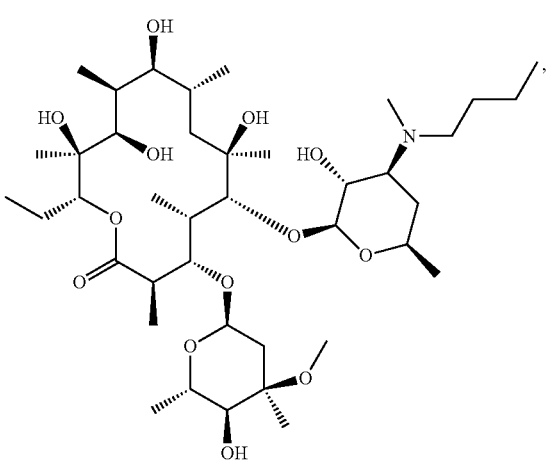

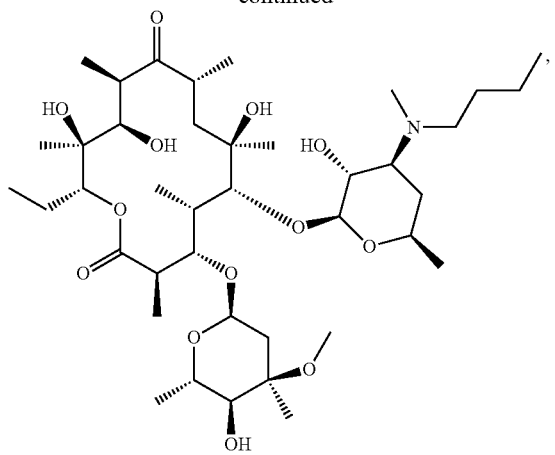
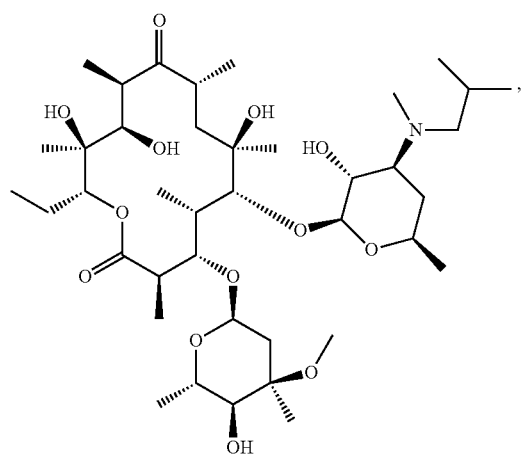
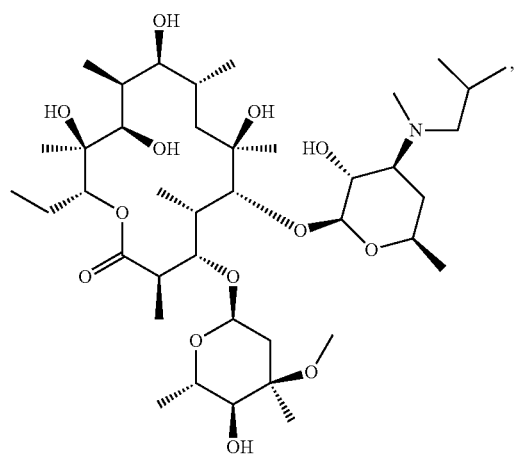
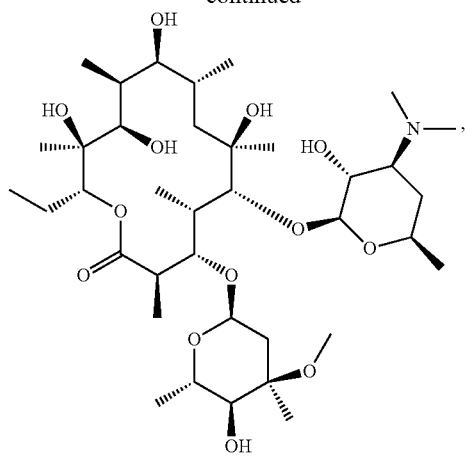
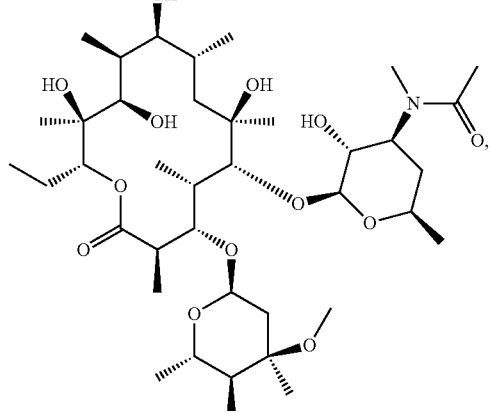
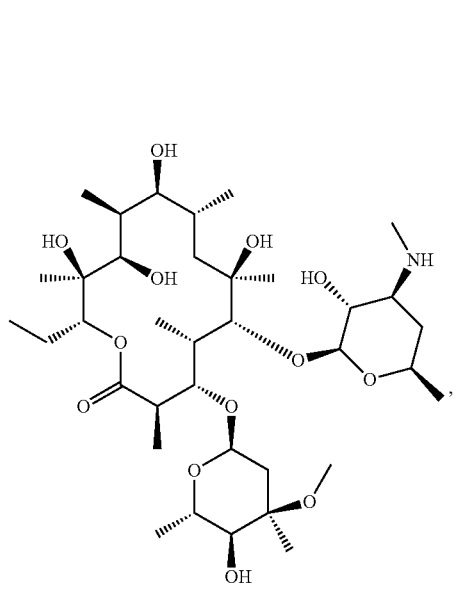

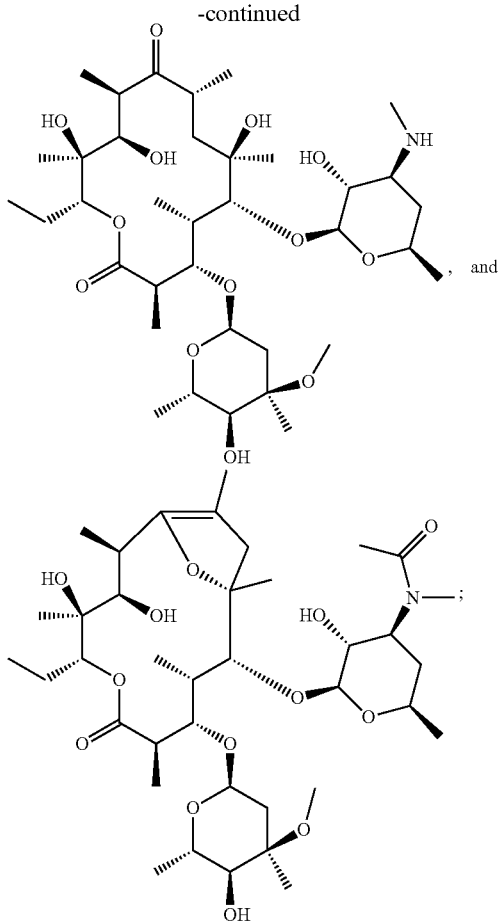

and a compound of formula (I):

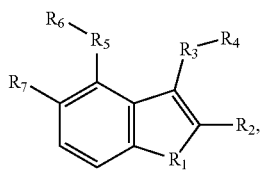

wherein:
R₁ is NH, N(C₁-C₆ alkyl), O or S;
R₂ is H or C₁-C₆ alkyl;
R₃ is C(O)NH or S(O)₂NH, wherein the N atom of R₃ is bound to R₄;
R₄ is aryl or heteroaryl;
R₅ is C(O) or CH₂;
R₆ is a N-linked heterocycle, and
R₇ is H, C₁-C₃ alkyl, OH, C₁-C₃ alkoxy, F, Cl, Br, I, CF₃, C₁-C₃ haloalkyl, NO₂, COOH and NH₂; wherein:
the alkyl and N-linked heterocycle groups are independently and optionally substituted with 1-4 substituents selected from the group consisting of C₁-C₃ alkyl, OH, C₁-C₃ alkoxy, F, Cl, Br and I,
the aryl and heteroaryl groups are independently and optionally substituted with 1-3 substituents selected from the group consisting of C₁-C₃ alkyl, OH, C₁-C₃ alkoxy, F, Cl, Br, I, CF₃, C₁-C₃ haloalkyl, NO₂, COOH and NH₂.

In one embodiment, the mutant KCNJ5 inhibitor compound, or a salt or solvate thereof, is at least one compound selected from the group consisting of: erythromycin; erythromycin A oxime; clarithromycin; roxithromycin; idremcinal; 5-hydroxy-N-(4-methoxyphenyl)-2-methyl-4-(1,3,3-trimethyl-6-azabicyclo[3.2.1]octan-6-yl)methyl)benzofuran-3-carboxamide; 5-hydroxy-2-methyl-N-phenyl-4-((1,3,3-trimethyl-6-azabicyclo[3.2.1]octan-6-yl)methyl)benzofuran-3-carboxamide; and 5-hydroxy-2-methyl-4-(piperidin-1-ylmethyl)-N-(3-(trifluoromethyl)phenyl) benzofuran-3-carboxamide; and a compound selected from the group consisting of:

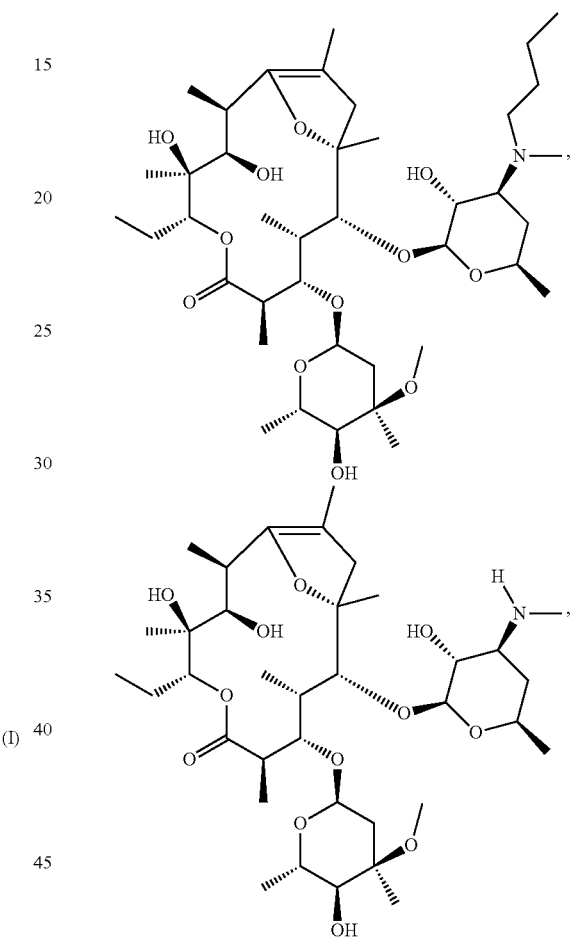

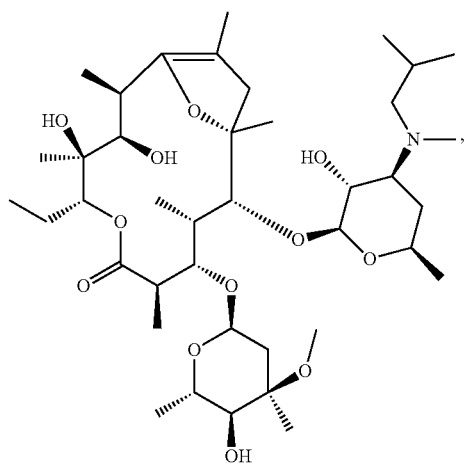

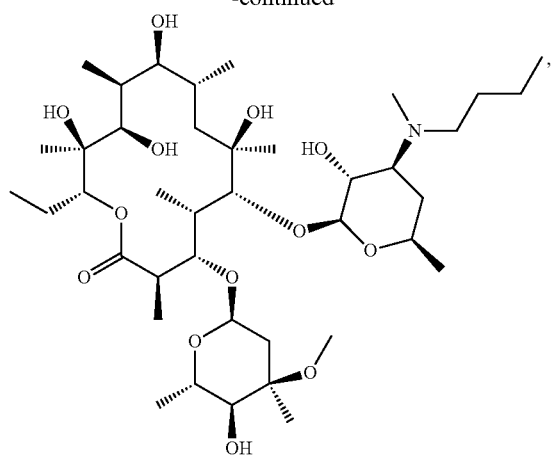
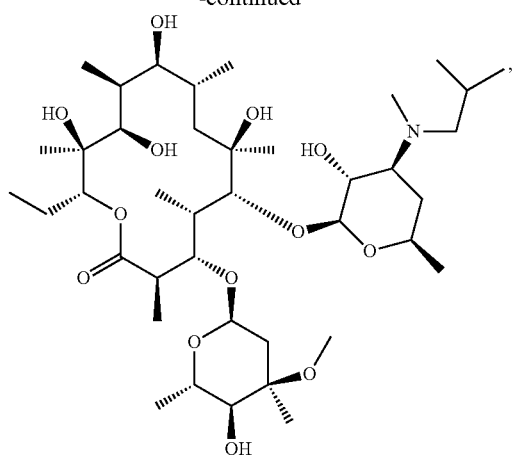
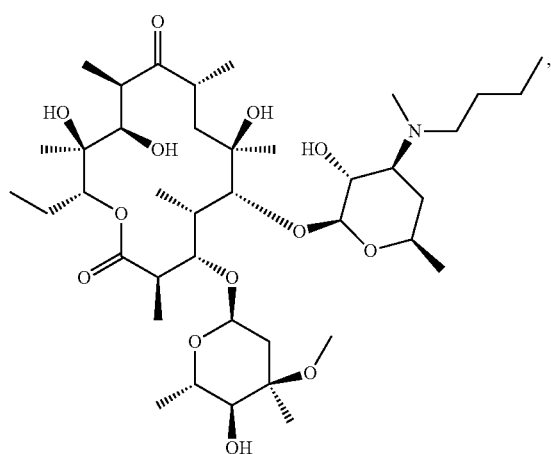
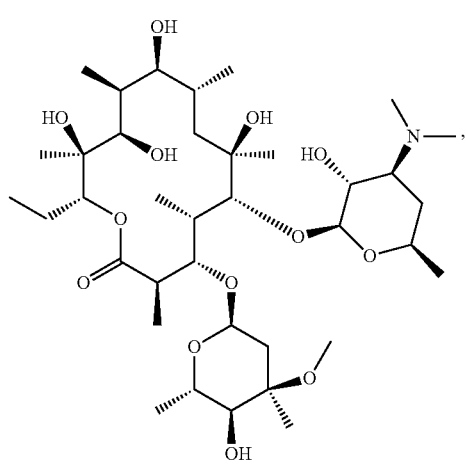
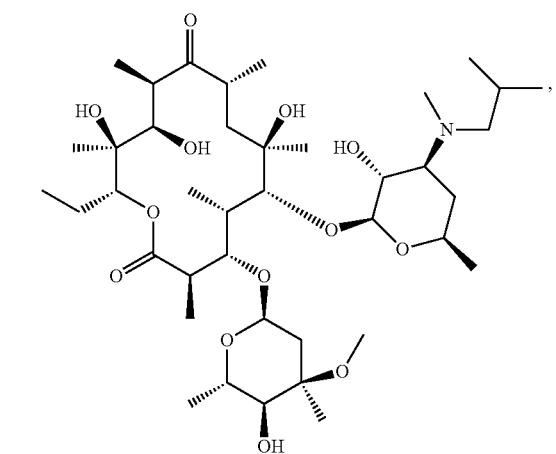
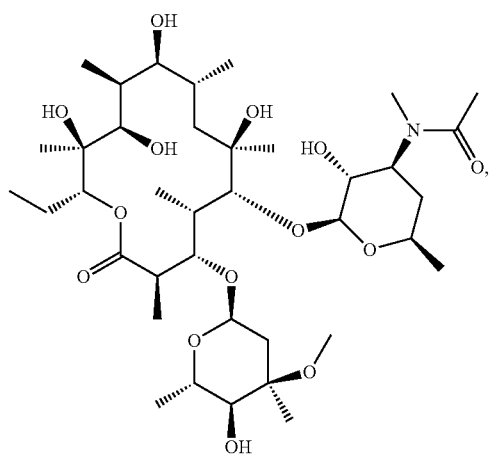

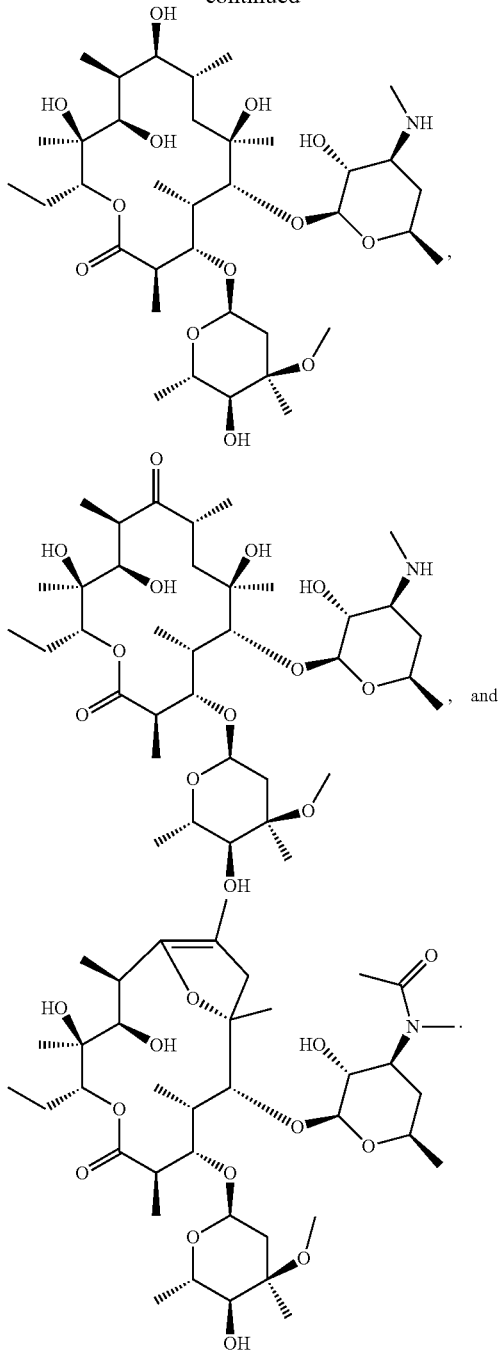

In one embodiment, the subject has at least one mutation in KCNJ5. In another embodiment, the subject has at least one mutation in KCNJ5 in or near the KCNJ5 selectivity filter. In yet another embodiment, the subject has at least one mutation in KCNJ5, wherein the at least one mutation is at amino acid residue position from about 140 to about 180 relative to SEQ ID NO:7. In yet another embodiment, the at least one mutation is at least one selected from the group consisting of: G151X, L168X, T158X and E145X. In yet another embodiment, the at least one mutation is at least one selected from the group consisting of: G151R, L168R, T158A and E145Q. In yet another embodiment, the subject is human. In yet another embodiment, the disease or disorder is an adrenal disease or disorder. In yet another embodiment, the adrenal disease or disorder is at least one disease or disorder selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A-2B, depicts the results of exemplary experiments assessing survival of 293T cells transfected with WT or mutant eGFP-tagged KCNJ5 channels. The percentage of eGFP-positive cells was measured at indicated times by flow cytometry (20,000 events counted per data point). Cells carrying mutant channels die from excess sodium influx in standard medium (FIG. 2A), while low sodium medium increases survival (FIG. 2B).

FIG. 5 depicts the structures of various macrolides. The location of desosamine and cladinose are indicated for the roxithromycin structure. Values of $IC_{50}$ for $KCNJ5^{G151R}$ are given for active compounds. See Table 2 for detailed screen results.

FIG. 7, comprising FIGS. 7A-7E, depicts experimental data demonstrating $KCNJ5^{G151R}$, $KCNJ5^{L168R}$ and $KCNJ5^{WT}$ inhibition characteristics of 98 compounds tested in dose-response assays. Inhibition data were obtained at 10 μM, 3.33, 1.11 μM and 0 μM compound concentration (see methods) for $KCNJ5^{G151R}$, $KCNJ5^{L168R}$ and $KCNJ5^{WT}$. $IC_{50}$, half maximal inhibitory concentration; Hill, Hill coefficient; $LD_{50}$, median lethal dose. Data are sorted by mean $IC_{50}$ in G151R and L168R, then by $IC_{50}$ in L168R, then by $IC_{50}$ in G151R.

FIGS. 8A-8C, depicts a series of dose response curves of lead macrolide compounds. Dose response curves of roxithromycin (FIG. 8A), clarithromycin (FIG. 8B) and idremcinal (FIG. 8C) are depicted. Compounds were tested at 20, 10, 5, 2.5, 1.25, 0.625, 0.3125, 0.1563, 0.0781 and 0.0391 μM concentrations. Data were fit with a four-parameter non-linear regression of log-dose versus response. Shown are mean values of 3 experiments. See Table 2 for inhibition data. All three compounds are specific inhibitors of mutant KCNJ5 channels.

FIG. 9 depicts the structures of synthesized compounds of the present invention. Values of $IC_{50}$ for $KCNJ5^{G151R}$ are given for active compounds. See FIG. 10 for detailed screen results.

FIG. 10, comprising FIGS. 10A-10B, depicts tables of experimental data demonstrating $KCNJ5^{G151R}$ and $^{L168R}$ inhibition characteristics of idremcinal and synthesized macrolide derivatives. Synthesized macrolide derivatives were tested as in FIG. 7. No $KCNJ5^{WT}$ inhibition was observed for any of the compounds shown.

FIGS. 11A-11B, depicts experimental data demonstrating that roxithromycin inhibits KCNJ3/$KCNJ5^{MUT}$-induced Na$^+$ current and $KCNJ5^{MUT}$-induced aldosterone synthase expression. FIG. 11A is a series of graphs depicting cation currents measured with the perforated whole cell recording. Current-voltage plots of KCNJ3/$KCNJ5^{G151R}$, $^{L168R}$ and $^{WT}$ heterotetramers before and 10 minutes after addition of 20 μM roxithromycin and 1 mM $BaCl_2$, are shown. Errors represent standard error of the mean, N=3 to 6. FIG. 11B is a graph depicting experimental data demonstrating that H295R cells were transfected with $KCNJ5^{WT}$ (WT), $KCNJ5^{G151R}$ (G151R) and $KCNJ5^{L168R}$ (L168R). Cells were treated with the indicated concentrations of roxithromycin or with vehicle control for 18 hours. N=5 for all groups. , $p \le 0.01$; *, $p \le 0.001$; ns, $p > 0.05$ (Student's t-test). Error bars represent standard error of the mean.

FIGS. 12A-12D, depicts experimental data demonstrating the inhibition of KCNJ5 homotetramers by roxithromycin. Cation currents were measured with the perforated whole cell recording technique (140 mM NaCl/5 mM KCl bath solution, 140 mM KCl pipette solution for $KCNJ5^{G151R}$; 140 mM NaCl/5 mM KCl bath solution, 140 mM KCl, 1.8 mM $MgCl_2$ pipette solution for $KCNJ5^{L168R}$; 140 mM KCl bath and pipette solution for $KCNJ5^{WT}$). Current-voltage plots of KCNJ3/$KCNJ5^{G151R}$ (FIG. 12A), $^{L168R}$ (FIG. 12B) and $^{WT}$ (FIG. 12C) heterotetramers before and 10 minutes after addition of 20 μM Roxithromycin and 1 mM $BaCl_2$, are shown. Errors represent standard error of the mean, N=3 to 6. FIG. 12D is a graph depicting experimental data demonstrating dose-dependent inhibition of $KCNJ5^{G151R}$ by increasing roxithromycin concentrations at −80 mV. In contrast, WT currents are not inhibited. Data was normalized to current before addition of roxithromycin, and % inhibition was calculated.

DETAILED DESCRIPTION OF THE INVENTION

Figure 1:
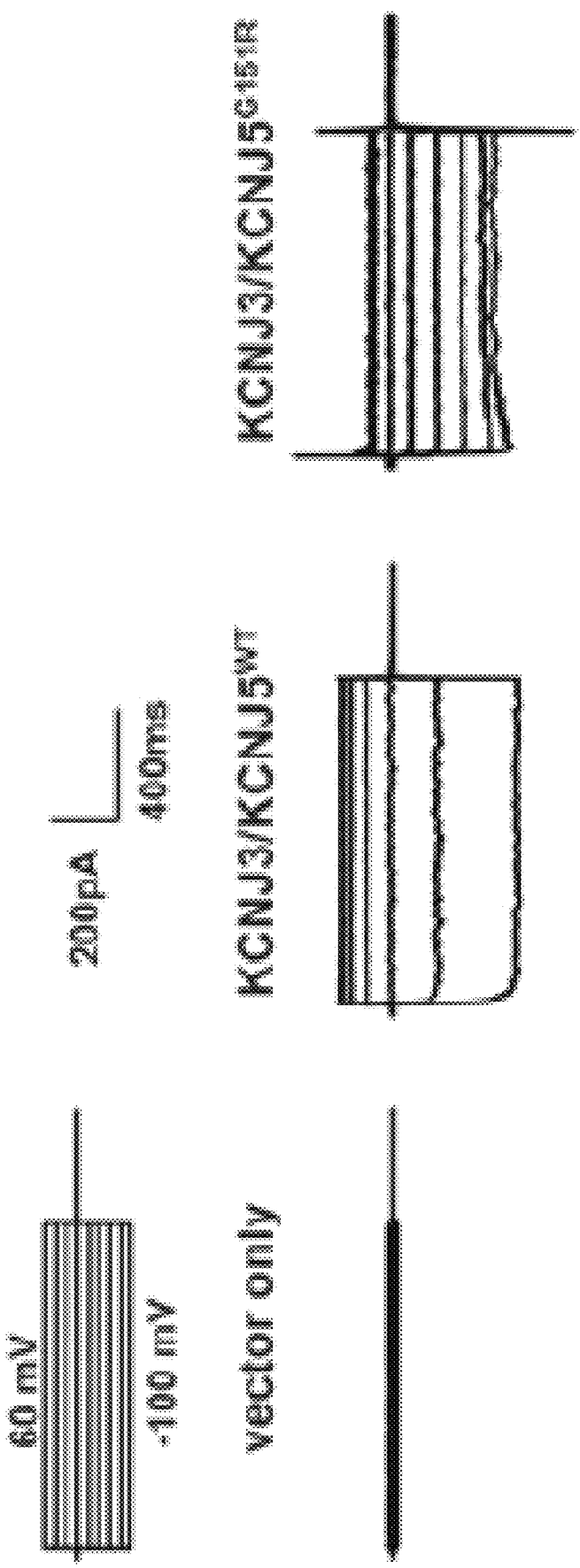
FIG. 1 depicts the results of exemplary electrophysiology experiments of wild-type (WT) and mutant KCNJ5. Representative whole cell recordings of 293T cells transfected with vector or KCNJ3+WT or mutant KCNJ5, using the indicated voltage protocol. Extracellular: 140 mM NaCl, 5 mM KCl, 1.8 mM $MgCl_2$, 1.8 mM $CaCl_2$), 10 mM HEPES, pH 7.4; intracellular: 140 mM KCl, 4 mM $MgCl_2$, 1 mM $CaCl_2$), 1 mM EGTA, 5 mM HEPES, pH 7.4.

The present invention relates to compositions and methods for diagnosing and treating adrenal diseases or disorders associated with mutations in KCNJ5. In one embodiment, the mutation is a somatic mutation. In another embodiment, the mutation is an inherited mutation. In yet another embodiment, the mutation is located in or near the selectivity filter of KCNJ5.

The invention includes a composition comprising a modulator of mutant KCNJ5 for diagnosing or for treating subjects having a mutant KCNJ5. The invention includes a method of diagnosing an adrenal disease or disorder associated with mutant KCNJ5 and a method of treating an adrenal disease or disorder associated with mutant KCNJ5.

Examples of adrenal diseases and disorders amenable to the compositions and methods of the invention include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

Examples of pathologies associated with an adrenal disease or disorder amendable to the compositions and methods of the invention include, but are not limited to, hypernatremia, hypokalemia, hypocalcemia, hypomagnesemia, neoplasia, polyuria, polydipsia, heart disease, renal disease and stroke. In one embodiment, the primary aldosteronism is associated with APA.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human. As used herein, to "alleviate" a disease or disorder means reducing the frequency or severity of at least one sign or symptom of a disease or disorder, such as an adrenal disease or disorder. Examples of adrenal diseases and disorders include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension and virilization.

As used herein, the terms "therapy" or "therapeutic regimen" refer to those medical steps taken to alleviate or alter a disorder or disease state, e.g., a course of treatment intended to reduce or eliminate the affects or symptoms of a disease using pharmacological, surgical, dietary and/or other techniques. A therapeutic regimen may include a prescribed dosage of one or more drugs or surgery. Therapies will most often be beneficial and reduce the disorder or disease state but in many instances the effect of a therapy will have non-desirable or side-effects. The effect of therapy will also be impacted by the physiological state of the host, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "diagnosis" refers to the determination of the nature of a case of disease or disorder. In some embodiments of the present invention, methods for making a diagnosis are provided which permit determination of a particular mutation associated with an adrenal disease or disorder. Examples of adrenal diseases and disorders include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants," "polymorphisms," or "mutations."

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "applicator," as the term is used herein, is meant any device including, but not limited to, a hypodermic syringe, a pipette, an iontophoresis device, a patch, and the like, for administering the compositions of the invention to a subject.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the term "control nucleic acid" is meant to refer to a nucleic acid (e.g., RNA, DNA) that does not come from a subject known to have, or suspected to have, a mutation in the gene of interest (e.g., for a control subject). For example, the control can be a wild type nucleic acid sequence which does not contain a variation in its nucleic acid sequence. Also, as used herein, a control nucleic acid can be a fragment or portion of gene that does not include the defect/variation that is the mutation of interest (that is, the mutation to be detected in an assay). As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

A "genome" is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phso-phoribosyltransferase (HRPT), 28S, and 18S rRNAs and the like.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." A single DNA molecule with internal complementarity could assume a variety of secondary structures including loops, kinks or, for long stretches of base pairs, coils.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

Assays for amplification of the known sequence are also disclosed. For example primers for PCR may be designed to amplify regions of the sequence. For RNA, a first reverse transcriptase step may be used to generate double stranded DNA from the single stranded RNA. The array may be designed to detect sequences from an entire genome; or one or more regions of a genome, for example, selected regions of a genome such as those coding for a protein or RNA of interest; or a conserved region from multiple genomes; or multiple genomes, Arrays and methods of genetic analysis using arrays is described in Cutler, et al., 2001, Genome Res. 11(11): 1913-1925 and Warrington, et al., 2002, Hum Mutat 19:402-409 and in U.S. Patent Pub No 20030124539, each of which is incorporated herein by reference in its entirety.

By the term "modulating," as used herein, is meant mediating a detectable increase or decrease in the level or activity of a molecule, or in the response in a subject, compared with the level or activity of a molecule, or in the response in the subject, in the absence of a treatment or compound, and/or compared with the level or activity of an otherwise identical but untreated molecule or of a response in an otherwise identical but untreated subject. The term encompasses perturbing and/or affecting a native signal or response thereby mediating a beneficial therapeutic response in a subject, preferably, a human.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or polypeptide comprising a mutation.

"Neoplasia" as used herein, refers to the abnormal proliferation of benign or malignant cells. The growth of neoplastic cells exceeds and/or is not coordinated with that of the normal tissues around it.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

As used herein, the term "polymerase chain reaction" ("PCR") refers to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

The term "perfect match," "match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe." The term "mismatch," "mismatch control" or "mismatch probe" refers to a nucleic acid whose sequence is not perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds.

As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

The term "reaction mixture" or "PCR reaction mixture" or "master mix" or "master mixture" refers to an aqueous solution of constituents in a PCR reaction that can be constant across different reactions. An exemplary PCR reaction mixture includes buffer, a mixture of deoxyribonucleoside triphosphates, primers, probes, and DNA polymerase. Generally, template RNA or DNA is the variable in a PCR.

"Sample" or "biological sample" as used herein means a biological material isolated from a subject. The biological sample may contain any biological material suitable for detecting mutant KCNJ5, and may comprise fluid, cellular and/or non-cellular material obtained from the individual.

A "somatic mutation," as used herein, is a genetic alteration acquired by a somatic cell that can be passed on to progeny cells of the mutated somatic cell in the course of cell division. Somatic mutations differ from germ line mutations, which are inherited genetic alterations that occur in germ cells.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely related sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

As used herein, "substantially purified" refers to being essentially free of other components. For example, a substantially purified cell is a cell which has been separated from other cell types with which it is normally associated in its naturally occurring state. In some instances, a population of substantially purified cells refers to a homogenous population of cells. In other instances, this term refers simply to a cell that have been separated from the cells with which they are naturally associated in their natural state.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Targets are sometimes referred to in the art as anti-probes. As the term target is used herein, no difference in meaning is intended.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "substituted alkyl" means alkyl, as defined above, substituted by one, two or three substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "N-linked heterocycle" substituent on a scaffold is a N-containing heterocycle that is linked through its N atom to the scaffold. Examples of non-aromatic N-linked heterocycles include monocyclic groups such as aziridine, azetidine, pyrrolidine, pyrroline, imidazoline, pyrazolidine, piperidine, 1,2,3,6-tetrahydropyridine, 1,4-dihydropyridine, piperazine, morpholine, thiomorpholine, homopiperazine, homopiperidine, and bicyclic groups such as those shown below:

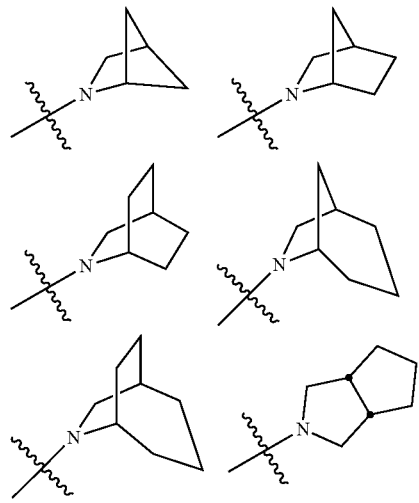

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl. Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The atom or group of atoms may be selected from the group consisting of hydroxyl, carboxyl, cyano (C≡N), nitro ($NO_2$), halogen (preferably, 1, 2 or 3 halogens, especially on an alkyl, especially a methyl group such as a trifluoromethyl), thiol, alkyl group (preferably, $C_1$-$C_{10}$, more preferably, $C_1$-$C_6$), alkoxy group (preferably, $C_1$-$C_{10}$ alkyl or aryl, including phenyl and substituted phenyl), ester (preferably, $C_1$-$C_{10}$ alkyl or aryl), thioether (preferably, $C_1$-$C_{10}$ alkyl or aryl), thioester (preferably, $C_1$-$C_{10}$ alkyl or aryl), (preferably, $C_1$-$C_{10}$ alkyl or aryl), halogen (F, Cl, Br, I), nitro or amine (including a five- or six-membered cyclic alkylene amine, further including a $C_1$-$C_{10}$ alkyl amine or $C_1$-$C_{10}$ dialkyl amine), amido, which is preferably substituted with one or two $C_1$-$C_{10}$ alkyl groups (including a carboxamide which is substituted with one or two $C_1$-$C_{10}$ alkyl groups), alkanol (preferably, $C_1$-$C_{10}$ alkyl or aryl), and alkanoic acid (preferably, $C_1$-$C_{10}$ alkyl or aryl).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Instructional material," as that term is used herein, includes a publication, a recording, a diagram, or any other medium of expression which can be used to communicate the usefulness of the nucleic acid, peptide, and/or compound of the invention in the kit for identifying, diagnosing, alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

DESCRIPTION

The invention relates to compositions and methods for diagnosing and treating adrenal diseases or disorders associated with mutations in KCNJ5. In one embodiment, the invention includes a composition that is a modulator of mutant KCNJ5 for diagnosing or for treating subjects having a mutant KCNJ5. In another embodiment, the modulator of mutant KCNJ5 is an inhibitor of mutant KCNJ5. In another embodiment, the invention includes a method of diagnosing an adrenal disease or disorder associated with mutant KCNJ5. In yet another embodiment, the invention includes a method of treating an adrenal disease or disorder associated with mutant KCNJ5.

Examples of adrenal diseases and disorders associated with mutant KCNJ5 and amenable to the compositions and methods of the invention include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

Examples of pathologies associated with an adrenal disease or disorder also treatable using the compositions and methods of the invention include, but are not limited to, hypernatremia, hypokalemia, hypocalcemia, hypomagnesemia, neoplasia, polyuria, polydipsia, heart disease, renal disease and stroke.

In one embodiment, the mutant KCNJ5 associated with an adrenal disease or disorder is mutant KCNJ5 G151X, which is a KCNJ5 polypeptide comprising at least one mutation at amino acid residue position 151, where is G is replaced by another amino acid residue.

In one embodiment, the mutant polypeptide associated with an adrenal disease or disorder is mutant KCNJ5 L168X, which is a KCNJ5 polypeptide comprising at least one mutation at amino acid residue position 168, where is L is replaced by another amino acid residue.

In one embodiment, the mutant polypeptide associated with an adrenal disease or disorder is mutant KCNJ5 T158X, which is a KCNJ5 polypeptide comprising at least one mutation at amino acid residue position 158, where is T is replaced by another amino acid residue.

In one embodiment, the mutant polypeptide associated with an adrenal disease or disorder is mutant KCNJ5 E145X, which is a KCNJ5 polypeptide comprising at least one mutation at amino acid residue position 145, where is E is replaced by another amino acid residue.

Methods

In various embodiments, the invention relates to a diagnostic method to determine whether a subject has a KCNJ5 mutation associated with an adrenal disease or disorder. The present invention provides methods of assessing the presence or absence of a KCNJ5 mutation associated with an adrenal disease or disorder, as well as methods of diagnosing a subject having a mutation associated with an adrenal disease or disorder.

In some embodiments, the diagnostic assays described herein are in vitro assays. In other embodiments, the diagnostic assays described herein are in vivo assays. In some embodiments of the invention, the adrenal disease or disorder is associated with APA. In other embodiments of the invention, the adrenal disease or disorder is idiopathic. The mutations associated with an adrenal disease or disorder described herein include alterations (e.g., substitution, deletion, insertion, or transition) in the nucleic acid sequence of KCNJ5, as described elsewhere herein throughout. The positions of the mutations in the gene sequences described herein are numbered in relation to the nucleic acid sequence or amino acid sequence. In other words, the numbered position of an altered nucleotide, or amino acid, is the position number of that nucleotide, or amino acid, in the nucleic acid or amino acid sequence.

In one embodiment, the method of the invention is a diagnostic assay for diagnosing an adrenal disease or disorder in a subject in need thereof, by determining whether the subject's adrenal disease or disorder is associated with a mutation in KCNJ5. The results of the diagnostic assay can be used alone, or in combination with other information from the subject, or from the biological sample obtained from the subject, to further treat the patient.

In some embodiments, the biological sample is a bodily tissue. In other embodiments, the biological sample is a bodily fluid. Non-limiting examples of bodily fluids include blood, serum and urine. In some embodiments, the diagnostic assay of the invention is an in vitro assay. In other embodiments, the diagnostic assay of the invention is an in vivo assay. In some embodiments, the KCNJ5 mutation is at least one of G151X, L168X, T158X, or E145X. In other embodiments, the KCNJ5 mutation is at least one of G151R, L168R, T158A, or E145Q.

In one embodiment, the diagnostic assay of the invention comprises administering to a subject, wherein the subject has an adrenal disease or disorder that is potentially associated with a mutation in KCNJ5, at least one composition of the invention, and measuring at least one sign or symptom of the adrenal disease or disease before and after administration of the at least one composition of the invention. If the at least one sign or symptom of the adrenal disease or disorder is improved after administration of the at least one compound of the invention, the subject is diagnosed as having an adrenal disease or disorder that is associated with a mutation in KCNJ5.

In some embodiments, the at least one sign or symptom of the adrenal disease or disorder is an elevated aldosterone level in the serum of the subject. In other embodiments, the at least one sign or symptom of the adrenal disorder is an elevated aldosterone level in the urine of the subject. In one embodiment, the administration of the at least one composition of the invention reduces the aldosterone level in the serum of the subject. In one embodiment, the administration of the at least one inhibitor composition of the invention reduces the aldosterone level in the urine of the subject.

Representative subjects include those who are suspected of having an adrenal disease or disorder, those who have been diagnosed with an adrenal disease or disorder, those whose have an adrenal disease or disorder, those who have had an adrenal disease or disorder, those who at risk of a recurrence of an adrenal disease or disorder, and those who are at risk of developing an adrenal disease or disorder.

In some embodiments, a mutant KCNJ5 inhibiting compound is used in vivo for the diagnosis of an adrenal disease or disorder. In some embodiments, a mutant KCNJ5-inhibiting compound is administered to a subject for a sufficient amount of time to allow the mutant KCNJ5-inhibiting compound to localize to the sites (e.g., tissues, cells, fluids, etc.) in the subject where mutant KCNJ5 is present.

In other embodiments, a mutant KCNJ5 inhibiting compound is used in vivo for the detection of a mutation in KCNJ5. In another embodiment, the mutant KCNJ5 polypeptide has an amino acid comprising at least one mutation at amino acid residue position from about 140 to about 180 relative to SEQ ID NO:7. In some particular embodiments, the KCNJ5 mutation is at least one of G151X, L168X, T158X, or E145X. In other particular embodiments, the KCNJ5 mutation is at least one of G151R, L168R, T158A, or E145Q. In another aspect, the present invention relates to a method of administering a treatment to a subject diagnosed with an adrenal disease or disorder associated with mutant KCNJ5. For example, in one embodiment, the method includes the steps of measuring at least one sign or symptom of the adrenal disorder in the subject, administering a mutant KNCJ5 inhibitor compound to the subject, and measuring the at least one sign or symptom of the adrenal disorder in the subject after administering a mutant KNCJ5 inhibitor compound to the subject, wherein, when the at least one sign or symptom of the adrenal disorder is improved after administration of the mutant KNCJ5 inhibitor compound, the subject is diagnosed as having an adrenal disease or disorder associated with mutant KCNJ5 and administering a treatment to the subject to treat the adrenal disease or disorder associated with mutant KCNJ5.

The treatment may be any treatment or therapy known to persons of skill in the art. In one embodiment, the treatment regimen is selected from the group consisting of surgery, radiation, chemotherapy, administration of a drug, inhibitor, or medication, or combinations thereof. In one embodiment, the drug, inhibitor, or medication includes a compound contemplated within the invention.

The present invention also pertains to kits useful in the methods of the invention. Such kits comprise components useful in any of the methods described herein, including for example, hybridization probes or primers (e.g., labeled probes or primers), reagents for detection of labeled molecules, restriction enzymes (e.g., for RFLP analysis), antibodies, allele-specific oligonucleotides, means for amplification of subject's nucleic acids, means for analyzing the nucleic acid sequence of KCNJ5, means for analyzing the polypeptide sequence of KCNJ5, and instructional materials. For example, in one embodiment, the kit comprises components useful for analysis of KCNJ5 mutations associated with an adrenal disease or disorder. In a preferred embodiment of the invention, the kit comprises components for detecting one or more of the mutations of KCNJ5 associated with an adrenal disease or disorder elsewhere described herein.

Methods of Identifying a Modulator of an Adrenal Disease or Disorder

The current invention also relates to methods of identifying compounds that modulate an adrenal disease or disorder. In some embodiments, the method of the invention identifies a modulator compound that decreases level or activity of a mutant KNCJ5. In other embodiments, the method of the invention identifies a modulator compound that increases the activity of a mutant KCNJ5. The invention further includes compositions comprising the modulator of an adrenal disease or disorder, identified by the methods described herein.

In various embodiments, the adrenal disease or disorder is at least one selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

In one embodiment, the invention comprises a method of identifying a test compound as a modulator of an adrenal disease or disorder. Generally, the method of identifying a test compound as a modulator of an adrenal disease or disorder includes comparing a parameter of an adrenal disease or disorder in the presence of a test compound with a parameter of the adrenal disease or disorder in the absence of the test compound. Thus, in some embodiments, the method includes the steps of: measuring at least one parameter of an adrenal disease or disorder in the absence of the test compound; measuring the at least one parameter of the adrenal disease or disorder in the presence of the test compound; and comparing the level of the at least one parameter of the adrenal disease or disorder in the presence of the test compound with the level of the at least one parameter of the adrenal disease or disorder in the absence of the test compound; and identifying the test compound as a modulator of the adrenal disease or disorder when the level of the at least one parameter of the adrenal disease or disorder in the presence of the test compound is different than the level of the at least one parameter of the adrenal disease or disorder in the absence of the test compound.

In one embodiment, when the level of the parameter of the adrenal disease or disorder is higher in the presence of the test compound, the test compound is identified as an activator. In another embodiment, when the level of the parameter of the adrenal disease or disorder is lower in the presence of the test compound, the test compound is identified as an inhibitor.

In another embodiment, the invention comprises a method of identifying a test compound as a modulator of the mutant KCNJ5 selectivity filter. Generally, the method includes comparing the activity of the mutant KCNJ5 selectivity filter in the presence of a test compound with the activity of the mutant KCNJ5 selectivity filter in the absence of the test compound. Thus, in some embodiments, the method includes the steps of: measuring the activity of the mutant KCNJ5 selectivity filter in the absence of the test compound; measuring the activity of the mutant KCNJ5 selectivity filter in the presence of the test compound; and comparing the level of activity of the mutant KCNJ5 selectivity filter in the presence of the test compound with the level of the activity of the mutant KCNJ5 selectivity filter in the absence of the test compound; and identifying the test compound as a modulator of the activity of the mutant KCNJ5 selectivity filter when the level of the activity of the mutant KCNJ5 selectivity filter in the presence of the test compound is different than the level of the activity of the mutant KCNJ5 selectivity filter in the absence of the test compound.

In one embodiment, when the level of the activity of the mutant KCNJ5 selectivity filter is higher in the presence of the test compound, the test compound is identified as an activator. In another embodiment, when the level of the activity of the mutant KCNJ5 selectivity filter is lower in the presence of the test compound, the test compound is identified as an inhibitor.

Suitable test compounds include, but are not limited to, a chemical compound, a protein, a peptide, a peptidomemetic, an antibody, a nucleic acid, an antisense nucleic acid, an shRNA, a ribozyme, and a small molecule chemical compound.

Other methods, as well as variations of the methods disclosed herein, will be apparent from the description of this invention. In various embodiments, the test compound concentration in the screening assay can be fixed or varied. A single test compound, or a plurality of test compounds, can be tested at one time. Suitable test compounds that may be used include, but are not limited to, proteins, nucleic acids, antisense nucleic acids, small molecules, antibodies and peptides.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223, 409), spores (Ladner U.S. Pat. No. 5,223,409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical that new chemical entities with useful properties are generated by identifying a chemical compound (called a "lead compound") with some desirable property or activity, creating variants of the lead compound, and evaluating the property and activity of those variant compounds.

In one embodiment, high throughput screening methods involve providing a library containing a large number of test compounds potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.
Therapeutic Modulator Compositions and Methods of Use In one embodiment, the compound contemplated within the invention includes a macrolide antibiotic. In another embodiment, the macrolide antibiotic is erythromycin, or a derivative or analogue thereof, or any salt or solvate thereof.

In another embodiment, the macrolide is a motilin-like macrolide (motilide), or a derivative or analogue thereof, or any salt or solvate thereof. In another embodiment, the compound contemplated within the invention is a macrolide that does not exhibit any antibiotic or motilide properties.

Erythromycin derivatives or analogues contemplated within the invention, or a salt or solvate thereof, include:
  erythromycin A oxime;
  pseudo erythromycin A enol ether;
  erythromycin B;
  erythromycin C;
  anhydroerythromycin A;
  mitemcinal (3'-N-dimethyl-11-deoxy-3'-N-isopropyl-12-O-methyl-11-oxo-8,9-didehydroerythromycin; or (1R, 2R,3S,4S,5R,8R,9R,11S)-8-ethyl-4-[(2R,4R,5S,6S)-5-hydroxy-4-methoxy-4,6-dimethyloxan-2-yl]oxy-2-[(2S,3R,4S,6R)-3-hydroxy-6-methyl-4-[methyl(propan-2-yl)amino]oxan-2-yl]oxy-9-methoxy-1,3,5,9,11,13-hexamethyl-7,15-dioxabicyclo[10.2.1]pentadec-12-ene-6,10-dione);
  clarithromycin ((3R,4S,5S,6R,7R,9R,11S,12R,13S,14S)-6-{[(2S,3R,4S,6R)-4-(dimethylamino)-3-hydroxy-6-methyloxan-2-yl]oxy}-14-ethyl-12,13-dihydroxy-4-{[(2R,4S,5S,6S)-5-hydroxy-4-methoxy-4,6-dimethyl-oxan-2-yl]oxy}-7-methoxy-3,5,7,9,11,13-hexamethyl-1-oxacyclotetradecane-2,10-dione);
  roxithromycin ((3R,4S,5S,6R,7R,9R,11S,12R,13S,14R)-6-[(2S,3R,4S,6R)-4-d-3-hydroxy-6-methyloxan-2-yl]oxy-14-ethyl-7,12,13-trihydroxy-4-[(2R,4R,5S,6S)-5-hydroxy-4-methoxy-4,6-dimethyloxan-2-yl]oxy-10-(2-methoxyethoxy methoxyimino)-3,5,7,9,11,13-hexamethyl-1-oxacyclotetradecan-2-one), as well as other N-demethyl, O-alkyl, O-aryl, or O-arylakyl oximes analogues thereof;
  roxithromycin D7;
  dirithromycin ((2R,3R,6R,7S,8S,9R,10R,12R,13S,15R,17S)-9-{[(2S,3R,4S,6R)-4-(dimethylamino)-3-hydroxy-6-methyloxan-2-yl]oxy}-3-ethyl-2,10-dihydroxy-7-{[(2R,4R,5S,6S)-5-hydroxy-4-methoxy-4,6-dimethyloxan-2-yl]oxy}-15-[(2-methoxy ethoxy)methyl]-2,6,8,10,12,17-hexamethyl-4,16-dioxa-14-azabicyclo[11.3.1]heptadecan-5-one), as well as any other prodrug of 9S-erythromycyclamine;
  cethromycin ((1S,2R,5R,7R,8R,9S,11R,13R,14R)-8-[(2S,3R,4S,6R)-4-Dimethylamino-3-hydroxy-6-methyloxan-2-yl]oxy-2-ethyl-1,5,7,9,11,13-hexamethyl-9-[(E)-3-quinolin-3-ylprop-2-enoxy]-3,17-dioxa-15-azabicyclo[12.3.0]heptadecane-4,6,12,16-tetrone);
  spiramycin ((4R,5S,6R,7R,9R,10R,11E,13E,16R)-10-{[(2R,5S,6R)-5-(dimethylamino)-6-methyltetrahydro-2H-pyran-2-yl]oxy}-9,16-dimethyl-5-methoxy-2-oxo-7-(2-oxoethyl)oxacyclohexadeca-11,13-dien-6-yl 3,6-dideoxy-4-O-(2,6-dideoxy-3-C-methyl-α-L-ribo-hexopyranosyl)-3-(dimethylamino)-α-D-glucopyranoside);
  ansamycin;
  oleandomycin ((3R,5R,6S,7R,8R,11R,12S,13R,14S,15S)-14-((2S,3R,4S,6R)-4-(dimethylamino)-3-hydroxy-6-methyltetrahydro-2H-pyran-2-yloxy)-6-hydroxy-12-((2R,4S,5S,6S)-5-hydroxy-4-methoxy-6-methyltetrahydro-2H-pyran-2-yloxy)-5,7,8,11,13,15-hexamethyl-1,9-dioxaspiro[2.13]hexadecane-4,10-dione);
  carbomycin ((12S,13S)-9-Deoxy-12,13-epoxy-12,13-dihydro-9-oxoleucomycin V 3-acetate 4β-(3-methylbutanoate)), tylocine or tylosin (2-[(4R,6S,7R,9R,11E,13E,16R)-6-[(2R,3R,4R,5S,6R)-5-[(2S,4R,5S,6S)-4,5-dihydroxy-4,6-dimethyloxan-2-yl]oxy-4-(dimethylamino)-3-hydroxy-6-methyloxan-2-yl]oxy-16-ethyl-4-hydroxy-15-[[(3R,4R,5R,6R)-5-hydroxy-3,4-dimethoxy-6-methyloxan-2-yl]oxymethyl]-5,9,13-trimethyl-2,10-dioxo-1-oxacyclohexadeca-11,13-dien-7-yl] acetaldehyde);

idremcinal ((2R,3R,4S,5R,8R,9S,10S,11R,12R)-5-ethyl-3,4-dihydroxy-9-[(2R,4R,5S,6S)-5-hydroxy-4-methoxy-4,6-dimethyloxan-2-yl]oxy-11-[(2S,3R,4S,6R)-3-hydroxy-6-methyl-4-[methyl(propan-2-yl)amino]oxan-2-yl]oxy-2,4,8,10,12,14-hexamethyl-6,15-dioxabicyclo[10.2.1]pentadec-1(14)-en-7-one), as well as N-alkyl derivatives thereof; and a compound selected from the group consisting of:

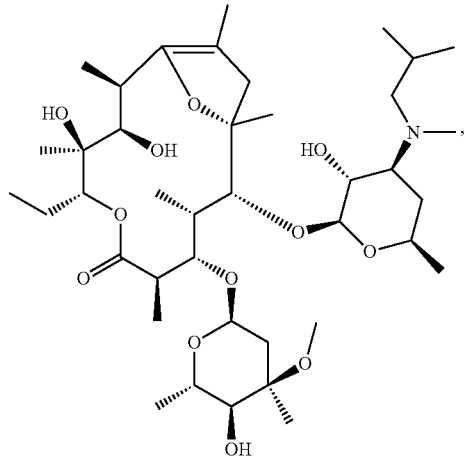

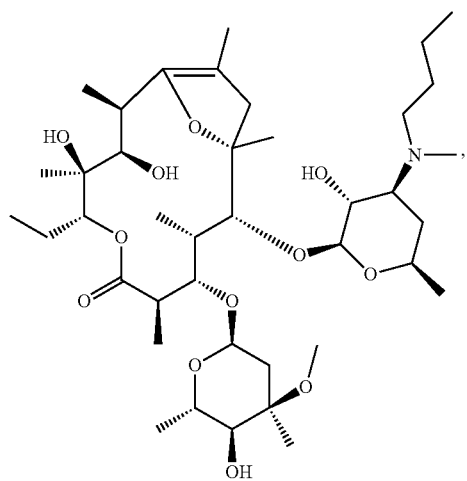

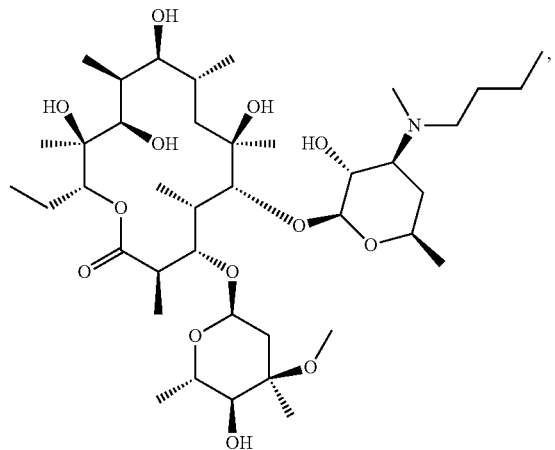

-continued

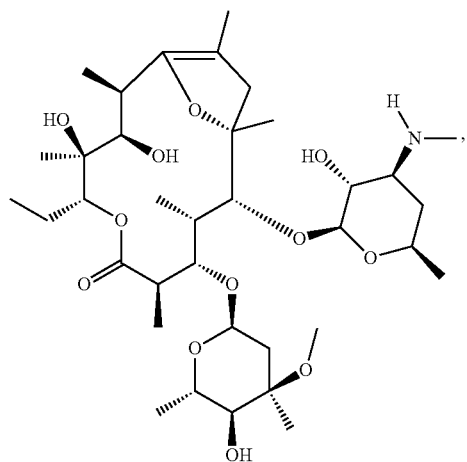

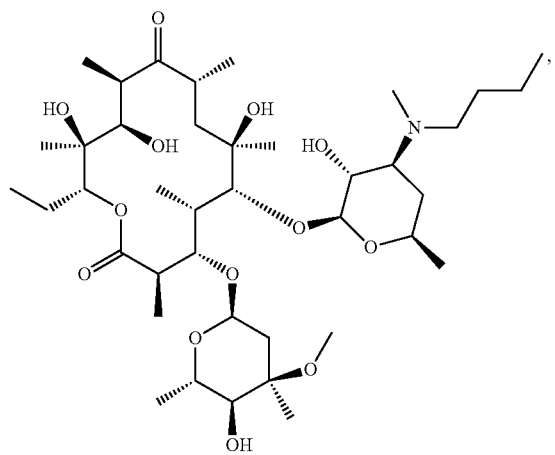

41
-continued
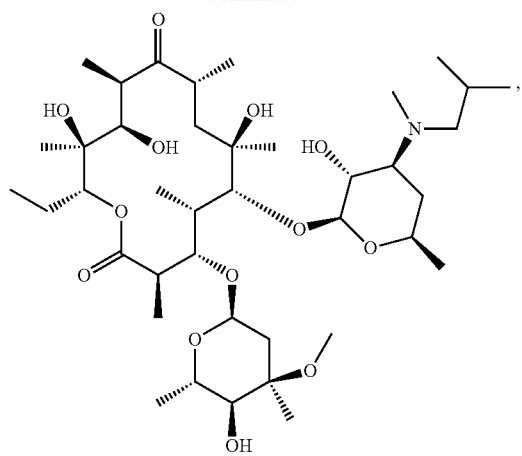
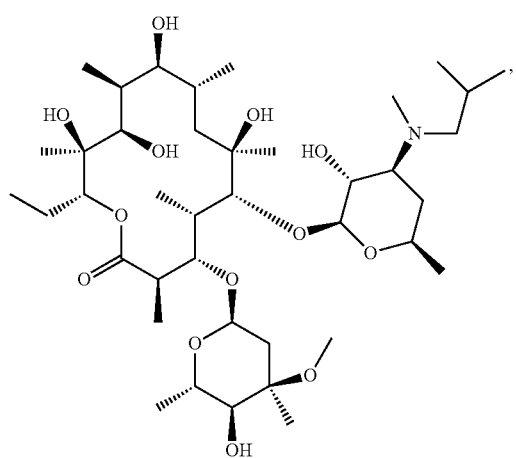
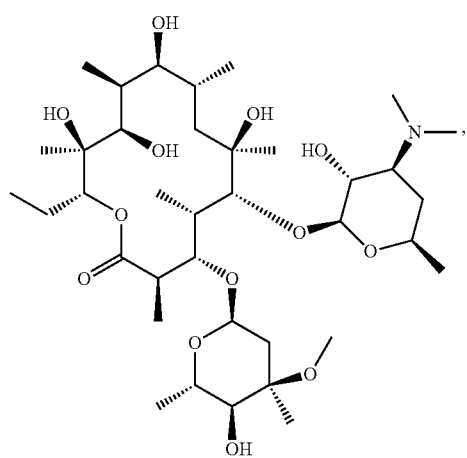
42
-continued
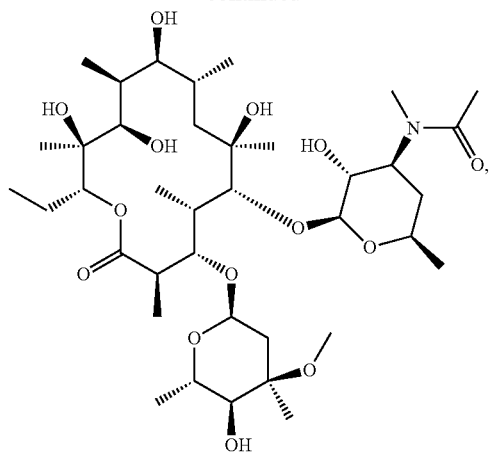
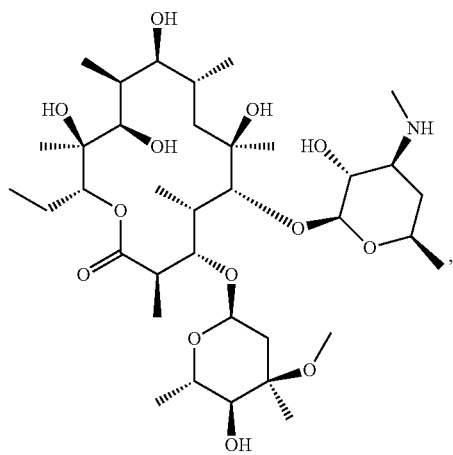
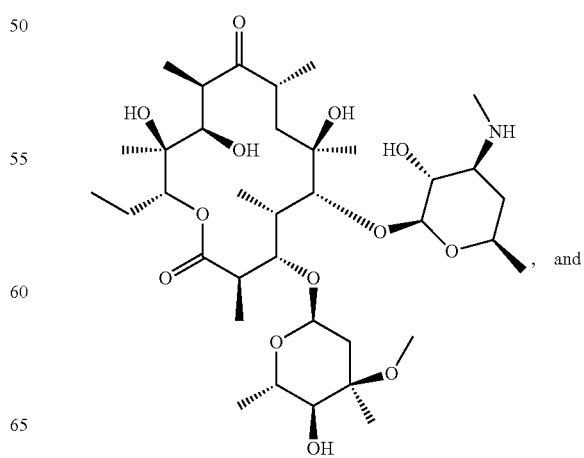
and

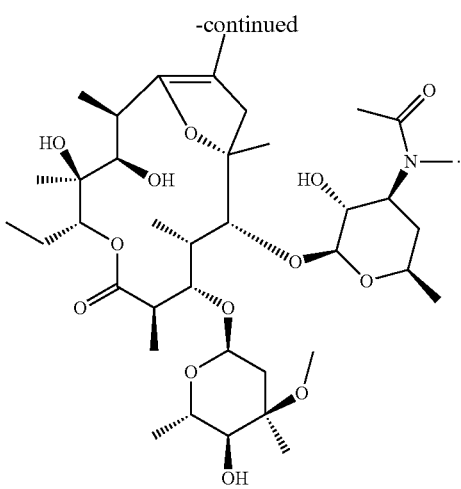

The invention also contemplated using other erythromycin derivatives, such as those disclosed in the U.S. Pat. Nos. RE 39,560; RE 39,531; RE 39,383; 7,022,679; 7,015,203; 6,930,092; 6,927,057; 6,906,039; 6,825,171; 6,753,318; 6,750,204; 6,605,707; 6,599,885; 6,583,120; 6,528,628; 6,528,492; 6,504,017; 6,472,371; 6,468,979; 6,458,771; 6,437,106; 6,403,775; 6,399,582; 6,387,885; 6,342,590; 6,200,813; 6,194,387; 6,191,118; 6,169,168; 6,165,986; 6,140,479; 6,084,079; 6,077,944; 6,063,561; 6,060,234; 6,046,171; 6,034,069; 5,959,088; 5,929,219; 5,922,683; 5,919,916; 5,864,023; 5,854,407; 5,852,180; 5,847,092; 5,837,829; 5,834,438; 5,804,565; 5,780,605; 5,719,272; 5,658,888; 5,635,485; 5,578,579; 5,470,961; 5,403,923; 5,302,705; 5,288,709; and 5,175,150, all of which are herein incorporated by reference in their entireties. For additional macrolides, see also Seiple et al., 2016, Nature 533:338-345, which is incorporated by reference herein in its entirety.

In one embodiment, the compound contemplated within the invention is a compound of formula (I):

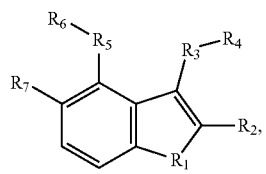

wherein:
$R_1$ is NH, N($C_1$-$C_6$ alkyl), O or S;
$R_2$ is H or $C_1$-$C_6$ alkyl;
$R_3$ is C(O)NH or S(O)$_2$NH, wherein the N atom of $R_3$ is bound to $R_4$;
$R_4$ is aryl or heteroaryl;
$R_5$ is C(O) or $CH_2$;
$R_6$ is a N-linked heterocycle; and
$R_7$ is H, $C_1$-$C_3$ alkyl, OH, $C_1$-$C_3$ alkoxy, F, Cl, Br, I, $CF_3$, $C_1$-$C_3$ haloalkyl, $NO_2$, COOH and $NH_2$; wherein:
  the alkyl and N-linked heterocycle groups are independently and optionally substituted with 1-4 substituents selected from the group consisting of $C_1$-$C_3$ alkyl, OH, $C_1$-$C_3$ alkoxy, F, Cl, Br and I,
  the aryl and heteroaryl groups are independently and optionally substituted with 1-3 substituents selected from the group consisting of $C_1$-$C_3$ alkyl, OH, $C_1$-$C_3$ alkoxy, F, Cl, Br, I, $CF_3$, $C_1$-$C_3$ haloalkyl, $NO_2$, COOH and $NH_2$.

In one embodiment, $R_1$ is O or S. In another embodiment, $R_2$ is $C_1$-$C_6$ alkyl. In yet another embodiment, $R_3$ is C(O)NH. In yet another embodiment, $R_4$ is aryl, optionally substituted with 1-3 substituents selected from the group consisting of $C_1$-$C_3$ alkyl, $C_1$-$C_3$ alkoxy, F, Cl, Br, I, $CF_3$, $C_1$-$C_3$ haloalkyl, and $NO_2$. In yet another embodiment, $R_5$ is $CH_2$. In yet another embodiment, $R_6$ is selected from the group consisting of aziridine, azetidine, pyrrolidine, pyrroline, imidazoline, pyrazolidine, piperidine, 1,2,3,6-tetrahydropyridine, 1,4-dihydropyridine, piperazine, morpholine, thiomorpholine, homopiperazine, homopiperidine, 2-azabicyclo[2.2.1]heptane, 6-azabicyclo[3.2.1]octane and 6-azabicyclo[3.2.2]nonane, all of which are independently substituted with 1-4 substituents selected from the group consisting of $C_1$-$C_3$ alkyl, OH, $C_1$-$C_3$ alkoxy, F, Cl, Br and I.

In one embodiment, the compound of formula (I) is selected from the group consisting of:
5-hydroxy-N-(4-methoxyphenyl)-2-methyl-4-((1,3,3-trimethyl-6-azabicyclo[3.2.1]octan-6-yl)methyl)benzofuran-3-carboxamide:

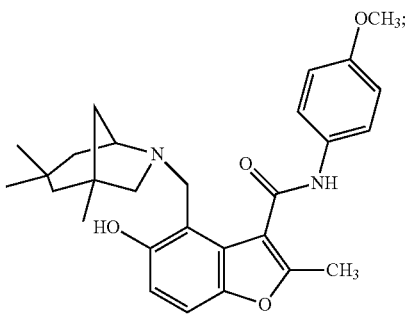 [SMILES: COc1ccc(NC(=O)c2c(C)oc3ccc(O)c(CN4CC5(C)CC4CC(C)(C)C5)c23)cc1]

5-hydroxy-2-methyl-N-phenyl-4-((1,3,3-trimethyl-6-azabicyclo[3.2.1]octan-6-yl)methyl)benzofuran-3-carboxamide:

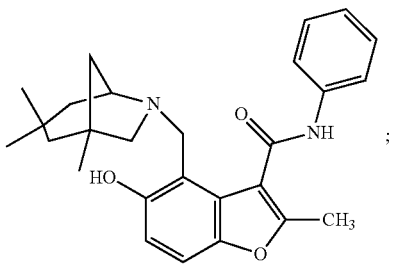 [SMILES: Cc1oc2ccc(O)c(CN3CC4(C)CC3CC(C)(C)C4)c2c1C(=O)Nc1ccccc1]

and
5-hydroxy-2-methyl-4-(piperidin-1-ylmethyl)-N-(3-(trifluoromethyl)phenyl) benzofuran-3-carboxamide:

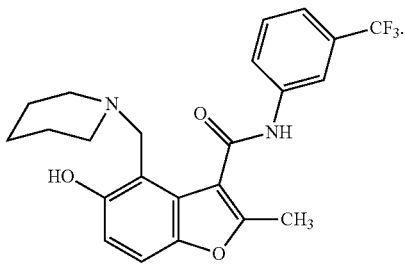 [SMILES: Cc1oc2ccc(O)c(CN3CCCCC3)c2c1C(=O)Nc1cccc(C(F)(F)F)c1]

In various embodiments, the present invention includes modulator compositions and methods of diagnosing or treating an adrenal disease or disorder, as well as methods of diagnosing or treating pathologies associated with an adrenal disease or disorder. In some embodiments, the modulator compositions of the invention are inhibitors of mutant KCNJ5. In various embodiments, the adrenal disease or disorder is at least one selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization. In other various embodiments, the pathology associated with an adrenal disease or disorder is at least one selected from the group consisting of hypernatremia, hypokalemia, hypocalcemia, hypomagnesemia, neoplasia, polyuria, polydipsia, heart disease, renal disease and stroke. In various embodiments, the modulator compositions and methods of treatment of the invention modulate the amount of mutant KCNJ5 polypeptide, the amount of mutant KCNJ5 mRNA, the amount of mutant KCNJ5 activity, or a combination thereof.

In some embodiments, the modulator compositions of the invention are inhibitors of mutant KCNJ5. It will be understood by one skilled in the art, based upon the disclosure provided herein, that modulating the level of mutant KCNJ5 encompasses modulating the level of mutant KCNJ5 expression, including transcription, translation, or both. The skilled artisan will also appreciate, once armed with the teachings of the present invention, that modulating the level of mutant KCNJ5 includes modulating mutant KCNJ5 activity (e.g., selectivity filter activity, etc.). Thus, modulating the level or activity of mutant KCNJ5 includes, but is not limited to, modulating transcription, translation, or both, of a nucleic acid encoding mutant KCNJ5; and it also includes modulating any activity of a mutant KCNJ5 polypeptide as well.

In various embodiments, the modulator compositions and methods of the invention selectively modulate mutant KCNJ5, or can inhibit both wild-type and mutant KCNJ5. In one embodiment, the modulator compositions and methods of the invention selectively inhibit mutant KCNJ5, but do not substantially inhibit wild-type KCNJ5. In another embodiment, the modulator compositions and methods of the invention preferentially inhibit mutant KCNJ5, more than they inhibit wild-type KCNJ5. In a particular embodiment, the modulator compositions and methods of the invention diminish neoplasia associated with an adrenal disease or disorder.

In one embodiment, the modulator compositions and methods of the invention selectively inhibit an activity of the mutant KCNJ5 polypeptide, but do not substantially inhibit the activity of the wild-type KCNJ5 polypeptide. In another embodiment, the modulator compositions and methods of the invention preferentially inhibit an activity of the mutant KCNJ5 polypeptide, more than they inhibit the activity of the wild-type KCNJ5 polypeptide.

In another embodiment, the modulator compositions and methods of the invention selectively inhibit the mutant KCNJ5 selectivity filter, but do not substantially inhibit the wild-type KCNJ5 selectivity filter. In a further embodiment, the modulator compositions and methods of the invention preferentially inhibit the mutant KCNJ5 selectivity filter, more than they inhibit wild-type KCNJ5 selectivity filter. In yet another embodiment, the mutant KCNJ5 modulator of the invention restores potassium channel selectivity to a level comparable to that of wild-type KCNJ5.

Modulation of mutant KCNJ5 can be assessed using a wide variety of methods, including those disclosed herein, as well as methods known in the art or to be developed in the future. That is, the routineer would appreciate, based upon the disclosure provided herein, that modulating the level or activity of mutant KCNJ5 can be readily assessed using methods that assess the level of a nucleic acid encoding mutant KCNJ5 (e.g., mRNA), the level of a mutant KCNJ5 polypeptide present in a biological sample, the level of mutant KCNJ5 activity (e.g., selectivity filter activity, etc.), the level of aldosterone in a bodily fluid, such as the serum or the blood, or combinations thereof.

One skilled in the art, based upon the disclosure provided herein, would understand that the invention is useful in treating an adrenal disease or disorder, or a pathology associated with an adrenal disease or disorder, in a subject in need thereof, whether or not the subject also being treated with other medication or therapy. Further, the skilled artisan would further appreciate, based upon the teachings provided herein, that the pathologies associated with an adrenal disease or disorder treatable by the compositions and methods described herein encompass any pathology associated with an adrenal disease or disorder where mutant KCNJ5 plays a role. In various embodiments, the pathology associated with an adrenal disease or disorder is at least one selected from the group consisting of hypernatremia, hypokalemia, hypocalcemia, hypomagnesemia, neoplasia, polyuria, polydipsia, heart disease, renal disease and stroke.

The mutant KCNJ5 modulator compositions and methods of the invention that modulate the level or activity of mutant KCNJ5 include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof One of skill in the art would readily appreciate, based on the disclosure provided herein, that a mutant KCNJ5 modulator composition encompasses a chemical compound that modulates the level or activity of mutant KCNJ5. Additionally, a mutant KCNJ5 modulator composition encompasses a chemically modified compound, and derivatives, as is well known to one of skill in the chemical arts.

The mutant KCNJ5 modulator compositions and methods of the invention that modulate the level or activity of mutant KCNJ5 include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In one embodiment, the antibody of the invention is an antibody that specifically binds to mutant KCNJ5, and does not substantially bind to KCNJ5. In another embodiment, the antibody of the invention is an antibody that specifically binds to mutant KCNJ5, and also specifically binds to KCNJ5.

Further, one of skill in the art would, when equipped with this disclosure and the methods exemplified herein, appreciate that a mutant KCNJ5 modulator composition includes such modulators as discovered in the future, as can be identified by well-known criteria in the art of pharmacology, such as the physiological results of modulation of mutant KCNJ5 as described in detail herein and/or as known in the art. Therefore, the present invention is not limited in any way to any particular mutant KCNJ5 modulator composition as exemplified or disclosed herein; rather, the invention encompasses those modulator compositions that would be understood by the routineer to be useful as are known in the art and as are discovered in the future.

Further methods of identifying and producing mutant KCNJ5 modulator compositions are well known to those of ordinary skill in the art, including, but not limited, obtaining a modulator from a naturally occurring source (i.e., *Streptomyces* sp., *Pseudomonas* sp., *Stylotella aurantium*). Alternatively, a modulator of mutant KCNJ5 can be synthesized chemically. Further, the routineer would appreciate, based upon the teachings provided herein, that a mutant KCNJ5 modulator composition can be obtained from a recombinant organism. Compositions and methods for chemically synthesizing mutant KCNJ5 modulators and for obtaining them from natural sources are well known in the art and are described in the art.

One of skill in the art will appreciate that a modulator can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is modulator of mutant KCNJ5. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to modulate the amount of mutant KCNJ5, thereby modulating the amount or activity of mutant KCNJ5.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing of mutant KCNJ5 can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that modulators of mutant KCNJ5 can be administered singly or in any combination. Further, modulators of mutant KCNJ5 can be administered singly or in any combination in a temporal sense, in that they may be administered concurrently, or before, and/or after each other. One of ordinary skill in the art will appreciate, based on the disclosure provided herein, that mutant KCNJ5 modulator compositions can be used to treat an adrenal disease or disorder, and that a modulator composition can be used alone or in any combination with another modulator to effect a therapeutic result.

In various embodiments, any of the modulators of the invention described herein can be administered alone or in combination with other modulators of other molecules associated with an adrenal disease or disorder. In some embodiments, the mutant KCNJ5 modulators of the invention selectively inhibit mutant KCNJ5 and do not also inhibit wild-type KCNJ5. In other embodiments, the mutant KCNJ5 modulators of the invention modulate mutant KCNJ5 and also modulate mutant KCNJ5.

It will be appreciated by one of skill in the art, when armed with the present disclosure including the methods detailed herein, that the invention is not limited to treatment of an adrenal disease or disorder, or a pathology associated with an adrenal disease or disorder, that is already established. Particularly, the disease, disorder or pathology need not have manifested to the point of detriment to the subject; indeed, the disease, disorder or pathology need not be detected in a subject before treatment is administered. That is, significant disease or disorder does not have to occur before the present invention may provide benefit. Therefore, the present invention includes a method for preventing an adrenal disease or disorder, in that a mutant KCNJ5 modulator composition, as discussed previously elsewhere herein, can be administered to a subject prior to the onset of the disease or disorder, thereby preventing the disease or disorder. The preventive methods described herein also include the treatment of a subject that is in remission for the prevention of a recurrence of an adrenal disease or disorder, or a pathology associated with an adrenal disease or disorder.

One of skill in the art, when armed with the disclosure herein, would appreciate that the prevention of an adrenal disease or disorder, or a pathology associated with an adrenal disease or disorder, encompasses administering to a subject a mutant KCNJ5 modulator composition as a preventative measure against an adrenal disease or disorder, or a pathology associated with an adrenal disease or disorder. As more fully discussed elsewhere herein, methods of modulating the level or activity of mutant KCNJ5 encompass a wide plethora of techniques for modulating not only mutant KCNJ5 activity, but also for modulating expression of a nucleic acid encoding mutant KCNJ5, including either transcription, translation, or both.

One skilled in the art would understand, once armed with the teaching provided herein, that the present invention encompasses methods of treating or preventing a wide variety of diseases, disorders and pathologies where modulating the expression and/or activity of KCNJ5, and/or mutant KCNJ5, mediates, treats or prevents the disease, disorder or pathology. Non-limiting examples of such diseases, disorders and pathologies include, but are not limited to, long QT syndrome (e.g., long QT syndrome 1, long QT syndrome 13, etc.) and migraines, such as migraines with aura.

Additionally, as disclosed elsewhere herein, one skilled in the art would understand, once armed with the teaching provided herein, that the present invention encompasses a method of preventing a wide variety of diseases, disorders and pathologies where modulating the expression and/or activity of KCNJ5, and/or mutant KCNJ5, mediates, treats or prevents the disease, disorder or pathology. Methods for assessing whether a disease relates to mutant KCNJ5 are known in the art. Further, the invention encompasses treatment or prevention of such diseases discovered in the future.

The invention encompasses administration of modulator of mutant KCNJ5 to practice the methods of the invention; the skilled artisan would understand, based on the disclosure provided herein, how to formulate and administer the appropriate mutant KCNJ5 modulator composition to a subject. Indeed, the successful administration of the mutant KCNJ5 modulator has been reduced to practice as exemplified herein. However, the present invention is not limited to any particular method of administration or treatment regimen.

Pharmaceutical Compositions

Compositions identified as potentially useful modulator compounds for the diagnosis, treatment and/or prevention of an adrenal disease or disorder, can be formulated and administered to a subject for treatment of an adrenal disease or disorder, as now described.

The invention encompasses the preparation and use of pharmaceutical compositions comprising a composition useful for the diagnosis or treatment of an adrenal disease or disorder, disclosed herein as modulator of mutant KCNJ5. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically-acceptable carrier" means a chemical composition with which an appropriate inhibitor thereof, may be combined and which, following the combination, can be used to administer the appropriate inhibitor thereof, to a subject.

The pharmaceutical compositions useful for practicing the invention may be administered to deliver a dose of between about 0.1 ng/kg/day and 100 mg/kg/day.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate inhibitor thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin.

Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers.

Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to 20 about 100 g per kilogram of body weight of the animal. While the precise dosage administered will vary depending upon any number of factors, including, but not limited to, the type of animal and type of disease state being treated, the age of the animal and the route of administration. Preferably, the dosage of the compound will vary from about 1 mg to about 100 mg per kilogram of body weight of the animal. More preferably, the dosage will vary from about 1 µg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1: Identification and Activity of Inhibitor Compounds

Described herein are inhibitors of mutant KCNJ5 channels that are associated with the development of APA. All APA-causing mutations identified are heterozygous and located within or close to the channel's selectivity filter. They render the potassium channel permeable to sodium, leading to cellular depolarization, and activation of pathways that ultimately lead to the formation of a hormone-producing tumor. Mendelian transmission of an autosomal dominant syndrome of severe hypertension and adrenal hyperplasia demonstrates that these KCNJ5 mutations are sufficient for both constitutive aldosterone production and cellular proliferation. The dramatic change in ion selectivity suggests that the structure of the mutant channel sufficiently diverges from that of the wildtype to develop pore blockers that inhibit the mutant, but not the wildtype channel. Although not wishing to be bound by any particular theory, some mutant KCNJ5 inhibitor compounds will block sodium influx via the mutant channel without altering potassium flux through the remaining wildtype channel, thus minimizing side effects. Blocking sodium influx will not only reduce excess aldosterone production from the tumor, but also inhibit its further proliferation. Thus, in addition to their value as a diagnostic, such mutant KCNJ5 inhibitor compounds can serve as therapeutics and potentially replace surgery as a first-line treatment in these patients.

The materials and methods used in this Experimental Example are now described.

Molecular Cloning

Human KCNJ5 was obtained from Origene (#SC119590). The full-length cDNA was sequenced and subcloned into the pIRES2-eGFP vector (Clontech) with EcoRI and BamHI using a PCR-based strategy. Site-directed mutagenesis (Quikchange, Stratagene) was performed to introduce the G151R, T158A, and L168R mutations using the following primers:

```
J5G151R_F:
                              (SEQ ID NO: 1)
5'-CCGAAACAACCATTAGGTATGGCTTCCGAG-3'

J5G151R_R:
                              (SEQ ID NO: 2)
5'-CTCGGAAGCCATACCTAATGGTTGTTTCGG-3'

J5T158A_F:
                              (SEQ ID NO: 3)
5'-CTTCCGAGTCATCGCAGAGAAGTGTCC-3'

J5T158A_R:
                              (SEQ ID NO: 4)
5'-GGACACTTCTCTGCGATGACTCGGAAG-3'

J5L168R_F:
                              (SEQ ID NO: 5)
5'-GGATTATACTCCGCTTGGTCCAGGCC-3'

J5L168R_R:
                              (SEQ ID NO: 6)
5'-GGCCTGGACCAAGCGGAGTATAATCC-3'.
```

All mutations were confirmed by sequencing. cDNA clones encoding human KCNJ3 (Origene #SC118769) and human dopamine receptor D2 (Open Biosystems

MHS1011-74442) were subcloned into the pcDNA3.1(+) vector (Invitrogen) with KpnI and XhoI using PCR-based strategies.

Electrophysiology 293T cells were transfected with plasmid DNA using TransIT®-293 Transfection Reagent (Mirus) according to the manufacturer's instructions. Empty vector was used as a control. Standard perforated whole-cell patch clamp recordings were performed on GFP-positive cells using an Axopatch 200A (Axon Instruments) amplifier. Pipettes were pulled from borosilicate glass and had resistances between 2 MΩ and 4 MΩ with 140 mM KCl in the pipette.

Cells were cotransfected with 0.8 µg wild-type or mutant KCNJ5 and 0.5 µg KCNJ3 cDNA. The extracellular solution contained 140 mM NaCl, 5 mM KCl, 1.8 mM MgCl2, 1.8 mM CaCl2, and 10 mM HEPES (pH 7.4), while the intracellular solution contained 140 mM KCl, 4 mM MgCl2, 1 mM CaCl2, 1 mM EGTA, and 5 mM HEPES (pH 7.4).

1 mM BaCl2 was used to block Kir channels. For ion substitution, 140 mM NaCl was replaced with 140 mM choline chloride with or without the presence of BaCl2. The pipette holding potential was 0 mV before clamping, and the cell was clamped from −100 to 60 mV with 20 mV increments. Endogenous currents of 293T cells transfected with empty vector were measured from −100 to 60 mV. These were considered background currents and subtracted from the whole-cell current for each experiment. Data were analyzed by a combination of Axon Clampfit9.2 (Molecular Devices) and SigmaPlot (Jandel Scientific) programs. Data from 3-7 cells were analyzed for each construct. All data are shown as mean±SEM. Cell capacitances varied between 24.5 and 26 pF, and were used to normalize currents to that of a 25 pF cell.

The relative permeability of K+ to Na+ was estimated from the reversal potential using the Goldman equation with K+ and Na+ as the predominant permeant cations, consistent with experimental data.

$$E_{rev} = \frac{RT}{F} \cdot \ln\frac{\mathcal{P}_K[K^+]_a + \mathcal{P}_{Na}[Na^+]_a}{\mathcal{P}_K[K^+]_i + \mathcal{P}_{Na}[Na^+]_i}$$

$E_{rev}$, reversal potential; p, permeability; R, gas constant; T, temperature (24° C.); F, Faraday's constant.

For measurement of KCNJ3/KCNJ5 response to GPCR activation, 0.5 µg type 2 dopamine receptor (D2R) cDNA was added to the transfection, and cells were stimulated by addition of 1 µM dopamine hydrochloride (Sigma) to the extracellular solution prior to current measurements.

Example KCNJ5 Amino Acid Sequence

KCNJ5;
Genbank Accession Number NP_000881.3;
SEQ ID NO: 7
MAGDSRNAMNQDMEIGVTPWDPKKIPKQARDYVPIATDRTRLLAEGKKPRQ

RYMEKSGKCNVHHGNVQETYRYLSDLFTTLVDLKWRFNLLVFTMVYTVTW

LFFGFIWWLIAYIRGDLDHVGDQEWIPCVENLSGFVSAFLFSIETETTIG

YGFRVITEKCPEGIILLLVQAILGSIVNAFMVGCMFVKISQPKKRAETLM

FSNNAVISMRDEKLCLMFRVGDLRNSHIVEASIRAKLIKSRQTKEGEFIP

LNQTDINVGFDTGDDRLFLVSPLITSHEINQKSPFWEMSQAQLHQEEFEV

-continued
VVILEGMVEATGMTCQARSSYMDTEVLWGHRFTPVLTLEKGFYEVDYNTF

HDTYETNTPSCCAKELAEMKREGRLLQYLPSPPLLGGCAEAGLDAEAEQN

EEDEPKGLGGSREARGSV

Screening

In one embodiment, inhibitor compounds are assessed by electrophysiology to evaluate specific inhibition of the mutant KCNJ5 channel (see FIG. 1). Because it is known that ion channel inhibitors can possibly inhibit the cardiac ion channel hERG, thereby prolonging the QT interval with potentially fatal consequences, all candidate inhibitors of the invention can also be screened for this unwanted activity against hERG.

Electrophysiology of KCNJ5 Channels.

Figure 2:
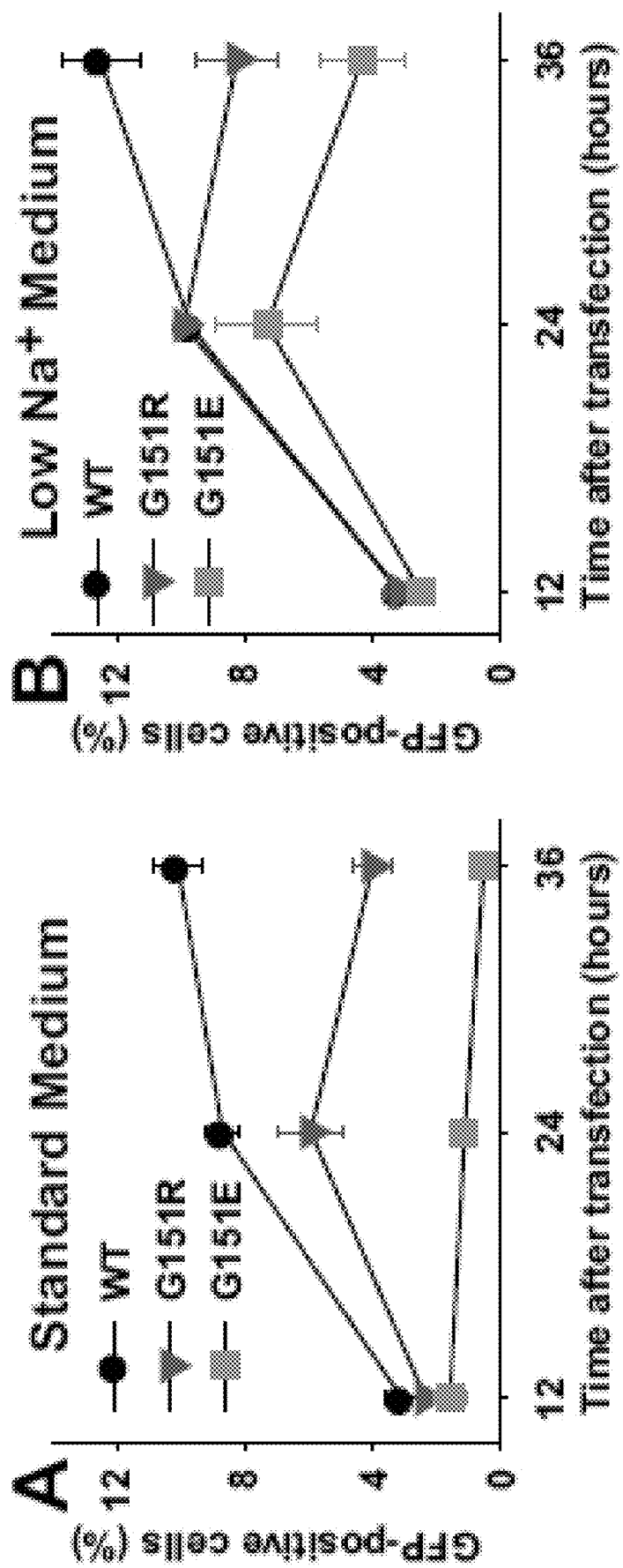
FIG. 2, comprising

Representative whole cell recordings of 293T cells transfected with empty vector, or KCNJ3+WT, or mutant KCNJ5, using the indicated voltage protocol. Extracellular: 140 mM NaCl, 5 mM KCl, 1.8 mM MgCl2, 1.8 mM CaCl2, 10 mM HEPES, pH 7.4; intracellular: 140 mM KCl, 4 mM MgCl2, 1 mM CaCl2, 1 mM EGTA, 5 mM HEPES, pH 7.4. (See (Choi et al., 2011, Science 331:768-772). Stable inducible cell lines expressing wildtype and mutant KCNJ5 channels (Invitrogen Flp-In T-REx 293 Cell Line) have been established. These cells express KCNJ5 channels only after induction with tetracycline or doxycycline. Overexpression in 293 cells cannot be compensated by the high activity of the sodium pump and constitutively active potassium channels characteristic of glomerulosa in vivo, so in contrast to the in vivo situation, overexpression of the mutant channel in 293 cells leads to dramatic excess Na+ influx and rapid cell death (Scholl et al., 2012 PNAS 109:2533-2538), while viability is not reduced in cells expressing the WT channel (see FIG. 2). For screening activities, this provides a phenotype amenable to high-throughput analysis that is directly linked to sodium influx.

For screening activities, the cell line expressing the wild-type channel serves as a positive control (little or no cell death after induction), while induced cells expressing the mutant channel serves as a negative control (cell demise about 24-48 hours after induction). Inhibitor compounds from an ion channel blocker library of compounds will be added at the time of induction at various concentrations, and the presence of viable cells are recorded using an ATP-based assay (CellTiter-Glo™ Luminescent Cell Viability Assay (Promega), amenable to high-throughput analysis). Components that lead to an increased number of viable mutant cells are subjected to further screening by electrophysiology, as described elsewhere herein.

The percentage of eGFP-positive cells was measured at indicated times by flow cytometry (20,000 events counted per data point). Cells carrying mutant channels die from excess sodium influx in standard medium (FIG. 2A). Low sodium medium increases survival (FIG. 2B).

Example 2: Macrolides Specifically Inhibit Mutant KCNJ5 Potassium Channels in Aldosterone-Producing Adenomas The results described herein demonstrate a high-throughput screen for rescue of $KCNJ5^{MUT}$-induced lethality and identified a series of macrolides, including the antibiotic roxithromycin, as potent inhibitors of $KCNJ5^{MUT}$, but not $KCNJ5^{WT}$. Patch clamp electrophysiology demonstrated direct inhibition of $KCNJ5^{MUT}$. Roxithromycin also inhibited KCNJ5$^{MUT}$-induced expression of CYP11B2 (aldosterone synthase) in adrenal-derived H295R cells. Further exploration of macrolides showed that KCNJ5$^{MUT}$ was similarly inhibited by idremcinal, a macrolide motilin receptor agonist, and by derivatives without antibiotic or motilide activity.

The materials and methods used in this Experimental Example are now described.

Generation of Stable Inducible Cell Lines

WT or mutant human KCNJ5 cDNAs (Choi et al., 2011, Science 331:768-772) were subcloned into the pcDNA5/FRT/TO vector using BamHI and HindIII. Single copies of WT or mutant human KCNJ5 cDNAs expressed under the control of tetracycline-inducible promoter were introduced into HEK293 cells using the Flp-in T-Rex System (Invitrogen) according to the manufacturer's instructions. Cells were grown in selective media containing 10% Tet-system approved FBS (Clontech) until induction.

Compound Libraries

All compound libraries were from the Yale Center for Molecular Discovery Research Collection. Compound libraries are formatted as 10 mM stocks in DMSO. For dilution curves, 10 mM stocks of compounds in DMSO were prepared and diluted 2 fold serially in DMSO. In the primary screen, the following libraries were screened: Gen-Plus, Pure Natural Products, Pharmakon 1600 (all 3 Microsource), NIH Clinical Collection, Oncology Set 2, Diversity Set 2, Mechanistic Diversity Set, Natural Products Set (all 4 NCI), Epigenetics Library, Kinase Inhibitor Library, Phosphatase Inhibitor Set, Ion Channel Ligand Library, Bioactive Lipid Library, Metabotropic Glutamatergic Ligand Library, 640 FDA-approved drugs, Nuclear Receptor Ligand Library, Protease Inhibitor Library (all 9 Enzo) and ChemDiv Library.

Cell Viability Assay

20 μl of G151R and L168R cells were plated into sterile white with clear bottom tissue culture treated 384-well plates (Corning) at a density of 2000 cells/well (G151R) or 4000 cells/well (L168R) using a Multidrop Combi Reagent Dispenser (Thermo Scientific). Assay plates were centrifuged and incubated overnight at 37° C. 20 nL was transferred from the compound source plate to the cell assay plate using an Aquarius (Tecan) with a 384-well pin tool (V&P Scientific). The final concentration of compound for screening was 10 μM and the final DMSO concentration was 0.1%. 1 μL of tetracycline (final concentration 1 μg/mL) was added to compound containing and negative control wells by Multidrop Combi to induce expression. 1 μL of media was added to positive control wells. Assay plates were centrifuged and incubated for 72 hours at 37° C., 5% $CO_2$. CellTiter-Glo (Promega) was used to measure cell viability in the assay wells according to the manufacturer's instructions. 10 μL/well of CellTiter-Glo reagent was added to the assay plates using a MultiDrop Combi. The plates were shaken on a Thermomixer R (Eppendorf) at 1100 rpm for 1 minute and incubated in the dark for 10 minutes at room temperature. Luminescence was read on an Envision plate reader (PerkinElmer) with 0.3 second sampling time per well. Raw data (luminescence counts per second) was normalized to percent effect by the formula 100−(((sample−negative control mean)/(positive control mean−negative control mean))*100).

Membrane Potential Assay

20 μL of WT cells were plated into sterile black with clear bottom tissue culture-treated 384-well plates (Corning) at a density of 10000 cells/well using a Multidrop Combi. Assay plates were centrifuged at 500 rpm for 10 seconds and incubated overnight at 37° C. in a humidified 5% $CO_2$ incubator. After the overnight incubation, 1 μL of tetracycline (final conc. 1 μg/mL) was added to all wells by Multidrop Combi to induce KCNJ5. Assay plates were centrifuged at 500 rpm for 10 seconds and incubated overnight at 37° C. in a humidified 5% $CO_2$ incubator. The next day, 10 μL of medium was removed from each well using a PlateMate Plus (Thermo Scientific). 10 μL of Blue Formula FLIPR membrane potential dye (Molecular Devices) was added to cells using a Multichannel pipettor. Assay plates were incubated for 30 minutes. at 37° C. After incubation, 20 nL was transferred twice from the compound source plate to the cell assay plate using an Aquarius with a 384-well pin tool for a total transfer volume of 40 nL and a final DMSO concentration of 0.2%. 1 μL of 20 mM $BaCl_2$ was added to positive control wells using a Multichannel pipettor. The assay plate was incubated 20 minutes at room temperature in the dark. Fluorescence was read in a FlexStation II 384 plate reader (Molecular Devices) at 530/565 nm ex/em, bottom read.

Statistical Analysis

Data was analyzed using the programs Excel (Microsoft) and Prism (GraphPad). Errors are SD unless otherwise indicated in the legend. Dose-response curves were fitted with a four-parameter logistic equation:

$$F(x)=D+(A-D)/(1+(x/C)^B), \text{ with}$$

A=minimum inhibition
B=Hill's slope
C=inflection point
D=maximum inhibition

Synthesis of Macrolide Derivatives

The synthesis of PLUX 30B, 31A, 32, 33, 35A, 37 and 38, 40 (Shaw et al., 2009, J. Med. Chem. 52:6851-6859) and PLUX 36 (Tsuzuki et al., 1989, Chem. Pharm. Bull. 37:2687-2700) was performed using previously described methods. The acylation reaction needed to synthesize PLUX 34, 39 and 42 has also been described in the literature (Flynn et al., 1955, J. Am. Chem. Soc. 77:3104-3106). The synthesis of PLUX33 or N-demethyl-9-deoxo-9-hydroxy-N-butyl-(9S)-erythromycin was made in a manner identical to PLUX32, only 1-iodobutane was used as the alkylating agent. Crude product was purified by silica gel chromatography, eluting with 6% (8:1, ethanol/ammonium hydroxide) in ethyl acetate to give 142 mg, 52% product as a colorless solid. $^1$H NMR (400 MHz, DMSO-$d_6$) δ 5.56 (d, J=5.7 Hz, 1H), 4.92 (d, J=9.8 Hz, 1H), 4.79 (d, J=4.7 Hz, 1H), 4.53 (s, 1H), 4.39 (d, J=2.1 Hz, 1H), 4.28 (d, J=7.4 Hz, 1H), 3.86 (m, 5H), 3.70 (s, 1H), 3.59 (d, J=5.1 Hz, 1H), 3.55 (2, 1H), 3.20 (s, 3H), 3.04 (d, J=8.5 Hz, 2H), 2.88 (dd, J=9.4, 7.4 Hz, 1H), 2.67 (m, 1H), 2.54 (m, 1H), 2.48 (m, 1H), 2.32 (m, 1H), 2.27 (d, J=15.2 Hz, 1H), 2.15 (s, 3H), 1.89 (s, 1H), 1.73 (m, 3H), 1.56 (d, J=10.9 Hz, 1H) 1.46 (m, 2H), 1.40-1.19 (m, 5H), 1.15-0.92 (m, 29H), 0.85 (t, J=7.2 Hz, 3H), 0.74 (t, J=7.4 Hz, 3H). m/z: 778 [M+H]$^+$ (found [M+H]$^+$, 778.5310, requires $C_{40}H_{75}NO_{13}$ [M+H]$^+$778.5317). PLUX36 or N-demethyl-8,9-anhydroerythromycin A 6,9-hemiacetal and PLUX37 or N-demethyl-N-isobutyl-8,9-anhydroerythromycin A 6,9-hemiacetal was synthesized using previously described methods (Tsuzuki et al., 1989, Chem. Pharm. Bull. 37:2687-2700). PLUX40 or N-demethyl-N-(2-methylpropyl)-erythromycin was accomplished by alkylating known N-demethylerythromycin in a manner identical to PLUX32, using 1-iodo-2-methylpropane as the alkylating agent. Crude product was purified by silica gel chromatography eluting with 4% (8:1, ethanol/ammonium hydroxide) in dichloromethane to give product 85 mg, 52% yield. $^1$H NMR (400

MHz, DMSO-d$_6$) δ 5.13-5.04 (m, 1H), 4.72 (d, J=4.8 Hz, 1H), 4.50 (s, 1H), 4.36 (d, J=7.6 Hz, 1H), 4.30-4.23 (m, 2H), 4.08-3.94 (m, 2H), 3.90-3.82 (m, 2H), 3.75 (dd, J=5.9, 2.0 Hz, 1H), 3.60 (s, 1H), 3.46 (d, J=7.2 Hz, 1H), 3.19 (s, 3H), 3.03 (td, J=8.0, 7.5, 3.8 Hz, 1H), 2.93-2.71 (m, 4H), 2.65 (m, 1H), 2.46-2.38 (m, 1H), 2.33-2.08 (m, 6H), 1.92-1.60 (m, 5H), 1.60-1.45 (m, 3H), 1.43-1.32 (m, 2H), 1.26 (s, 4H), 1.15 (d, J=6.1 Hz, 3H), 1.11 (s, 3H), 1.09 (d, J=7.3 Hz, 3H), 1.07-1.01 (m, 6H), 1.02-0.96 (m, 6H), 0.82 (dd, J=6.5, 2.6 Hz, 6H), 0.74 (t, J=7.4 Hz, 3H) m/z: 776 [M+H]$^+$ (found [M+H]$^+$, 776.5184, requires C$_{40}$H$_{73}$NO$_{13}$ [M+H]$^+$ 776.5160).

Kirby-Bauer Disk Diffusion Assay

*Staphylococcus aureus* (ATCC 25923) was streaked on Kirby-Bauer plates. 18 nmol compound was added to a sterile filter paper disk and placed on the plate. After incubation at 37° C., the diameter of the inhibitory zone was recorded.

Electrophysiology

HEK293T cells (American Type Culture Collection) were used for transient expression of GFP-tagged KCNJ5 or KCNJ3. The cells were grown in Dulbecco's modified Eagle medium (DMEM; Invitrogen) supplemented with 10% FBS (Invitrogen) in 5% CO$_2$ and 95% air at 37° C. Cells were grown to 50-70% confluence for transfection, and the corresponding cDNAs (Choi et al., 2011, Science 331:768-772) were simultaneously applied to the cells using TurboFect transfection reagent according to the manufacturer's protocol (Fermentas). Briefly, a cDNA cocktail (0.5 μg GFP-tagged KCNJ5 and 0.5 μg KCNJ3) was diluted with 200 μl serum free DMEM and further mixed with 4 μl Turbofect transfection reagent for the transfection of cells cultured in 35 mm Petri dishes. For studying the K$^+$/cation channel activity of homotetramer KCNJ5, 1 μg cDNA was used for transfection. Cells transfected with vector alone were used as a control and their background currents were subtracted from the experimental groups. After 15 minutes incubation at room temperature, the mixture of the transfection agents was applied to the cells, followed by additional 24 hr incubation before use. Roxithromycin (Sigma-Aldrich) was dissolved in the bath solution to reach the designated concentrations. To determine the Ba$^{2+}$-sensitive K$^+$ currents, 1 mM BaCl$_2$ was used at the end of experiments. For the examination of the effect of roxithromycin on cation currents in cells transfected with KCNJ5 mutants (G151R or L168R), 1 mM BaCl$_2$ was present in the bath solution throughout the experiments.

Within 24 hr after transfection, the cells were treated with trypsin-containing medium (TrypLE Express) (Gibco) for 10 minutes to detach the cells. The perforated whole-cell patch-clamp experiments were carried out at room temperature. The cells were incubated with a KCl bath solution containing 140 mM KCl, 1.8 mM MgCl$_2$, 1.8 mM CaCl$_2$, and 10 mM HEPES (pH 7.4) or with a Na Ringer bath solution (140 mM NaCl, 5 mM KCl, 1.8 mM MgCl$_2$, 1.8 mM CaCl$_2$, and 10 mM HEPES). Fluorescence signal (an indication of positive transfection) was detected with an intensified video imaging system including a SIT 68 camera (Long Island Industries). Borosilicate glass (1.7-mm OD) was used to make the patch-clamp pipettes that were pulled with a Narishege electrode puller. The pipette had a resistance of 2-4 MΩ when filled with 140 mM KCl. The tip of the pipette was filled with pipette solution containing 140 mM KCl, 2 mM MgCl2, 1 mM EGTA, and 5 mM HEPES (pH 7.4). The pipette was then back-filled with amphotericin B (20 μg/0.1 ml) containing pipette solution. After forming a high resistance seal (>2 GΩ), the membrane capacitance was monitored until the whole-cell patch configuration was formed. The cell membrane capacitance was measured and compensated. The K/cation currents were measured from −80 mV to 20 mV with 20 mV steps by an Axon 200A patch-clamp amplifier. The currents were low-pass filtered at 1 KHz and digitized by an Axon interface (Digidata 1200) and were analyzed using the pClamp software system 9 (Axon). The data are presented as mean±standard error of the mean. Student's t test or one-way ANOVA was used to determine the statistical significance. P<0.05 was considered to be significant.

Real-Time PCR

H295R cells were cultured in DMEM/F12, HEPES (Gibco) supplemented with 2.5% Ultroser G (Pall Biosepra), 1% ITS+ Premix (Corning) and 1% Penicillin/Streptomycin (Gibco). Plasmids were purified using the Endofree Maxi Kit (Qiagen). Roxithromycin stock solutions were 100 mM in DMSO (both Sigma-Aldrich). 3×10$^6$ cells were transfected with 3 μg pIRES eGFP containing no insert, WT or mutant KCNJ5 using an Amaxa Nucleofector I (program P-20) and the Nucleofector Kit R (Lonza). Cells were allowed to recover briefly in RPMI 1640 medium (Gibco). Two identical transfections were pooled, resuspended in 10 mL medium containing 20 μM roxithromycin and plated on 4 wells of a 12-well plate. Transfection was confirmed via fluorescence microscopy. After 25 hours, cells were washed with PBS, and medium containing 0.1% Ultroser G and DMSO (vehicle), 5, 20 or 50 μM roxithromycin was added. After an additional 18 h, RNA was harvested using the RNeasy Mini Kit (Qiagen) following the manufacturer's instructions. 300 ng RNA were transcribed using the Quantitect Reverse Transcription Kit (Qiagen). Expression levels of CYP11B2 and GAPDH were quantified in triplicates in a 7300 Real-Time PCR System (Applied Biosystems) using the Taqman Gene Expression Master Mix and assays Hs01597732_m1 (CYP11B2) or HS02758991_g1 (GAPDH) (all Applied Biosystems). DDCT values were calculated by normalization of DCT values, using the average DCT of vehicle treated empty vector-transfected cells as a reference.

The results of the experiments are now described.

To screen for inhibitors of mutant and wild-type KCNJ5 channels, stable HEK293 cell lines using the commercially available Flp-in T-Rex System were generated, in which single copies of desired genes are integrated into a common site in the genome under control of a tetracycline-inducible CMV promoter. Cell lines with inducible expression of KCNJ5$^{WT}$, KCNJ5$^{G151R}$, or KCNJ5$^{L168R}$ were produced. While induction of KCNJ5$^{WT}$ expression had no effect on cell viability, cells expressing KCNJ5$^{G151R}$ or KCNJ5$^{L168}$ died rapidly, an effect previously demonstrated to be Na$^+$-dependent for KCNJ5$^{G151R13}$.

Figure 3:
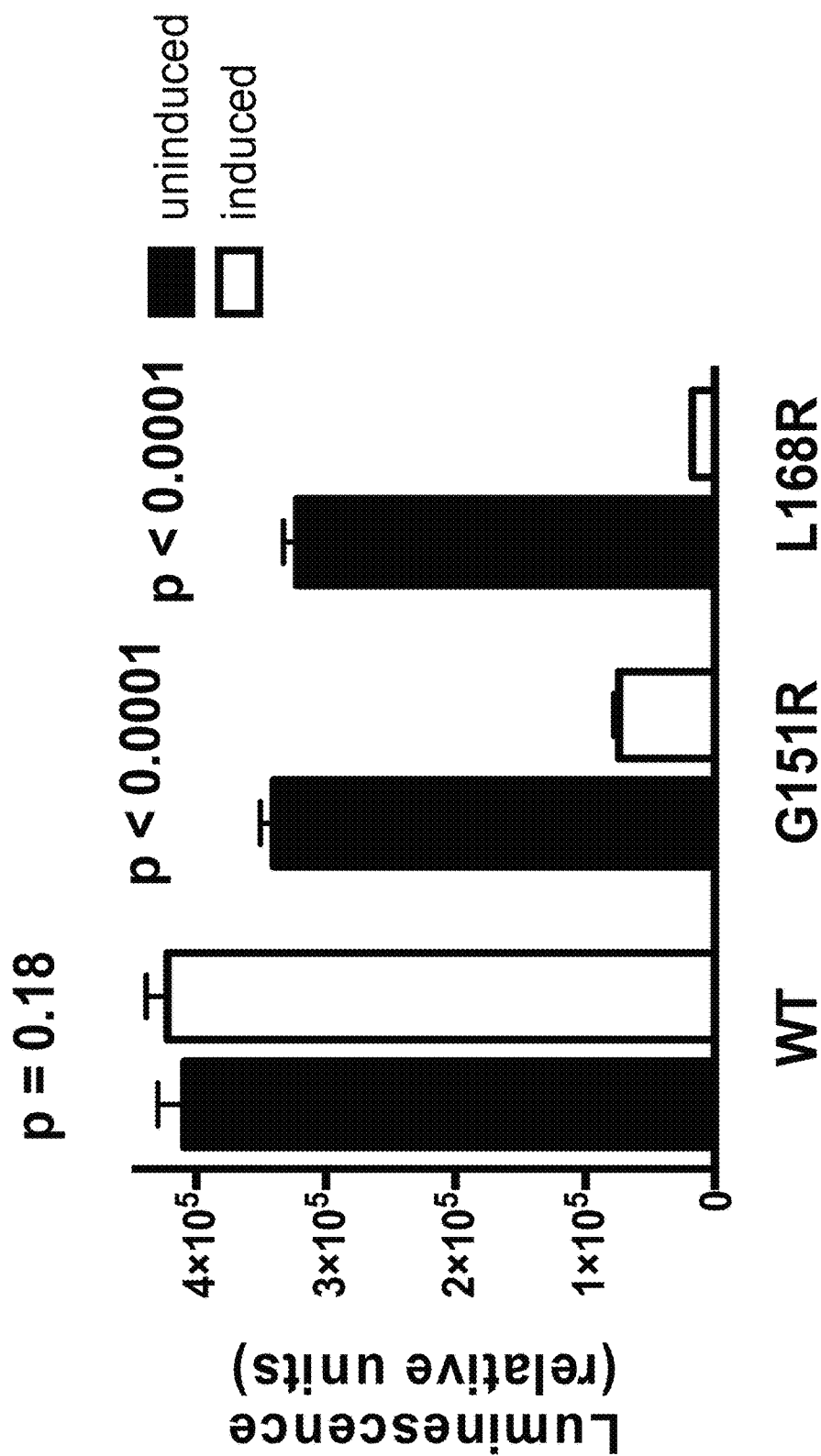
FIG. 3 is a graph of experimental data depicting reduced ATP levels following induction of $KCNJ5^{G151R}$ or $KCNJ5^{L168R}$ but not $KCNJ5^{WT}$ in HEK293 cells. Cell survival was measured using an ATP-based viability assay with luminescence as a read-out in $KCNJ5^{WT}$, $KcNJ5^{G151R}$, and $KcNJ5^{L168R}$ stable inducible cell lines in the uninduced and induced state. Whereas induction of $KCNJ5^{WT}$ expression had no significant effect on ATP levels, induction of $KCNJ5^{G151R}$ and $^{L168R}$ led to a significant decrease in ATP levels. p values represent unpaired Student's t-test comparing uninduced vs. induced for each line. N=8 for each condition, 2000 cells per well (WT and G151R) or 4000 cells per well (L168R).

Cellular ATP levels were measured as a proxy for cell viability, using a commercially available luciferase assay (Crouch et al., 1993, Proc. Natl. Acad. Sci. U.S.A. 109: 2533-2538). Induction of KCNJ5$^{WT}$ had no effect on ATP levels. In contrast, induction of KCNJ5$^{G151R}$ or KCNJ5$^{L168R}$ led to drastically reduced ATP levels 72 hours after induction (FIG. 3). This allowed high-throughput screening for inhibitors that prevented reduction in ATP levels upon induction of KCNJ5$^{G151R}$ or KCNJ5$^{L168R}$.

Conditions were designed to maximize reproducibility and the signal-to-background ratios (S/B) (Zhang et al., 1999, J. Biomol. Screen 4:67-73) comparing ATP level in uninduced and induced cells. Screening was performed in 384-well plates; compounds were added 24 hours after plating, and channel expression was induced immediately after compound addition. ATP levels were measured 72 hours after induction.

Figure 4:
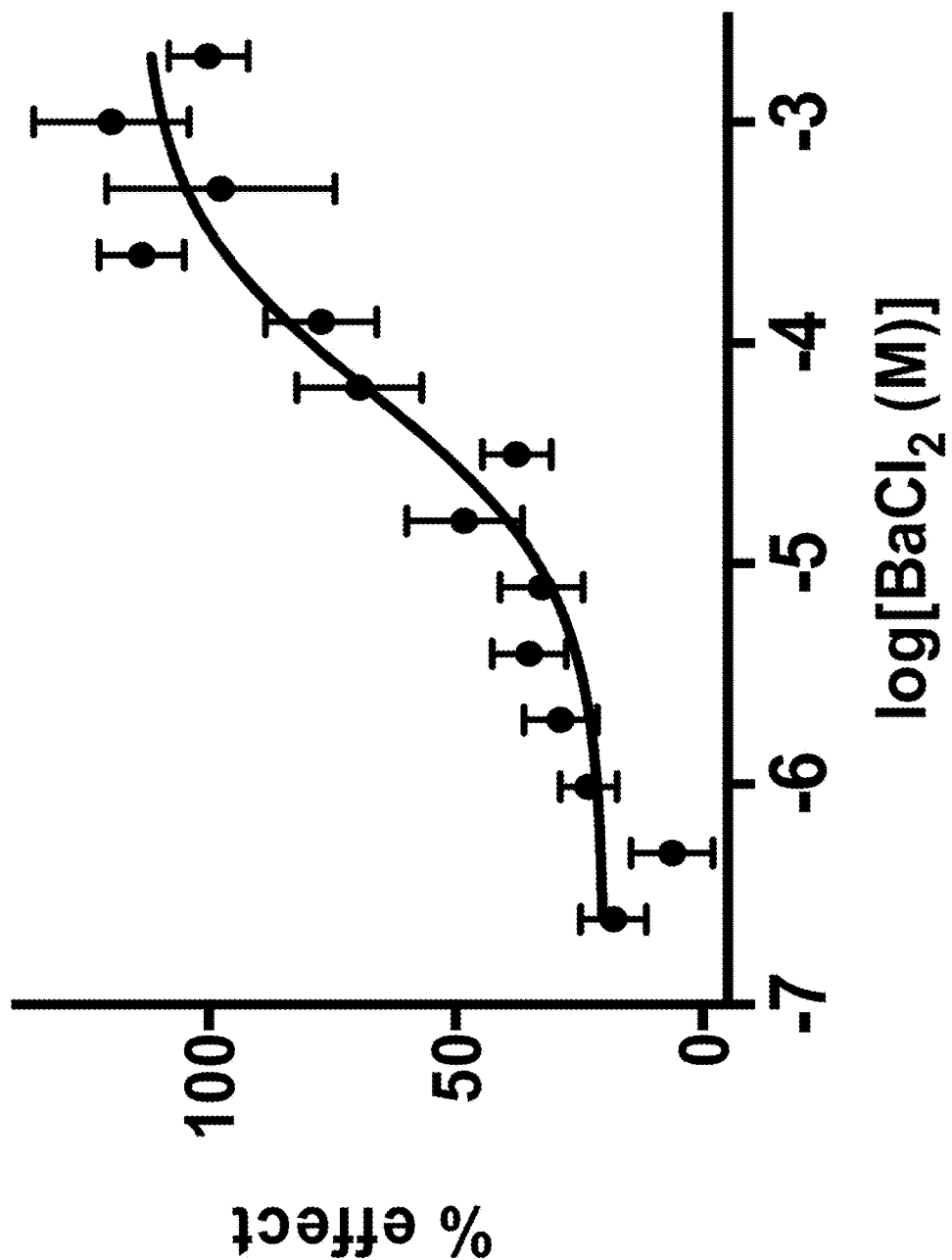
FIG. 4 is a graph of experimental data depicting evaluation of the $KCNJ5^{WT}$ assay using $BaCl_2$. The $KCNJ5^{WT}$ membrane potential assay (see methods) was evaluated using a standard curve of $BaCl_2$ concentrations. Depolarization caused by increasing $BaCl_2$ concentrations led to an increase in fluorescence. 1 mM $BaCl_2$ was defined as 100% effect. Data was fitted with a four-parameter non-linear regression of log-dose versus response.

Because expression of KCNJ5$^{WT}$ in HEK293 cells does not cause lethality (FIG. 3), a different assay for inhibition of this channel was required. Expression of KCNJ5$^{WT}$ in HEK293 cells leads to K$^+$ efflux and membrane hyperpolarization (Choi et al., 2011, Science 331:768-772), an effect that is reversible upon inhibition of the channel with the potassium channel blocker barium. Changes in membrane potential were detected using a well-established fluorescence-based measure of membrane potential (FIG. 4).

KCNJ5$^{G151R}$, the most frequent mutation in APAs (Akerstrom et al. 2012, PLoS ONE 7:e41926), was used for the primary screen. Levels of ATP in uninduced and induced cells without added test compound defined 100% and 0% effect, respectively, and served as a proxy for lethality. 73,001 compounds from 19 libraries were screened for rescue of KCNJ5$^{G151R}$-induced lethality at a concentration of 10 μM. 77.6% of all compounds tested showed <5% increase in ATP compared to no added compound, and 94.6% of all compounds showed <10% effect. 398 compounds (0.5%) showed at least a 33.3% effect. In confirmatory testing, 92 distinct compounds (0.1% of all compounds from the initial screen) again produced ≥33.3% increase in ATP (Table 1).

TABLE 1

Compounds with >33.3% effect in primary screen and "hit pick"

| Compound ID | Supplier | Supplier ID | Drug Name | % effect (1) | % effect (2) | mean % effect |
|---|---|---|---|---|---|---|
| Fass | Microsource | 1503276 | Roxithromycin | 107.6 | 107.0 | 107.3 |
| YU199271 | ChemDiv | G118-0224 | | 83.9 | 102.3 | 93.1 |
| YU156201 | ChemDiv | 3132-1065 | | 100.5 | 81.0 | 90.7 |
| YU156312 | ChemDiv | 3232-1884 | | 109.1 | 70.3 | 89.7 |
| YU200104 | ChemDiv | G281-1947 | | 87.9 | 90.9 | 89.4 |
| YU194148 | ChemDiv | F471-0857 | | 68.2 | 110.6 | 89.4 |
| YU170857 | ChemDiv | 3572-5949 | | 79.4 | 98.0 | 88.7 |
| YU194117 | ChemDiv | F471-0014 | | 80.3 | 96.1 | 88.2 |
| YU195258 | ChemDiv | F580-0413 | | 98.0 | 74.1 | 86.1 |
| YU164410 | ChemDiv | D089-0525 | | 72.1 | 99.3 | 85.7 |
| YU192559 | ChemDiv | F351-0044 | | 106.7 | 61.8 | 84.2 |
| YU186983 | ChemDiv | E612-0759 | | 100.6 | 63.9 | 82.3 |
| YU221968 | NCI | NSC645033 | Pyrimidine | 77.2 | 86.6 | 81.9 |
| YU156202 | ChemDiv | 3132-1071 | | 107.1 | 49.8 | 78.5 |
| YU156203 | ChemDiv | 3132-1074 | | 83.6 | 68.5 | 76.1 |
| YU155936 | ChemDiv | 2434-0130 | | 80.2 | 70.7 | 75.5 |
| YU164355 | ChemDiv | D089-0323 | | 82.5 | 68.3 | 75.4 |
| YU214474 | ChemDiv | L437-0030 | | 41.7 | 108.8 | 75.3 |
| YU186982 | ChemDiv | E612-0750 | | 83.3 | 64.8 | 74.1 |
| YU205248 | ChemDiv | G764-0071 | | 84.3 | 62.8 | 73.6 |
| YU176999 | ChemDiv | C700-2077 | | 80.3 | 66.2 | 73.2 |
| YU034553 | Microsource | 1501176 | Erythromycin | 91.9 | 54.2 | 73.0 |
| YU173899 | ChemDiv | C200-9149 | | 70.1 | 75.5 | 72.8 |
| YU039827 | Microsource | 2300165 | Amiodarone hydrochloride | 77.8 | 65.9 | 71.8 |
| YU200116 | ChemDiv | G281-2440 | | 54.5 | 87.7 | 71.1 |
| YU164429 | ChemDiv | D089-0725 | | 65.8 | 75.6 | 70.7 |
| YU182169 | ChemDiv | D393-0253 | | 63.3 | 77.5 | 70.4 |
| YU163288 | ChemDiv | C620-0363 | | 70.5 | 68.6 | 69.5 |
| YU164416 | ChemDiv | D089-0533 | | 53.7 | 82.7 | 68.2 |
| YU214875 | ChemDiv | L491-0661 | | 84.0 | 52.1 | 68.1 |
| YU165270 | ChemDiv | D297-0001 | | 94.9 | 40.9 | 67.9 |
| YU164350 | ChemDiv | D089-0310 | | 81.9 | 50.4 | 66.1 |
| YU039449 | NCC | SAM001246981 | Indatraline | 70.6 | 61.3 | 65.9 |
| YU171244 | ChemDiv | 5340-0013 | | 58.6 | 73.1 | 65.8 |
| YU155938 | ChemDiv | 2434-0134 | | 83.4 | 47.9 | 65.7 |
| YU195274 | ChemDiv | F580-1522 | | 74.6 | 49.9 | 62.3 |
| YU156667 | ChemDiv | 3534-0434 | | 68.1 | 56.0 | 62.0 |
| YU164338 | ChemDiv | D089-0264 | | 54.7 | 69.0 | 61.9 |
| YU164351 | ChemDiv | D089-0311 | | 77.7 | 44.0 | 60.8 |
| YU164423 | ChemDiv | D089-0559 | | 66.6 | 54.9 | 60.8 |
| YU200600 | ChemDiv | G345-0648 | | 84.8 | 36.5 | 60.6 |
| YU164347 | ChemDiv | D089-0297 | | 64.9 | 56.2 | 60.6 |
| YU164343 | ChemDiv | D089-0287 | | 55.9 | 64.5 | 60.2 |
| YU171246 | ChemDiv | 5340-1529 | | 49.4 | 70.7 | 60.0 |
| YU225090 | Enzo | CA-305 | Phenoxybenzamine-HCl | 67.8 | 52.1 | 59.9 |
| YU161687 | ChemDiv | 8017-3019 | | 65.0 | 53.9 | 59.4 |
| YU177007 | ChemDiv | C700-2100 | | 63.5 | 54.8 | 59.2 |
| YU170768 | ChemDiv | 3141-0464 | | 75.7 | 40.9 | 58.3 |
| YU158463 | ChemDiv | 5137-3628 | | 58.7 | 57.6 | 58.2 |
| YU223483 | NCI | NSC341196 | | 48.0 | 68.3 | 58.1 |
| YU159856 | ChemDiv | 6456-0125 | | 62.8 | 53.1 | 58.0 |
| YU224116 | Enzo | KC-159 | U-37883A-HCl | 49.9 | 65.8 | 57.9 |
| YU223163 | NCI | NSC33823 | | 43.9 | 65.7 | 54.8 |
| YU200092 | ChemDiv | G281-1685 | | 47.4 | 60.1 | 53.8 |
| YU164352 | ChemDiv | D089-0316 | | 55.1 | 52.4 | 53.7 |
| YU164430 | ChemDiv | D089-0731 | | 39.2 | 68.3 | 53.7 |

TABLE 1-continued

Compounds with >33.3% effect in primary screen and "hit pick"

| Compound ID | Supplier | Supplier ID | Drug Name | % effect (1) | % effect (2) | mean % effect |
|---|---|---|---|---|---|---|
| YU033748 | Enzo | DL-247 | Clemastine | 60.8 | 44.6 | 52.7 |
| YU207124 | ChemDiv | G856-5896 | | 47.7 | 57.8 | 52.7 |
| YU164420 | ChemDiv | D089-0547 | | 62.5 | 42.4 | 52.4 |
| YU221408 | NCI | NSC719276 | Fulvestrant | 65.0 | 39.6 | 52.3 |
| YU164426 | ChemDiv | D089-0562 | | 59.6 | 44.2 | 51.9 |
| YU199273 | ChemDiv | G118-0292 | | 64.8 | 38.0 | 51.4 |
| YU175883 | ChemDiv | C530-0280 | | 68.9 | 33.7 | 51.3 |
| YU164362 | ChemDiv | D089-0344 | | 62.7 | 39.1 | 50.9 |
| YU155939 | ChemDiv | 2434-0139 | | 66.0 | 35.2 | 50.6 |
| YU199272 | ChemDiv | G118-0226 | | 48.2 | 49.4 | 48.8 |
| YU158681 | ChemDiv | 5320-4034 | | 48.2 | 48.9 | 48.5 |
| YU209326 | ChemDiv | J006-1570 | | 48.1 | 48.9 | 48.5 |
| YU187648 | ChemDiv | E762-2304 | | 59.9 | 35.0 | 47.4 |
| YU164400 | ChemDiv | D089-0499 | | 41.7 | 52.7 | 47.2 |
| YU188170 | ChemDiv | E864-1074 | | 38.5 | 55.1 | 46.8 |
| YU179100 | ChemDiv | D089-0253 | | 53.5 | 40.0 | 46.8 |
| YU197082 | ChemDiv | F788-0051 | | 35.9 | 57.3 | 46.6 |
| YU040261 | Enzo | DL-566 | Nelfinavir mesylate | 42.0 | 51.2 | 46.6 |
| YU158754 | ChemDiv | 5465-0013 | | 54.8 | 35.9 | 45.4 |
| YU161684 | ChemDiv | 8017-2854 | | 36.2 | 53.5 | 44.9 |
| YU164332 | ChemDiv | D089-0232 | | 49.5 | 39.4 | 44.4 |
| YU164421 | ChemDiv | D089-0554 | | 35.1 | 51.3 | 43.2 |
| YU207147 | ChemDiv | G856-6079 | | 35.0 | 50.5 | 42.8 |
| YU205819 | ChemDiv | G786-2333 | | 46.8 | 38.7 | 42.8 |
| YU034516 | Enzo | AC-124 | Propafenone | 39.7 | 45.5 | 42.6 |
| YU161686 | ChemDiv | 8017-3017 | | 42.8 | 42.4 | 42.6 |
| YU226705 | Microsource | 1502084 | Proadifen HCl | 43.3 | 41.0 | 42.1 |
| YU164427 | ChemDiv | D089-0563 | | 36.0 | 48.0 | 42.0 |
| YU206375 | ChemDiv | G809-0126 | | 39.2 | 44.3 | 41.8 |
| YU224113 | Enzo | ALX-550-253 | Loperamide-HCl | 35.2 | 47.6 | 41.4 |
| YU177904 | ChemDiv | C796-1275 | | 46.7 | 34.9 | 40.8 |
| YU212319 | ChemDiv | L150-0457 | | 38.4 | 40.5 | 39.4 |
| YU226729 | Microsource | 1503118 | Triflupromazine HCl | 39.5 | 39.2 | 39.4 |
| YU225091 | Microsource | 1500591 | Trifluoperazine HCl | 41.9 | 35.6 | 38.7 |
| YU224969 | Microsource | 1503106 | Bepridil HCl | 33.4 | 43.9 | 38.7 |
| YU156360 | ChemDiv | 3258-0337 | | 34.1 | 39.8 | 36.9 |

Compounds with >33.3% effect in initial screen and hit pick are shown. Data are sorted by mean % effect.

Among these 92 hits, 31 produced >66.6% mean increase in ATP. These included six series of structurally related compounds. One of these comprised two macrolide antibiotics—roxithromycin and erythromycin (see FIG. 5 for structures). The others were structural series of compounds from the ChemDiv library (four compounds from D089, three compounds from 3132, two each from G281, F471, and E612, FIG. 6). Notably, ChemDiv089 and ChemDivE512 shared structural features such as a benzyl ring, connected by an amino-carboxy bond to a 5-ring attached to a second benzyl ring.

These 92 compounds were next screened in dose-response assays, plus an additional six compounds sharing structural similarity to active macrolide antibiotics. Each compound was tested at concentrations of 1.1 μM, 3.3 μM, and 10 μM. 91 of these 98 compounds showed a dose response on KCNJ5$^{G151R}$. The results revealed roxithromycin as the most potent KCNJ5$^{G151R}$ inhibitor (IC$_{50}$ 0.37 μM, FIG. 7). Remarkably, virtually complete rescue of ATP level was achieved, and microscopy revealed vital cells.

All 98 compounds were also tested for inhibition of the other common mutation in APAs, KCNJ5$^{L168R}$. 36 compounds showed a dose response for this channel as well; these included the macrolide compounds roxithromycin, roxithromycin-D7, N-demethyl roxithromycin, erythromycin A oxime, clarithromycin, erythromycin estolate and erythromycin (Table S2). Some other potent inhibitors of KCNJ5$^{G151R}$ channels, e.g. NSC18883 and KC-159, demonstrated either high IC$_{50}$ values or low maximum inhibition of KCNJ5$^{L168R}$ channels.

Figure 6:
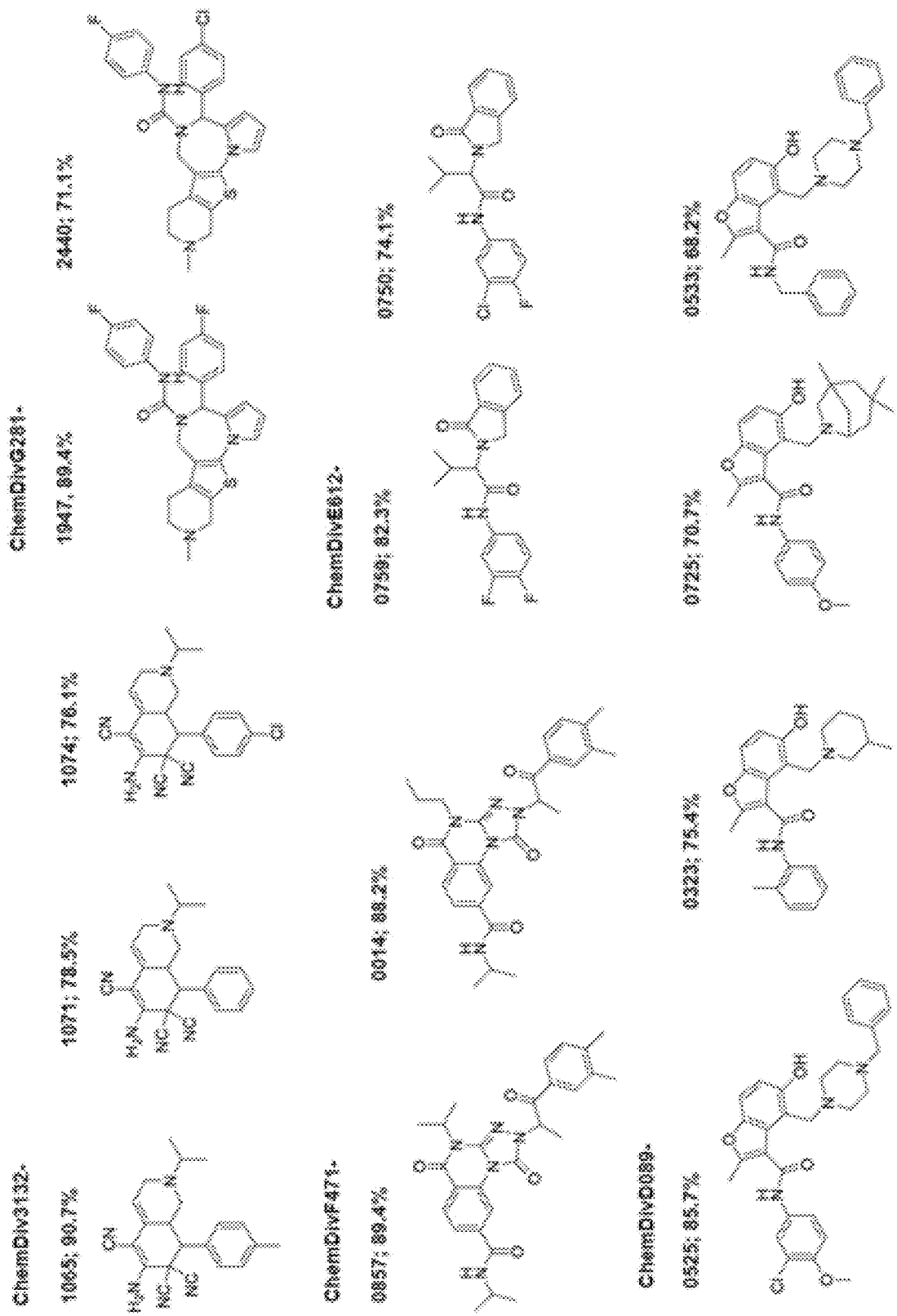
FIG. 6 depicts the structural series from hit pick. Recurrent structural elements from compounds with >66.6% mean effect in primary screen and hit pick. Mean % effect is displayed for each compound. Macrolide structures are shown in FIG. 5.

To screen for compounds that also inhibit KCNJ5$^{WT}$ channels, all 98 compounds were also tested for inhibition of KCNJ5$^{WT}$ by measurement of membrane potential after induction in the presence and absence of drug. Eight macrolides or macrolide derivatives tested had no significant effect on KCNJ5$^{WT}$ channels; several of these showed robust inhibition of both KCNJ5$^{G151R}$ and KCNJ5$^{L168R}$. (FIGS. 5 and 7). Non-macrolide compounds typically were not selective for mutant channels or did not robustly inhibit both KCNJ5$^{G151R}$ and KCNJ5$^{L168R}$ (FIGS. 6 and 7).

Macrolides feature a many-membered lactone ring with one or more deoxy sugars attached Mac Dougall and Chambers, 2011, Chapter 55 in Goodman & Gilman's The Pharmacological Basis of Therapeutics (eds. Brunton, L. L., Chabner, B. A. & Knollmann, B. C., McGraw-Hill, New York). Those with antibiotic activity inhibit protein synthesis by binding of the desosamine sugar and the lactone ring to bacterial 23S ribosomal RNA (Schlunzen et al. 2001, Nature 413:814-821). Binding to other targets produces anti-inflammatory activity (Parnham, 2005, Curr. Opin. Infect. Dis. 18:125-131) and stimulation of gastrointestinal motility (Tsuzuki et al., 1989, Chem. Pharm Bull. 37:2687-2700), which can have clinical utility.

Figure 8:
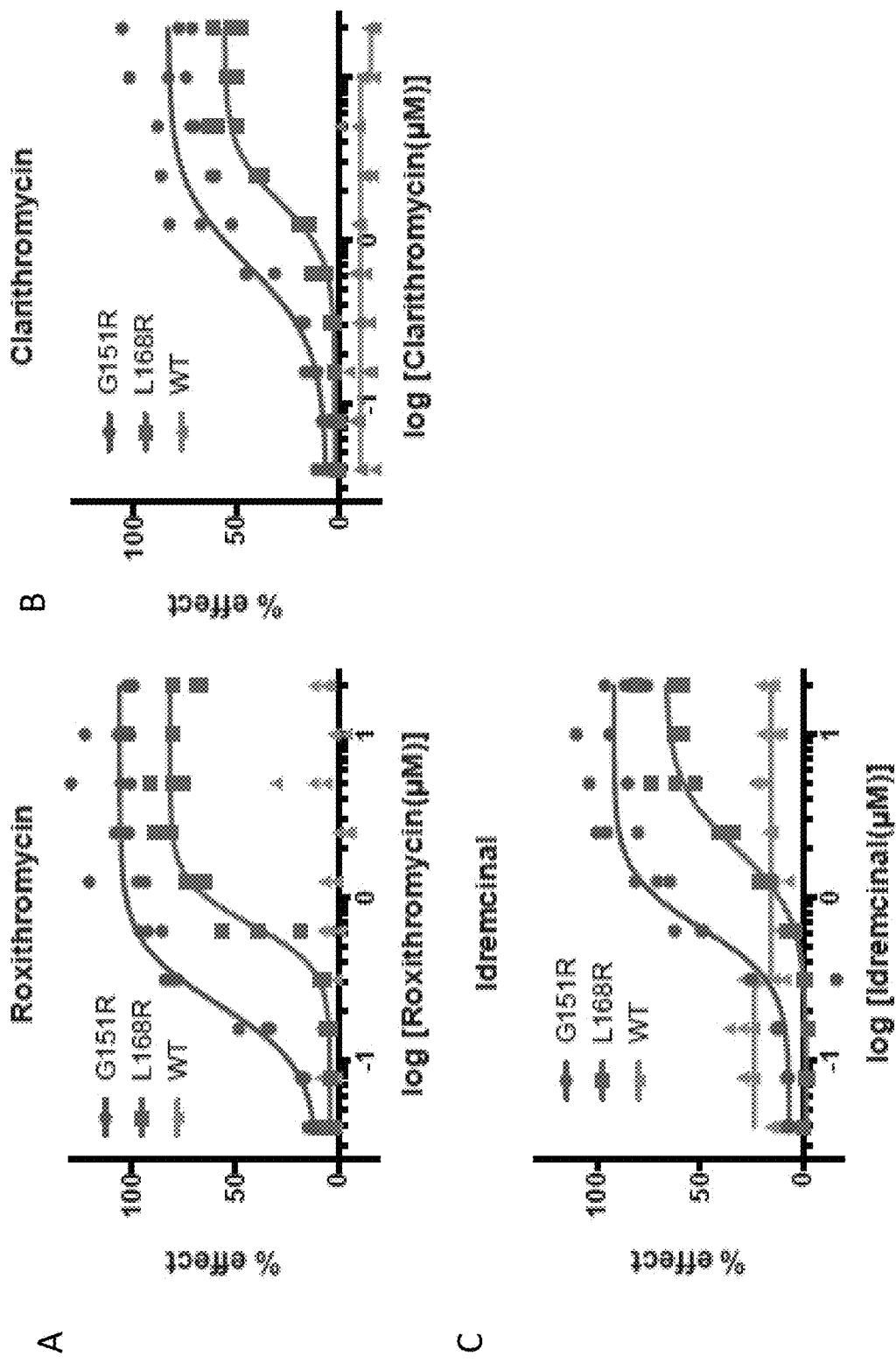
FIG. 8, comprising

To further characterize the structure-activity relationship and inhibitory characteristics of the macrolide series, 14 macrolides and their derivatives were screened in 10-point dilution curves (Table 2, FIG. 8). This analysis demonstrated potent effects of some macrolide antibiotics including roxithromycin and clarithromycin, but negligible activity of others such as flurithromycin. The inhibitory activity of roxithromycin and clarithromycin was greater than that of erythromycin. Clarithromycin differs from erythromycin only by methylation of the hydroxyl group at the 6 position; roxithromycin differs by an N-oxime side chain on the lactone ring. Although not wishing to be bound by any particular theory, these results suggest that these groups may stabilize the interaction between the macrolides and the mutant channel. Similarly, other modifications of the lactone ring in azithromycin and flurithromycin diminish or eliminate inhibition of $KCNJ5^{MUT}$, supporting interaction of ring constituents with mutant channels. In addition, the cladinose sugar of roxithromycin appears to be critical since its removal in decladinose roxithromycin and telithromycin (below activity threshold in primary screen) results in loss of inhibition of $KCNJ5^{MUT}$ (FIG. 5). Erythromycin B showed greater activity than erythromycin C, another component of erythromycin.

domycin, oligomycin C, rapamycin, spiramycin, dirithromycin, rondomycin and natamycin, had little or no activity against $KCNJ5^{G151R}$ in the primary screen (see FIG. 5 for select structures).

Compounds that retain selective channel inhibition without antibiotic or motilide activity were identified, as these would have the most potential for clinical use as $KCNJ5^{MUT}$ inhibitors. In the development of idremcinal, compounds were identified that lacked both antibiotic and motilide activity (Tsuzuki et al., 1989, Chem. Pharm. Bull. 37:2687-2700). Several of these compounds were synthesized, their lack of antibiotic activity confirmed, and tintermediates and target compounds were tested for their effects on $KCNJ5^{MUT}$. PLUX38, 36, 37 and 33 all showed significant inhibition of both mutant channels with no inhibition of $KCNJ5^{WT}$ (FIGS. 9 and 10).

To directly demonstrate that macrolides are inhibiting mutant KCNJ5 channels, electrophysiology of HEK-T cells expressing KCNJ5 homotetramers or KCNJ5/KCNJ3 heterotetramers was performed (Choi et al., 2011, Science

TABLE 2

Inhibition characteristics and structures of macrolides and their derivatives

| Drug Name | Supplier | Supplier ID | G151R | | | L168R | | | WT |
| --- | --- | --- | --- | --- | --- | --- | --- | --- | --- |
| | | | $IC_{50}$ (µM) | minimum inhibition (%) | maximum inhibition (%) | $IC_{50}$ (µM) | minimum inhibition (%) | maximum inhibition (%) | $IC_{50}$ (µM) |
| Roxithromycin | Sigma | R4393 | 0.22 | 9.92 | 105.92 | 0.69 | 3.96 | 81.39 | No fit |
| Roxithromycin-D7 | Toronto Research | R700852 | 0.58 | 1.67 | 96.22 | 0.68 | 3.95 | 70.07 | No fit |
| Idremcinal (EM574) | Enzo | ALX-380-264 | 0.60 | 6.38 | 93.39 | 1.99 | −1.28 | 66.69 | No fit |
| Pseudo Erythromycin Enol Ether | Toronto AResearch | P839500 | 0.65 | 1.58 | 11.13 | No Fit | N/A | N/A | No fit |
| Clarithromycin | Sigma | A3487 | 0.71 | 6.40 | 83.09 | 1.72 | 2.35 | 55.70 | No fit |
| N-demethyl Roxithromycin | Toronto Research | D231265 | 0.82 | 4.50 | 96.20 | 1.18 | 1.12 | 76.95 | No fit |
| Erythromycin B | Santa Cruz Biotech | SC-362735 | 1.23 | 7.15 | 84.36 | 4.73 | 1.62 | 80.00 | No fit |
| Erythromycin A Oxime (Roxithromycin Impurity C) | Toronto Research | E650010 | 2.88 | 2.49 | 84.11 | 8.13 | 0.65 | 60.00 | No fit |
| Azithromycin | Sigma | 75199-25MG-F | 5.69 | 5.11 | 32.00 | 8.05 | 0.71 | 12.01 | No fit |
| Anhydro-erythromycin A | Toronto Research | A638950 | 8.60 | 5.61 | 60.00 | No fit | N/A | N/A | No fit |
| Erythromycin C | Santa Cruz Biotech | SC-362736 | 9.19 | 6.72 | 75.00 | 12.18 | 1.41 | 18.43 | No fit |
| Erythromycin | Sigma | E6376 | 10.53 | 3.55 | 90.00 | 11.76 | 0.71 | 25.00 | No fit |
| Dirithromycin | Sigma | D4065 | 15.80 | 1.31 | 18.29 | No fit | N/A | N/A | No fit |
| Flurithromycin | Waterstone Tech | 40589 | No fit | N/A | N/A | No fit | N/A | N/A | No fit |

Results of a four-parameter non-linear regression of log-dose versus response of macrolides and their derivatives ($KCNJ5^{G151R}$, $KCNJ5^{L168R}$ and $KCNJ5^{WT}$). Compounds were tested at 20, 10, 5, 2.5, 1.25, 0.625, 0.3125, 0.1563, 0.0781 and 0.0391 µM concentrations (N=3). $IC_{50}$, half maximal inhibitory concentration. Examples of dose response curves are shown in FIG. 8.

Figure 11:
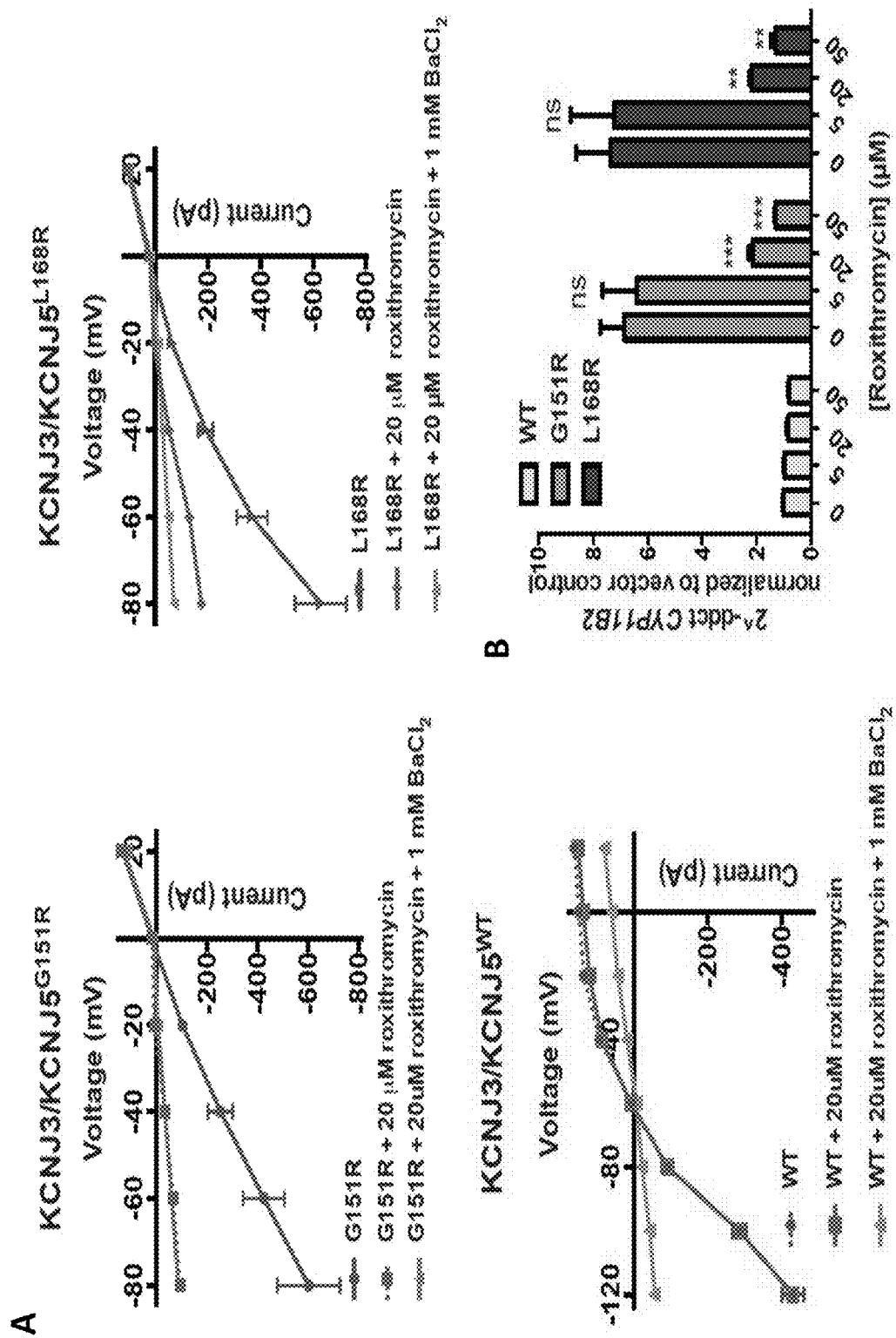
FIG. 11, comprising

In addition to macrolide antibiotics, non-antibiotic macrolide derivatives such as the motilin receptor agonist idremcinal (EM 574) (Tsuzuki et al., 1989, Chem. Pharm. Bull. 37:2687-2700; Sunazuka et al., 1989, Chem. Pharm. Bull. 37:2701-2709) were potent and selective inhibitors of $KCNJ5^{MUT}$ (idremcinal $IC_{50}$ 0.60 µM for $KCNJ5^{G151R}$ and 1.76 µM for $KCNJ5^{L168R}$, no dose response for $KCNJ5^{WT}$, FIG. 5). Several other compounds with macrolide structures, including troleandomycin, josamycin, kitasamycin, olean- 331:768-772). Currents were measured using the whole-cell patch clamp technique (Choi et al., 2011, Science 331:768-772; Scholl et al., 2012, Proc. Natl. Acad. Sci. U.S.A. 109:2533-2538). FIG. 11A shows cation currents of heterotetramers recorded in physiological solutions (high extracellular Nat, high intracellular $K^+)^2$. Expression of $KCNJ3/KCNJ5^{WT}$ channels resulted in inwardly rectifying $K^+$ currents and a negative reversal potential as a result of high $K^+$ conductance (FIG. 11A). Expression of $KCNJ3/KCNJ5^{G151R}$ channels caused significant depolarization as a result of $Na^+$ conductance. Addition of 20 µM roxithromycin led to almost complete inhibition of $KCNJ3/KCNJ5^{G151R}$ currents. Of note, a shift of the reversal potential to more negative voltages was observed after addition of roxithromycin, consistent with inhibition of the depolarizing Na conductance. Similar results were obtained for KCNJ3/

Figure 12:
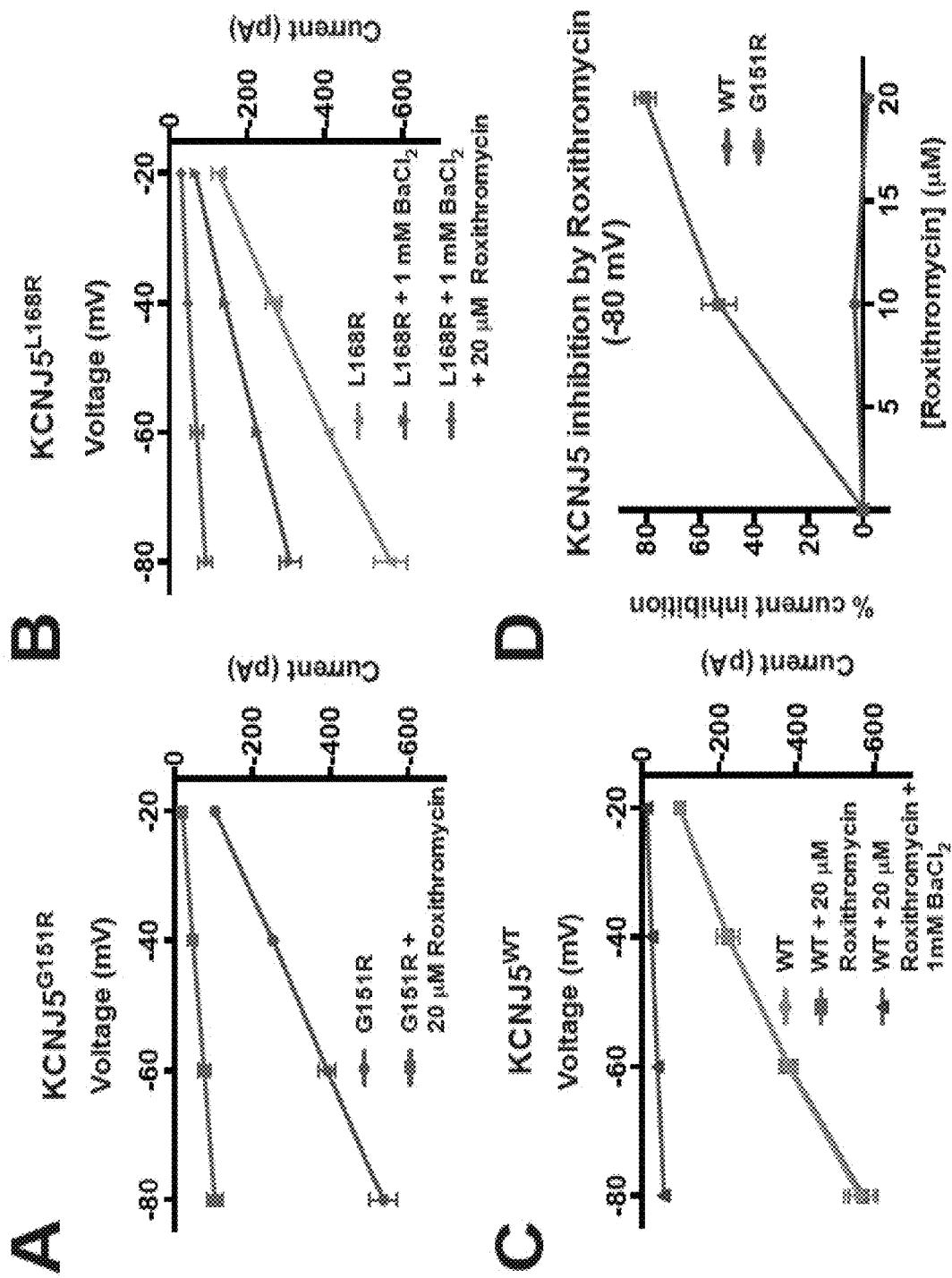
FIG. 12, comprising
Figure 13:
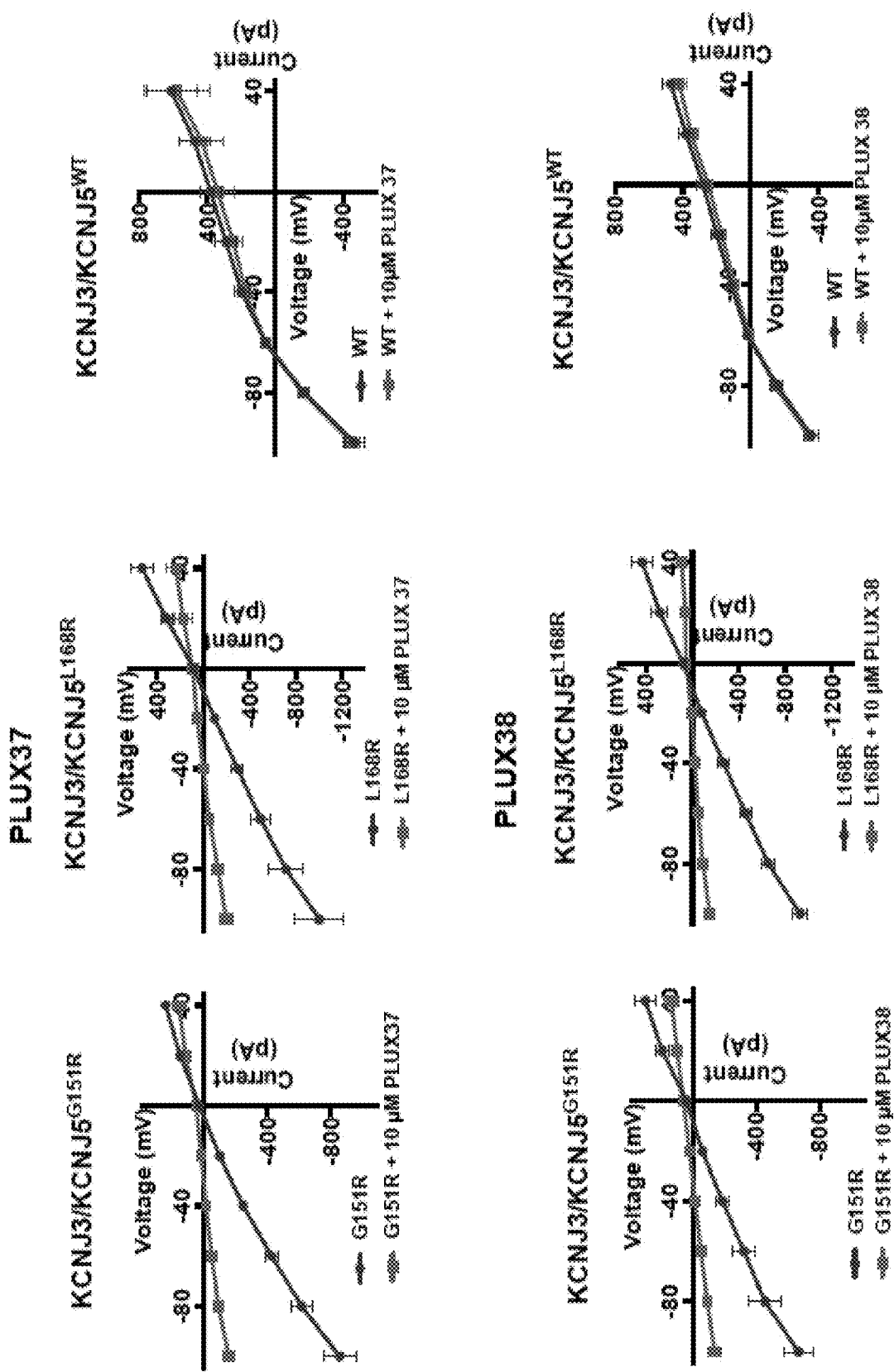
FIG. 13 is a series of graphs depicting experimental data demonstrating the inhibition of mutant KCNJ5 by PLUX37 and PLUX38. Cation currents of heterotetramers of KCNJ3 and mutant or WT KCNJ5 were measured with the perfomated patch clamp technique without (blue) or with (red) 10 μM inhibitor (upper panels, PLUX37; lower panels, PLUX38). Error bars represent standard error of the mean. Extracellular solution: 140 mM NaCl/5 mM KCl, intracellular solution: 140 mM KCl.

KCNJ5$^{L168R}$. The remaining current for KCNJ3/KCNJ5$^{L168R}$ was blocked by the known potassium channel pore blocker barium and may represent potassium current. In contrast, roxithromycin showed no inhibition of potassium currents in KCNJ3/KCNJ5$^{WT}$ channels, and currents were sensitive to barium. Parallel studies of KCNJ5$^{G151R}$ homotetramers demonstrated 80% inhibition with 20 μM roxithromycin, and 53% inhibition with 10 μM roxithromycin (FIG. 12). Although not wishing to be bound by any particular theory, these results suggest that IC$_{50S}$ for current inhibition are higher than those for rescue of cellular lethality. These results demonstrate direct inhibition by roxithromycin of channels containing KCNJ5 mutations. Similarly, PLUX37 and PLUX38, which were tested as representative synthesized inhibitors, demonstrated specific inhibition of mutant KCNJ5 in electrophysiological studies at 10 μM concentration (FIG. 13).

To assess effects of KCNJ5 inhibition on aldosterone production, NCI-H295R cells were transfected with KCNJ5$^{WT}$, KCNJ5$^{G151R}$ and KCNJ5$^{L168R}$ by electroporation. This cell line is derived from a human adrenocortical carcinoma and represents a commonly used in vitro model of zona glomerulosa aldosterone production (Wang et al. 2012, Horm. Metab. Res. 44:245-250). By real-time PCR, expression levels of CYP11B2 were measured, encoding aldosterone synthase, the rate-limiting enzyme in aldosterone biosynthesis (FIG. 11B). Cells transfected with KCNJ5$^{G151R}$ or KCNJ5$^{L168R}$ showed an ~7-fold increase in CYP11B2 expression compared to cells transfected with KCNJ5$^{WT}$. Importantly, roxithromycin inhibited expression of CYP11B2 in a dose-dependent fashion in cells expressing either KCNJ5$^{G151R}$ (p=0.0006 at 20 μM)) or KCNJ5$^{L168R}$ (p=0.0034 at 20 μM), whereas levels showed virtually no change in cells expressing KCNJ5$^{WT}$.

These results identify specific macrolides that selectively and potently inhibit channels harboring the two mutant forms of KCNJ5 (KCNJ5$^{G151R}$ and KCNJ5$^{L168R}$) that cause a very large fraction of aldosterone-producing adenomas. Although not wishing to be bound by any particular theory, these findings suggest that these or related compounds could be used for the clinical diagnosis of APAs. Because aldosterone has a plasma half-life of only ~30 minutes (Schulte et al., 1987, Clin. Endocrinol. 27:655-662), short-term inhibition of aldosterone production is sufficient to produce rapid reductions in plasma aldosterone levels and urinary excretion (Litchfield et al., 1997, J. Clin. Endocrinol. Metab. 82:3570-3573). Thus in patients in whom an APA is suspected from the finding of hypertension due to primary aldosteronism, short-term administration of such a drug would be expected to acutely reduce aldosterone production in patients in whom somatic KCNJ5 mutations are the cause of APAs. Given the larger size of tumors carrying KCNJ5 mutations on imaging (Scholl et al., 2015, Clin. Endocrinol. 83:779-789), radiological evidence of a unilateral adrenal tumor, in conjunction with the reduction in aldosterone production may be sufficient to proceed to surgical intervention, obviating the need for invasive adrenal vein sampling. The large fraction of APAs caused by these mutations suggests that such a test would have substantial clinical impact. This approach to diagnosis may improve the identification of patients whose hypertension could be cured by surgical intervention.

This method may be tested with roxithromycin, which is marketed in the European Union for treatment of bacterial infections. After a single dose of 300 mg to healthy adults, maximum serum concentrations are 16.4 mg/L (~17 μM) (Puri and Lassman, 1987, J. Antimicrob. Chemother. 20 Suppl. B:89-100), concentrations that strongly inhibit KCNJ3/KCNJ5$^{MUT}$ heterotetramers and KCNJ5$^{MUT}$ homotetramers in vitro.

Moreover, the long history of pharmacologic use of macrolides, with their established safety and oral bioavailability, suggests a useful path forward to develop drugs similar to the tool compounds PLUX37 and PLUX38 that may be optimized for channel inhibition, lack of antibiotic and gastrointestinal effects, and pharmacokinetics. The results described herein demonstrate structure activity relationships that can likely be built upon to achieve these goals.

In addition to a role in the diagnosis of APAs, inhibitors of KCNJ5$^{MUT}$ may be useful for the treatment of hypertension in patients with APAs due to these mutations, potentially eliminating the need for surgery. By inhibiting the proliferative signal as well as aldosterone production, the tumor might shrink with treatment using inhibitors of KCNJ5$^{MUT}$, resulting in withdrawal of therapy. The results described herein indicate that channel inhibition can be separated from antibiotic and gastrointestinal effects. Dopamine agonists have dramatically changed the treatment of prolactinomas, hormone-producing tumors of the pituitary gland, as they typically restore normal prolactin levels and reduce tumor mass, with recent data demonstrating that therapy can be withdrawn in a subset of patients after normalization of hormone levels and tumor disappearance (Colao and Savastano, 2011, Jat. Rev. Endocrinol. 7:267-278).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing a subject with an adrenal disease or disorder associated with mutant KCNJ5, the method comprising:

a) measuring at least one sign or symptom of the adrenal disorder in the subject, b) administering a mutant KNCJ5 inhibitor or a salt or solvate thereof wherein the mutant KCNJ5 inhibitor compound, or a salt or solvate thereof, is at least one compound selected from the group consisting of: erythromycin: erythromycin A oxime; clarithromycin; roxithromycin; idremcinal; 5-hydroxy-N-(4-methoxyphenyl)-2-methyl-4-((1,3,3-trimethyl-6-azabicyclo[3.2.1]
octan-6-yl)methyl)benzofuran-3-carboxamide;
5-hydroxy-2-methyl-N-phenyl-4-((1,3,3-trimethyl-6-azabicyclo[3.2.1]octan-6-yl)methyl)benzofuran-3-carboxamide; 5-hydroxy-2-methyl-4-(piperidin-1-ylmethyl)-N-(3-(trifluoromethyl)phenyl)benzofuran-3-carboxamide; and a compound selected from the group consisting of:

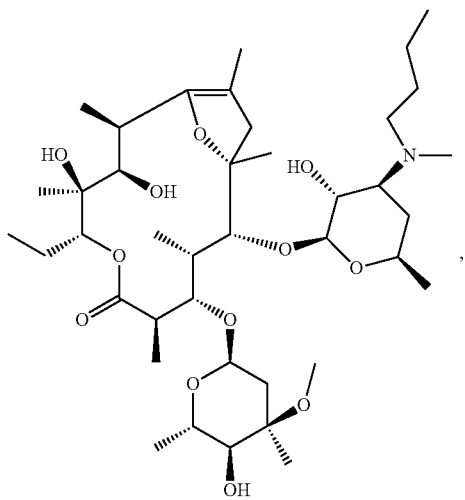

,

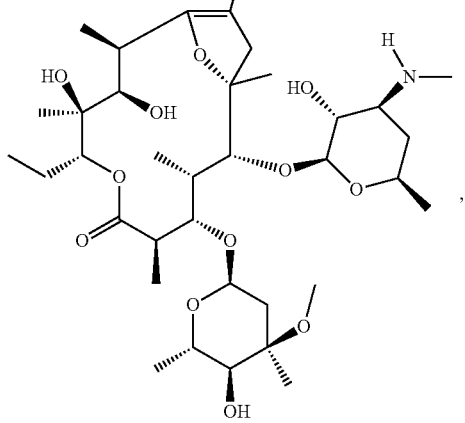

,

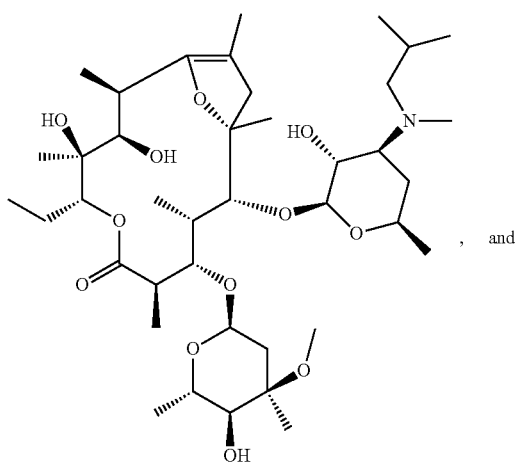

, and

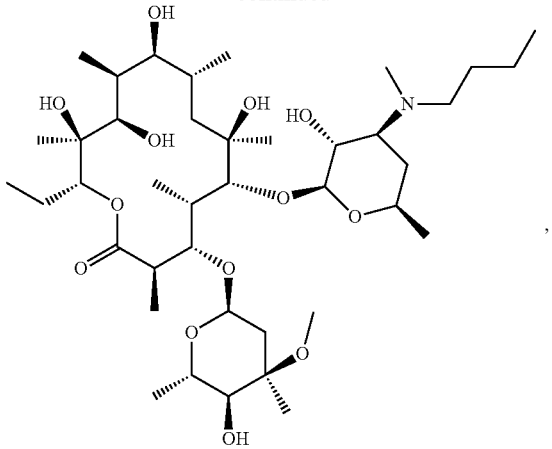 [SMILES: CCCCN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)O[C@H](CC)[C@@](C)(O)[C@H](O)[C@@H](C)[C@@H](O)[C@H](C)C[C@@]2(C)O)[C@@H]1O]

, c) measuring the at least one sign or symptom of the adrenal disorder in the subject after administering a mutant KNCJ5 inhibitor compound to the subject, wherein, when the at least one sign or symptom of the adrenal disorder is improved after administration of the mutant KNCJ5 inhibitor compound, the subject is diagnosed as having an adrenal disease or disorder associated with mutant KCNJ5.

2. The method of claim 1, wherein the mutant KCNJ5 has at least one mutation selected from the group consisting of: G151X, L168X, T158X and E145X.

3. The method of claim 1, wherein the mutant KCNJ5 has at least one mutation selected from the group consisting of: G151R, L168R, T158A and E145Q.

4. The method of claim 1, wherein the subject is human.

5. The method of claim 1, wherein the adrenal disease or disorder is at least one disease or disorder selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

6. The method of claim 1, wherein the at least one sign or symptom of the adrenal disease or disorder measured in step a) is selected from the group consisting of an elevated aldosterone level in the serum of the subject and an elevated aldosterone level in the urine of the subject.

7. The method of claim 6, wherein the subject is diagnosed as having at least one disease or disorder selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization when at least one of an elevated aldosterone level in the serum of the subject and an elevated aldosterone level in the urine of the subject is measured in the subject after administering a mutant KNCJ5 inhibitor compound to the subject.

8. A method of treating an adrenal disease or disorder in a subject in need thereof, the method comprising: administering to the subject a therapeutically active amount of a KCNJ5 inhibitor compound, or salt or solvate thereof, wherein the KCNJ5 inhibitor compound, or salt or solvate thereof, is at least one compound selected from the group consisting of: erythromycin; erythromycin A oxime; clarithromycin; roxithromycin; idremcinal; 5-hydroxy-N-(4- methoxyphenyl)-2-methyl-4-((1,3,3-trimethyl-6-azabicyclo[3.2.1]octan-6-yl)methyl)benzofuran-3-carboxamide; 5-hydroxy-2-methyl-N-phenyl-4-((1,3,3-trimethyl-6-azabicyclo[3.2.1]octan-6-yl)methyl)benzofuran-3-carboxamide; 5-hydroxy-2-methyl-4-(piperidin-1-ylmethyl)-N-(3-(trifluoromethyl)phenyl)benzofuran-3-carboxamide; and a compound selected from the group consisting of:

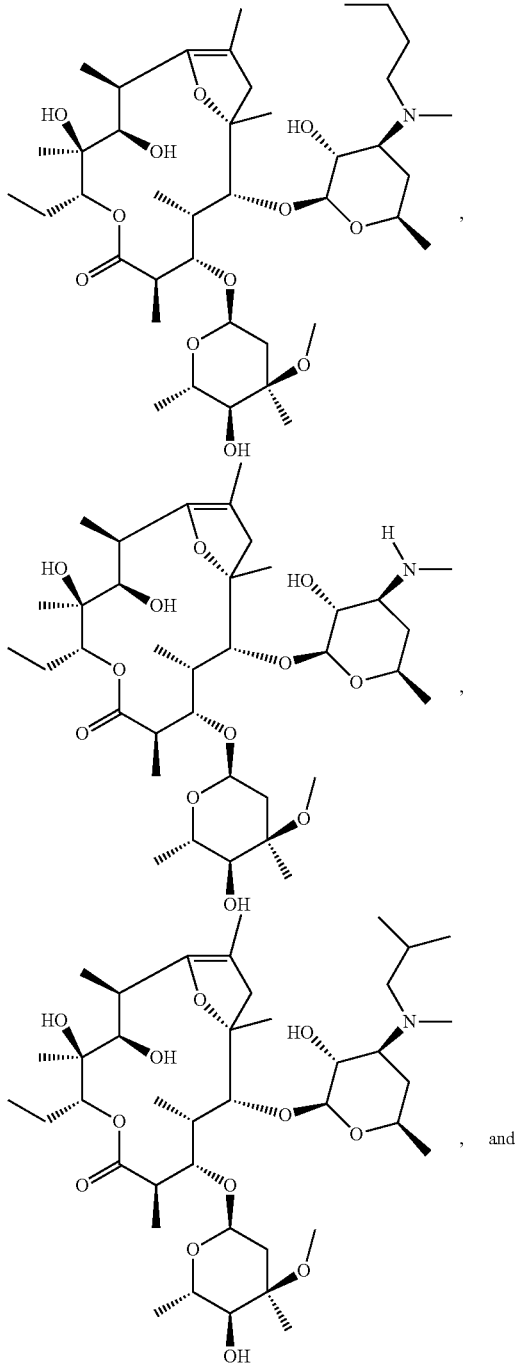

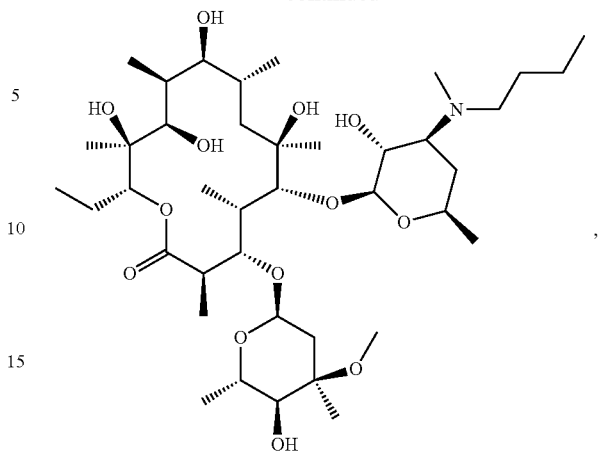

wherein the subject has been diagnosed as having an adrenal disease or disorder, and wherein after the mutant KCNJ5 inhibitor compound is administered to the subject, the adrenal disease or disorder is treated.

9. The method of claim 8, wherein the subject has at least one mutation in KCNJ5.

10. The method of claim 8, wherein the subject has at least one mutation in KCNJ5 in or near the KCNJ5 selectivity filter.

11. The method of claim 8, wherein the subject has at least one mutation in KCNJ5, wherein the at least one mutation is at the amino acid residue position from about 140 to about 180 relative to SEQ ID NO:7.

12. The method of claim 8, wherein the at least one mutation is at least one selected from the group consisting of: G151X, L168X, T158X and E145X.

13. The method of claim 8, wherein the at least one mutation is at least one selected from the group consisting of: G151R, L168R, T158A and E145Q.

14. The method of claim 8, wherein the subject is human.

15. The method of claim 8, wherein the disease or disorder is an adrenal disease or disorder.

16. The method of claim 8, wherein the adrenal disease or disorder is at least one disease or disorder selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

* * * * *